(12) United States Patent
Barreca et al.

(10) Patent No.: US 11,465,977 B2
(45) Date of Patent: Oct. 11, 2022

(54) PROCESS FOR THE PREPARATION OF SPHINGOSINE-1-PHOSPHATE RECEPTOR AGONIST

(71) Applicant: QUÍMICA SINTÉTICA, S.A., Alcalá de Henares (ES)

(72) Inventors: Giuseppe Barreca, Sirtori (IT); Luca Carcone, Milan (IT); Maurizio Taddei, Monteriggioni (IT); Damian Mark Grainger, Ely (GB); Samantha Louise Staniland, Royston (GB); Claudio Cianferotti, Siena (IT); Giovanni Marras, Galliate (IT)

(73) Assignee: QUÍMICA SINTÉTICA, S.A., Alcalá de Henares (ES)

( * ) Notice: Subject to any disclaimer, the term of this patent is extended or adjusted under 35 U.S.C. 154(b) by 0 days.

(21) Appl. No.: 17/279,493

(22) PCT Filed: Sep. 25, 2019

(86) PCT No.: PCT/EP2019/075831
§ 371 (c)(1),
(2) Date: Mar. 24, 2021

(87) PCT Pub. No.: WO2020/064818
PCT Pub. Date: Apr. 2, 2020

(65) Prior Publication Data
US 2022/0033365 A1 Feb. 3, 2022

(30) Foreign Application Priority Data

Sep. 25, 2018 (EP) .................................... 18382684

(51) Int. Cl.
C07D 271/06 (2006.01)
C07C 255/58 (2006.01)
C07D 319/06 (2006.01)
C07D 413/10 (2006.01)

(52) U.S. Cl.
CPC .......... *C07D 271/06* (2013.01); *C07C 255/58* (2013.01); *C07D 319/06* (2013.01); *C07D 413/10* (2013.01)

(58) Field of Classification Search
CPC ................................................. C07D 271/06
See application file for complete search history.

(56) References Cited

U.S. PATENT DOCUMENTS 8,362,048 B2 * 1/2013 Martinborough ....... A61P 29/00
548/131
2008/0249093 A1 10/2008 Colandrea et al.

FOREIGN PATENT DOCUMENTS

| EP | 2 291 080 B1 | 8/2015 |
|---|---|---|
| WO | WO 2009/151529 A1 | 12/2009 |
| WO | WO 2011/060389 A1 | 5/2011 |
| WO | WO 2011/060392 A1 | 5/2011 |
| WO | WO 2018/028557 A | 2/2018 |
| WO | WO 2018/064356 A1 | 4/2018 |
| WO | WO 2018/208855 A1 | 11/2018 |
| WO | WO 2019/058290 A1 | 3/2019 |

OTHER PUBLICATIONS

Burke et al., "Handbook of Reagents for Organic Synthesis, Oxidizing and Reducing Agents", John Wiley & Sons, (1999, reprinted Jul. 2005), pp. 1 and 6.
Greene et al., "Protective Groups in Organic Synthesis", Third Edition, 1999, John Wiley & Sons, Inc., pp. 23-113, pp. 113-148, pp. 149-179 or pp. 179-187 or pp. 503-598.
Harris et al., "The Fit For Purpose Development of S1P$_1$ Receptor Agonist GSK2263167 Using a Robinson Annulation and Saegusa Oxidation to Access an Advanced Phenol Intermediate", XP-002787670, Organic Process Research & Development, 2013, 17, pp. 1239-1246. DOI: http://dx doi org/10 1021/op400162p.
International Search Report for PCT/EP2019/075831 (PCT/ISA/210) dated Nov. 20, 2019.
Written Opinion of the International Searching Authority for PCT/EP2019/075831 (PCT/ISA/237) dated Nov. 20, 2019.

* cited by examiner

*Primary Examiner* — Golam M Shameem
(74) *Attorney, Agent, or Firm* — Birch, Stewart, Kolasch & Birch, LLP.

(57) ABSTRACT

Industrially viable and advantageous processes for the preparation of Ozanimod are described. The invention also discloses the intermediates obtained in the process.

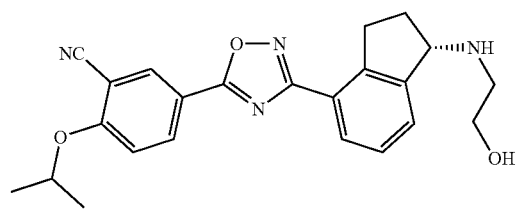

18 Claims, 1 Drawing Sheet

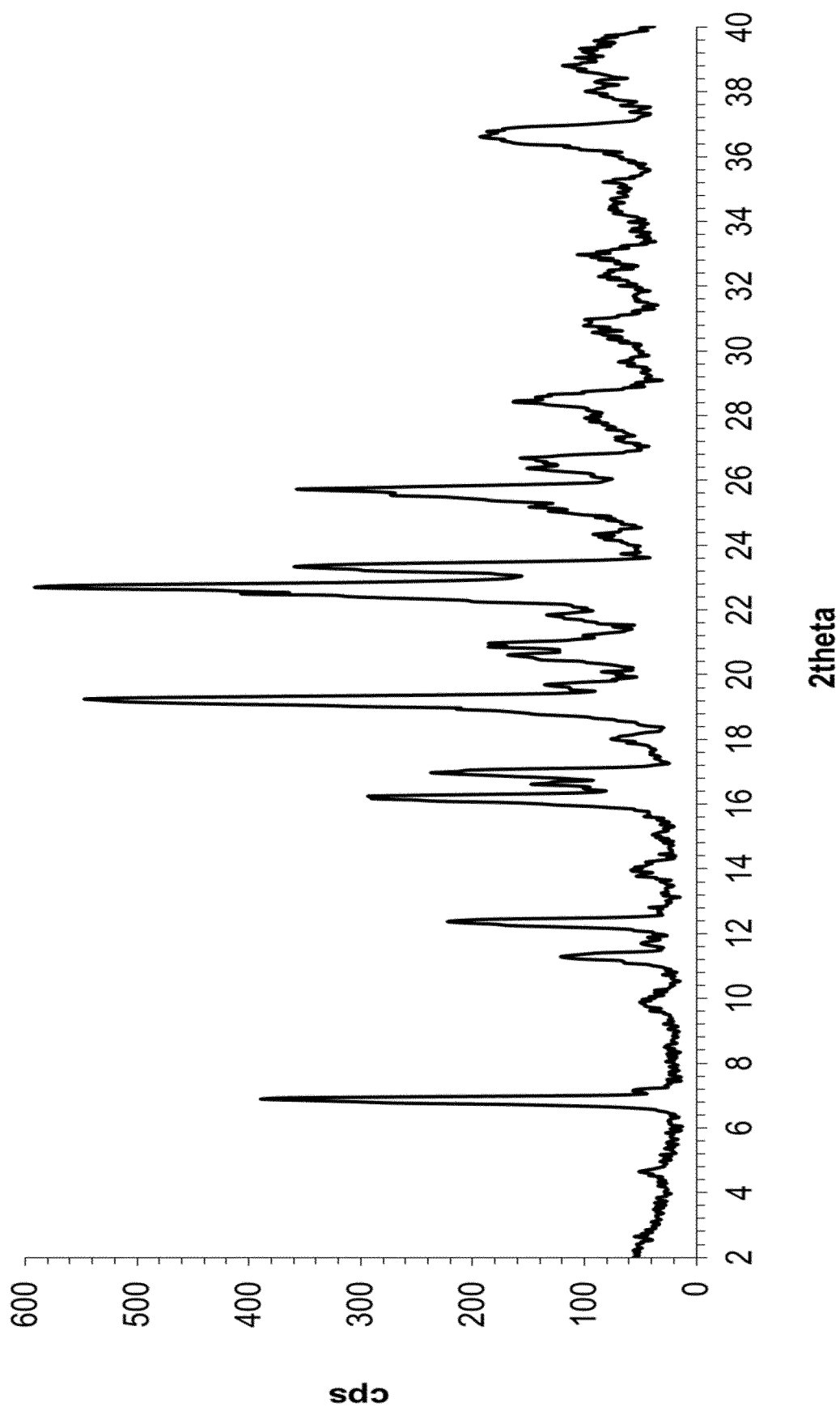

PROCESS FOR THE PREPARATION OF SPHINGOSINE-1-PHOSPHATE RECEPTOR AGONIST

FIELD OF THE INVENTION

The present invention relates to industrially viable and advantageous processes for the preparation of sphingosine-1-phosphate (S1P) receptor agonists and of intermediate compounds useful in the synthesis thereof.

STATE OF THE ART

Ozanimod is the INN denomination assigned to the compound having IUPAC name (S)-5-(3-(1-((2-hydroxyethyl)amino)-2,3-dihydro-1H-inden-4-yl)-1,2,4-oxadiazol-5-yl)-2-isopropoxy-benzonitrile and the formula reported below:

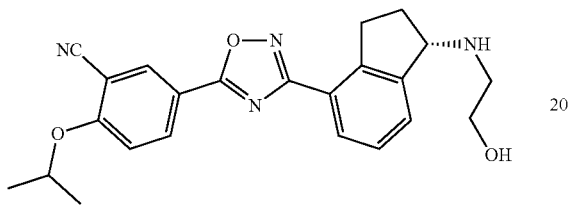

Ozanimod is an investigational immunomodulatory drug currently in phase III clinical trials for the therapy of relapsing multiple sclerosis (RMS) and ulcerative colitis (UC). It acts as a sphingosine-1-phosphate receptor agonist, sequestering lymphocytes to peripheral lymphoid organs and away from their sites of chronic inflammation.

Ozanimod and other similar compounds were first described in international patent application WO 2009/151529 A1. The process described therein entails, as key steps, treatment of 1-hydroxy-2,3-dihydro-1H-indene-4-carbonitrile with hydroxylamine hydrochloride; coupling of (E)-N',1-dihydroxy-2,3-dihydro-1H-indene-4-carboximidamide with 3-cyano-4-isopropoxybenzoic acid in the presence of EDCI and HOBt; treatment of 5-(3-(1-hydroxy-2,3-dihydro-1H-inden-4-yl)-1,2,4-oxadiazol-5-yl)-2-isopropoxybenzonitrile with thionyl chloride and, subsequently, with 2-aminoethanol to yield Ozanimod in the form of a racemic mixture:

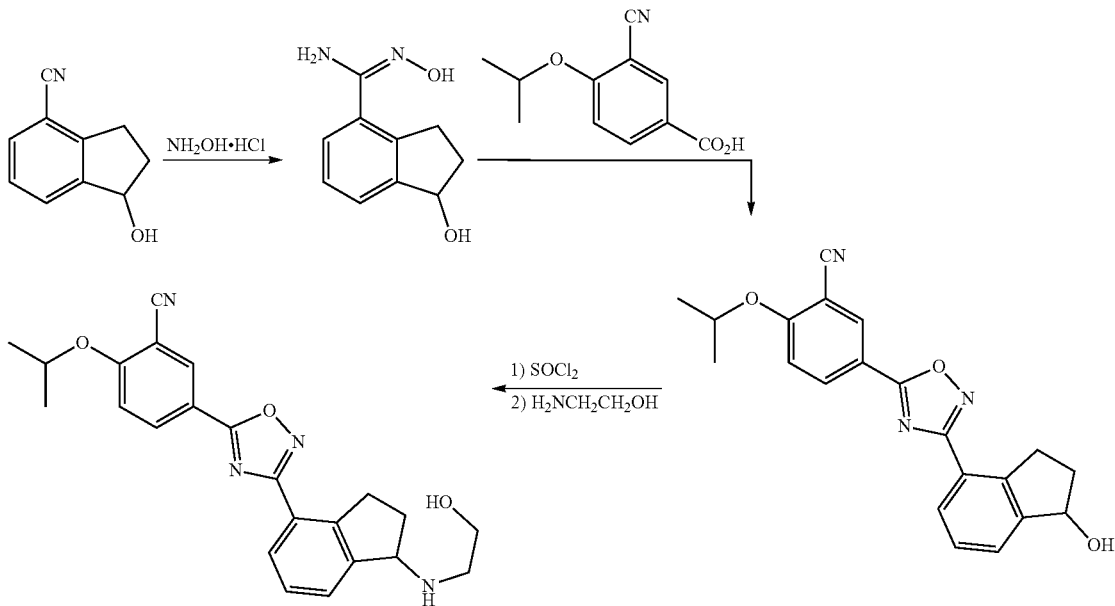

On industrial scale, the use of this synthetic route has several drawbacks caused by the low transformation yield of 5-(3-(1-hydroxy-2,3-dihydro-1H-inden-4-yl)-1,2,4-oxadiazol-5-yl)-2-isopropoxybenzonitrile into Ozanimod (i.e. 23%, see paragraph [0107] of EP 2291080 B1). An alternative process for the preparation of Ozanimod has been described in the international application WO 2011/060392 A1. According to this document, a hydrochloride salt of this API can be prepared by (i) reacting 1-oxo-2,3-dihydro-1H-indene-4-carbonitrile with the Ellman's sulfinamide in the presence of titanium ethoxide, (ii) in-situ reducing the resulting (S)—N-(4-cyano-2,3-dihydro-1H-inden-1-ylidene)-2-methylpropane-2-sulfinamide and (iii) converting (S)—N—((S)-4-cyano-2,3-dihydro-1H-inden-1-yl)-2-methylpropane-2-sulfinamide into the desired product.

Although being an interesting approach, it is not practical for multikilogram synthesis, because, e.g., of the use of cryogenic temperatures during the reduction of (S)—N-(4-cyano-2,3-dihydro-1H-inden-1-ylidene)-2-methylpropane-2-sulfinamide with sodium borohydride. A titanium-mediated imine formation in the synthesis of an Ozanimod-related compound has been disclosed in the international application WO 2018/028557 A1:

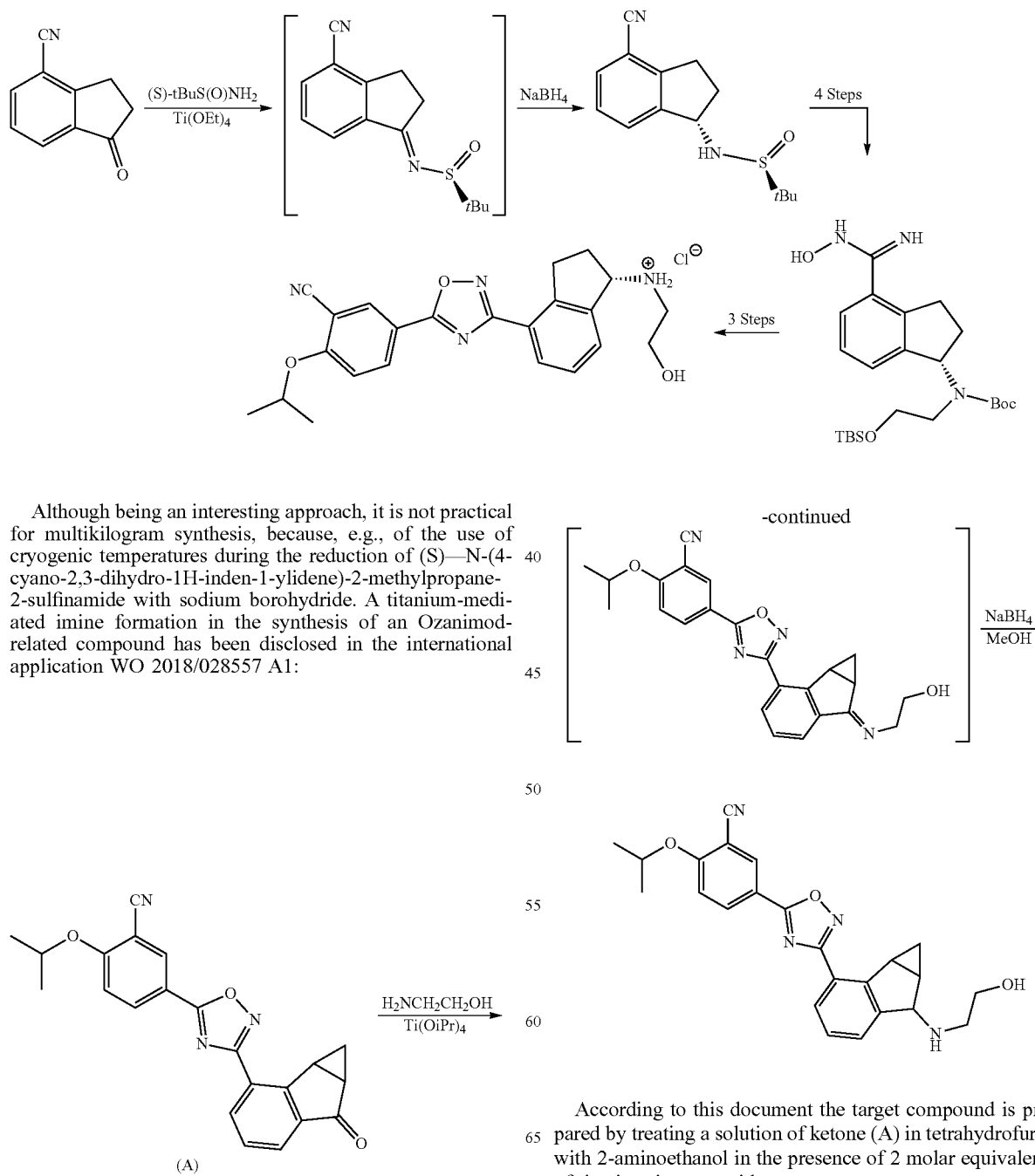

According to this document the target compound is prepared by treating a solution of ketone (A) in tetrahydrofuran with 2-aminoethanol in the presence of 2 molar equivalents of titanium isopropoxide.

In addition to the unsatisfactory yield (29%), this reaction necessarily produces a stoichiometric amount of titanium and boron salts which must be disposed of properly, resulting in additional costs.

*Organic Process Research and Development* 2013, vol. 13, pages 1239-1246, describes the use of 3-cyano-4-isopropyloxy-benzoyl chloride in the synthetic preparation of a $S1P_1$ receptor agonist.

Object of this invention is, therefore, to provide new methods for the synthesis of sphingosine-1-phosphate receptor agonists or salts thereof, in particular Ozanimod or a salt thereof, with excellent yields and providing said sphingosine-1-phosphate receptor agonists of adequate purity for pharmaceutical use.

SUMMARY OF THE INVENTION

These objectives were achieved with the present invention, which, in a first aspect thereof, relates to a process for the preparation of a compound of general formula (7), or a salt thereof:

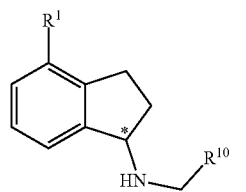

said process comprising the following steps:
a) reacting an indanone of general formula (1) with a compound of general formula (2) so as to provide a compound of general formula (3);

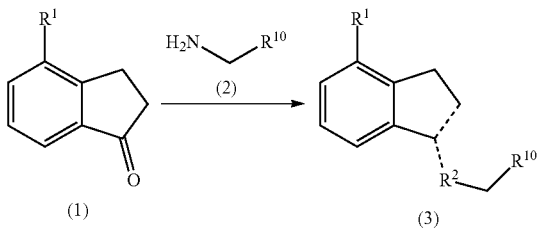

b) converting said compound of general formula (3) into a compound of general formula (7) or a salt thereof; wherein:

$R^1$ is selected from the group consisting of —CN and 1,2,4-oxadiazole, said 1,2,4-oxadiazole being attached to the bicycle via carbon 3 and optionally substituted in position 5 with a 3'-cyano-4'-isopropoxyphenyl group;
one of the dashed lines indicates a single bond and the other one a double bond;
when the dashed line linked to $R^2$ is a double bond, $R^2$ is N, and when the dashed line linked to $R^2$ is a single bond, $R^2$ is NH;
$R^{10}$ is selected from the group consisting of —$CH_2OH$, —$CH_2OPg$ and —$CO_2R^{12}$;
$R^{12}$ is selected from the group consisting of H and a linear or branched (C1-C8)alkyl-optionally substituted with a (C6-C10)aryl-; and Pg is an oxygen protecting group;
said process being characterized in that step a) is carried out in the absence of titanium alkoxides (preferably in the absence of titanium-based Lewis acids).

In a second aspect thereof, the present invention relates to a process for the preparation of an enantiomerically pure amine of general formula (12) or a salt thereof, said process comprising:
h) providing an azide of formula (13):

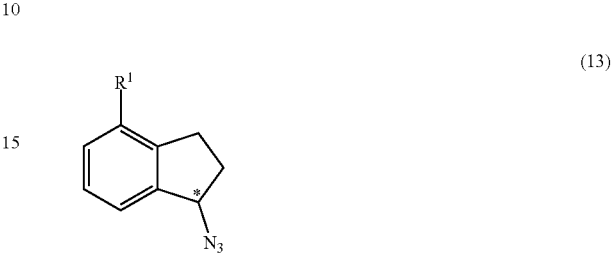

i) converting said azide of formula (13) into an amine of formula (12) or a salt thereof:

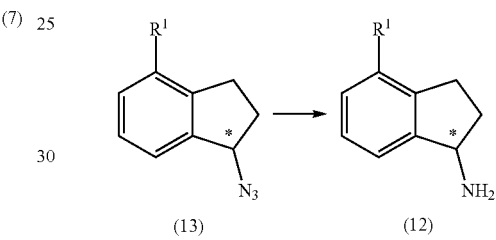

j) optionally converting said amine of formula (12) or the salt thereof into an enantiomerically pure amine of formula (12) or an enantiomerically pure salt thereof by treatment with a chiral or an achiral Brønsted acid;
wherein $R^1$ assumes the meanings reported above;
said process being characterized in that the reduction of step i) is performed according to Staudinger reaction conditions.

In a third aspect thereof, the invention relates to intermediate compounds obtained in the processes.

BRIEF DESCRIPTION OF THE DRAWINGS

FIG. 1 depicts the X-Ray powder diffractogram of a hemitartrate salt of an enantiomerically pure amine of formula (12) in which $R^1$ is —CN.

DETAILED DESCRIPTION OF THE INVENTION

All terms used in the present application, unless otherwise indicated, must be interpreted in their ordinary meaning as known in the technical field. Other more specific definitions for some terms used in the present application are given below and are intended to be applied uniformly to the entire description and claims, unless otherwise indicated.

In general, the nomenclature used in this Application is based on AUTONOM™ v.4.0, a Beilstein Institute computerized system for the generation of IUPAC systematic nomenclature. If there is a discrepancy between a depicted structure and a name given to that structure, the depicted structure should be considered correct. Furthermore, if the stereochemistry of a structure or a portion of a structure is not indicated with, for example, bold or dashed lines, the structure or portion of the structure has to be interpreted as encompassing all existing stereoisomers of it.

The compounds prepared by the processes of the present invention may exist and may be used or isolated as racemic mixtures, in enantiomerically pure forms or as enantiomeric enriched mixtures. It is to be understood that the processes of the present invention can give rise to any of the previous forms or a combination thereof. It is to be further understood that the products of the processes described herein, can be isolated as enantiomerically pure forms and/or as enantiomerically enriched mixtures and/or as racemic mixtures.

The sign "*" (asterisk) present in some formulae of the description indicates a stereogenic (asymmetric) center, although the absence of asterisks does not necessarily imply that the compound lacks a stereocenter. Such formulae may refer to the racemate, to enantiomerically enriched mixtures or to individual enantiomers, which may or may not be substantially pure.

A mixture of (R,S) enantiomers can contain the two enantiomers in any ratio to each other. The enantiomeric purity is generally expressed as "enantiomeric excess" or ee and is defined, for example for the (S) enantiomer, as $[(S-R)/(R+S)] \times 100$, wherein S and R are respectively the amounts of the (S) and (R) enantiomers (as determined for example by GC or HPLC on a chiral stationary phase or polarimetry).

The term "racemic" refers to a sample of a chiral compound which contains both the (+) and (−) isomers in equal amount.

The term "enantiomerically enriched" as used herein means that one of the enantiomers of a compound is present in excess compared to the other enantiomer.

The term "enantiomerically pure" as used herein means that the enantiomeric purity is usually at least about 96%, preferably at least 98%, more preferably at least 99%, even more preferably at least 99.5%. For example, an enantiomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 90% by weight of one stereoisomer of the compound and less than about 10% by weight of other stereoisomers of the compound, more preferably greater than about 95% by weight of one stereoisomer of the compound and less than about 5% by weight of the other stereoisomers of the compound, even more preferably greater than about 98% by weight of one stereoisomer of the compound and less than about 2% by weight of the other stereoisomers of the compound, and most preferably greater than about 99% by weight of one stereoisomer of the compound and less than about 1% by weight of the other stereoisomers of the compound.

The symbol ''''''' (dashed bond) present in some of the formulae of the description and/or the claims indicates that the substituent is directed below the plane of the sheet.

The symbol ━━ (wedge bond) present in some of the formulae of the description and/or the claims indicates that the substituent is directed above the plane of the sheet.

As used herein, the term "oxygen protecting group" refers to a group that may be attached to an oxygen atom to protect it from participating in the reaction and that may be readily removed following the reaction. Suitable oxygen protecting groups include ethers (in which the oxygen atom is linked to a group of formula —R wherein R is, e.g., methyl, methoxymethyl, methylthiomethyl, benzyloxymethyl, p-methoxybenzyloxymethyl, p-nitrobenzyloxymethyl, o-nitrobenzyloxymethyl, (4-methoxyphenoxy)methyl, tert-butoxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, tetrahydrofuranyl, 1-ethoxyethyl, tert-butyl, allyl, p-chlorophenyl, p-methoxyphenyl, p-nitrophenyl, 2,4-dinitrophenyl, benzyl, p-methoxybenzyl, 3,4-dimethoxybenzyl, p-nitrobenzyl, 2,6-difluorobenzyl); silyl ethers (in which the oxygen atom is linked to a group of formula —Si—(R')$_3$ wherein each R', independently of each other, is, e.g., methyl, ethyl, isopropyl, tert-butyl, phenyl, benzyl, methoxy); esters (in which the oxygen atom is linked to a group of formula —C(O)—R", wherein R" is for example methyl, dichloromethyl, trichloromethyl, trifluoromethyl, methoxymethyl, phenoxymethyl, benzyl, diphenylmethyl, phenyl); carbonates (in which the oxygen atom is linked to a group of formula —C(O)—OR''', wherein R''' is for example methyl, ethyl, methoxymethyl, allyl, p-nitrophenyl, benzyl, p-methoxybenzyl, 3,4-dimethoxybenzyl, p-nitrobenzyl, o-nitrobenzyl).

The term "mass" defines the combination of substrates, reagents, solvents, and products on which a physical or chemical transformation is carried out.

As used herein, the term "nitrogen protecting agent" refers to a compound which is reacted with an amino group so as to protect it from participating to the reaction. Exemplary nitrogen protecting agents are conventionally used in chemistry and generally known in the field, e.g. from Theodora W. Green, *Protective Groups in Organic Synthesis*, John Wiley & Sons (1999).

As used herein, the term "nitrogen protecting group" refers to a group that may be attached to a nitrogen atom to protect it from participating in the reaction and that may be readily removed following the reaction. Suitable nitrogen protecting groups include carbamates (in which the nitrogen atom is linked to a group of formula —C(O)OR$_a$' wherein R$_a$' is, e.g., (C1-C6)alkyl- (preferably methyl, ethyl, tert-butyl), aryl(C1-C6)alkyl- (preferably benzyl, phenylethyl), CH$_2$=CH—CH$_2$—, wherein the aryl and the alkyl group can be further substituted with at least one group selected from the group consisting of OH, CN, NO$_2$, CO$_2$H, halogen, (C1-C6)alkyl, (C1-C6)alkoxy-, and (C1-C6)alkoxycarbonyl-); amides (in which the nitrogen atom is linked to a group of formula —C(O)—R$_a$", wherein R$_a$" is for example (C1-C6)alkyl (preferably methyl), aryl (preferably (C6-C10) aryl, more preferably phenyl), wherein the aryl and the alkyl group can be further substituted with at least one group selected from the group consisting of OH, CN, NO$_2$, CO$_2$H, halogen, (C1-C6)alkyl, (C1-C6)alkoxy-, and (C1-C6) alkoxycarbonyl-; N-sulfonyl derivatives (in which the nitrogen atom is linked to a group of formula —SO$_2$—R$_a$''', wherein R$_a$''' is, e.g., (C1-C6)alkyl or aryl (preferably (C6-C10)aryl, more preferably phenyl), wherein the aryl and the alkyl group can be further substituted with at least one group selected from the group consisting of OH, CN, NO$_2$, CO$_2$H, halogen, (C1-C6)alkyl, (C1-C6)alkoxy-, and (C1-C6) alkoxycarbonyl-.

The amidoxime functional group present in the compounds of formulae (5), (5A), (5B), (5C), (5A1), (5'), (5A'), (5B'), (6'), (6'A), (6'B), (6'C), (6A1), (6''), (6A''), (6B'') may exist in one of the following tautomeric structures (B), (C), (B') or (C'):

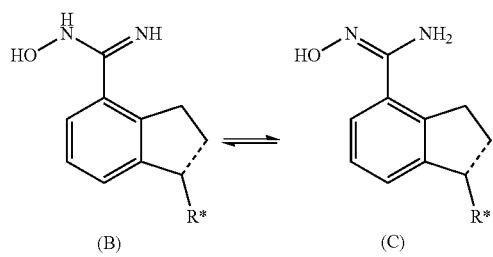

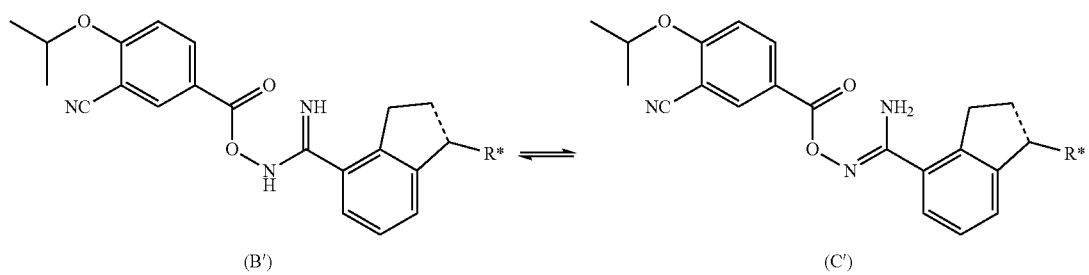

in which:

in the compounds of formulae (5), (5A), (5B), (5C), (5A1), (5'), (5A'), (5B'), R* is independently selected from $N_3$, $-N(R^{16})CH_2CH_2OR^{13}$, and $-N(R^{16})CH_2R^{14}$ or forms together with the carbon atom to which it is bonded a cyclic ketal, a ketal or an enol ether, with the proviso that when the dashed line indicates a double bond, R*, together with the carbon atom to which it is linked, forms an enol ether;

in the compounds of formulae (6'), (6'A), (6'B), (6'C), (6A1), (6"), (6A"), (6B"), R* is independently selected from $N_3$, $-N(R^{16})CH_2R^{10}$, $-N(R^{16})CH_2CH_2OR^{13}$, and $-N(R^{16})CH_2R^{14}$ or forms together with the carbon atom to which it is bonded a cyclic ketal, a ketal or an enol ether, with the proviso that when the dashed line indicates a double bond, R*, together with the carbon atom to which it is linked, forms an enol ether.

The compounds obtained by the chemical transformations of the present invention can be used without further purification or can be separated and purified by employing conventional methods well known to those skilled in the art, such as crystallization, column chromatography, or by transforming them into a salt or into a co-crystal with an appropriate co-former, or by washing with an organic solvent or with an aqueous solution, optionally adjusting pH.

It will be understood that any one of the compounds described herein also refer to salts or co-crystals thereof.

According to a first aspect thereof, the present invention relates to a process for the preparation of a compound of general formula (7) or a salt thereof, said process comprising:

a) reacting an indanone of general formula (1) with a compound of general formula (2) so as to provide a compound of general formula (3);

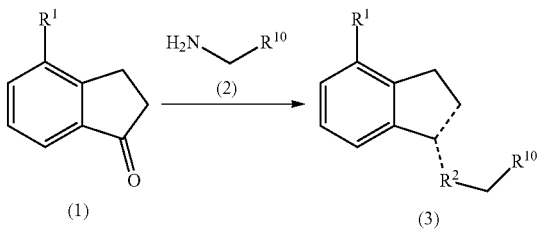

b) converting said compound of general formula (3) into a compound of general formula (7) or a salt thereof;

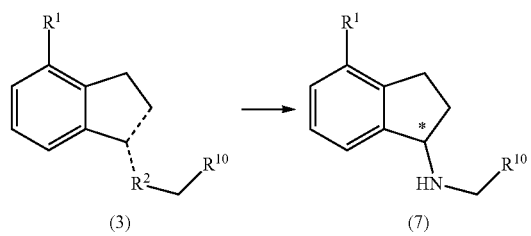

wherein:
$R^1$ is selected from the group consisting of —CN and 1,2,4-oxadiazole, said 1,2,4-oxadiazole being attached to the bicycle via carbon 3 and optionally substituted in position 5 with a 3'-cyano-4'-isopropoxyphenyl group;
one of the dashed lines indicate a single bond and the other one a double bond;
when the dashed line linked to $R^2$ is a double bond, $R^2$ is N, and when the dashed line linked to $R^2$ is a single bond, $R^2$ is NH;
$R^{10}$ is selected from the group consisting of —CH$_2$OH, —CH$_2$OPg and —CO$_2R^{12}$;
$R^{12}$ is selected from the group consisting of H and linear or branched (C1-C8)alkyl-optionally substituted with a (C6-C10)aryl-; and Pg is an oxygen protecting group;
said process being characterized in that step a) is carried out in the absence of titanium alkoxides.

Step a), object of the first aspect of the invention, comprises the reaction of an indanone of general formula (1) with a compound of general formula (2), in the absence of titanium alkoxides (preferably in the absence of titanium-based Lewis acids, more preferably in the absence of metal-based Lewis acids).

Compounds of general formula (2) suitable to be used in step a) are commercially available; alternatively, they can be prepared according to standard techniques in organic synthesis. According to a preferred embodiment of this aspect of the invention, an indanone of formula (1') (i.e. an indanone of general formula (1) in which $R^1$ is —CN) or an indanone of formula (1") (i.e. an indanone of general formula (1) in which $R^1$ is a 1,2,4-oxadiazole attached to the bicycle via carbon 3 and substituted in position 5 with a 3'-cyano-4'-isopropoxyphenyl group) is used as a reactant to perform this step.

The indanone of formula (1') is commercially available; alternatively, it can be prepared according to standard techniques in organic synthesis, for example, using the procedure described in the international application WO 2011/060392 A1.

The indanone of formula (1''') can be conveniently prepared according to the following steps:

c) providing a protected indanone of formula (4):

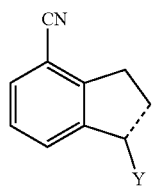

(4)

d) treating said protected indanone of formula (4) with hydroxylamine or a salt thereof so as to provide an amidoxime of formula (5), a tautomer or a salt thereof:

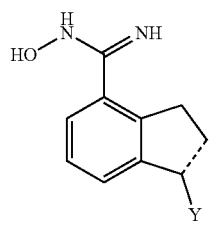

(5)

e) converting said amidoxime of formula (5), the tautomer or the salt thereof into a protected indanone of formula (6):

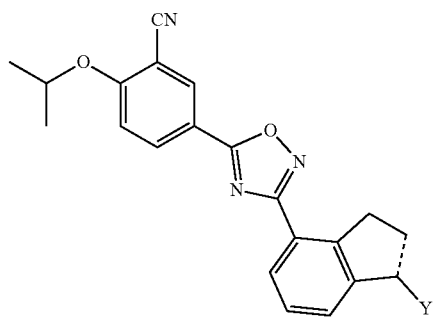

(6)

f) converting said protected indanone of formula (6) into an indanone of formula (1"):

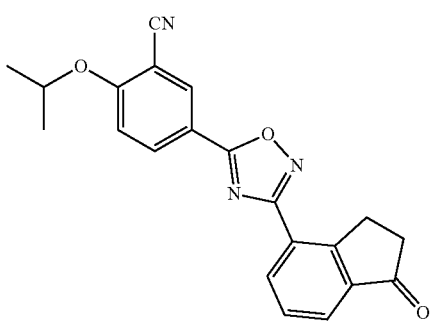

(1")

in which:
Y, together with the carbon atom to which it is bonded, forms a cyclic ketal, a ketal or an enol ether; and
the dashed line indicates a single or a double bond;
with the proviso that when the dashed line indicates a double bond, Y, together with the carbon atom to which it is linked, forms an enol ether.

Step c) comprises the provision of a 1-protected indanone of formula (4). Preferably this step comprises contacting the indanone of formula (1') with an agent capable of forming a cyclic ketal, a ketal, or an enol ether so that a protected indanone of formula (4) is formed. According to a first embodiment of this aspect of the invention, the protected indanone of formula (4) is a cyclic ketal of formula (4A):

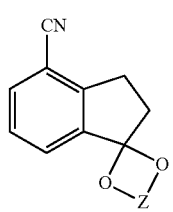

(4A)

in which:
Z is $(CR^3R^4)_n$;
n is 2 or 3; and
$R^3$ and $R^4$ are, independently of each other, hydrogen or a linear or branched (C1-C6)alkyl.

To form the cyclic ketal of formula (4A), the indanone of formula (1') may be contacted with a diol optionally in the presence of a proton donor and/or a dehydrating agent. In general, the diol comprises from 2 to 6 carbon atoms. Non-limiting examples of suitable diols include ethanediol, propanediol, butanediol, pentanediol, and hexanediol. Preferably, the diol is ethylene glycol (i.e., ethane-1,2-diol), propylene glycol (i.e., propane1,2-diol) or, more preferably neopentyl glycol (i.e., 2,2-dimethylpropane-1,3-diol).

The molar ratio of the indanone of formula (1') to the diol is conveniently from 1:0.5 to 1:20. Preferably the molar ratio of the indanone of formula (1') to the diol is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:8, 1:10 or 1:15.

A variety of proton donors are suitable for use in this step. In general, the proton donor has a pKa of less than 0. Non-limiting examples of proton donors having this characteristic include hydrogen halides (e.g., hydrochloric acid (HCl), hydrobromic acid (HBr), hydroiodic acid (HI)); halogen oxoacids (e.g., chloric acid (HClO$_3$), perchloric acid (HClO$_4$), and the corresponding compounds for bromine and iodine); sulfuric acid (H$_2$SO$_4$); fluoroantimonic acid; fluoroboric acid; hexafluorophosphoric acid; boric acid; and sulfonic acids (e.g., methanesulfonic acid, ethanesulfonic acid, benzenesulfonic acid; p-toluenesulfonic acid, trifluoromethanesulfonic acid, camphorsulfonic acid). Preferably, the proton donor is p-toluenesulfonic acid.

Dehydrating agents suitable for the aim are for example selected from esters of orthoformic acid (preferably trimethyl orthoformate, triethyl orthoformate and triisopropyl orthoformate), dehydrating salts (preferably magnesium sulfate or sodium sulfate) and molecular sieves. Preferably this step is carried out in the presence of both a proton donor (preferably p-toluenesulfonic acid) and a dehydrating agent (preferably trimethyl orthoformate or triethyl orthoformate).

The molar ratio of the indanone of general formula (1) to the dehydrating agent may vary in a very wide range. Preferably, the molar ratio of the indanone (1) to the dehydrating agent is from 1:0.5 to 1:10. More preferably, the molar ratio of the indanone (1) to the dehydrating agent is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:7, 1:8, or 1:9.

The molar ratio of the indanone of formula (1') to the proton donor may vary in a very wide range. Preferably, the molar ratio of the indanone of formula (1') to the proton donor is from 1:0.01 to 1:10. More preferably, the molar ratio of the indanone of formula (1') to the proton donor is between and optionally includes any two of the following values: 1:0.02, 1:0.05, 1:0.07, 1:0.1, 1:0.12, 1:0.15, 1:0.18, 1:0.2, 1:0.5, 1:1, 1:2, 1:5, 1:6, 1:7, 1:8, 1:9 or 1:10.

According to a second embodiment of this aspect of the invention, the protected indanone of formula (4) is a ketal of formula (4B):

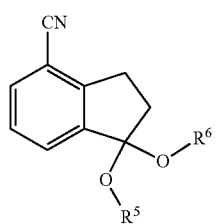

(4B)

in which R$^5$ and R$^6$ are, independently of each other, a linear or branched (C1-C8)alkyl-.

To form the ketal of formula (4B), the indanone of formula (1') may be contacted with at least one alcohol comprising from 1 to 8 carbon atoms optionally in the presence of a proton donor and/or a dehydrating agent. Suitable alcohols include methanol, ethanol, n-propanol, iso-propanol, n-butanol, iso-butanol, tert-butanol, pentanol, or mixtures thereof.

The molar ratio of the indanone of formula (1') to the at least one alcohol is conveniently from 1:0.5 to 1:20. Preferably the molar ratio of the indanone of formula (1') to the at least one alcohol is between and optionally includes any two of the following values: 1:0.6, 1:0.7, 1:0.8, 1:0.9, 1:1, 1:2, 1:3, 1:4, 1:5, 1:6, 1:8, 1:10 or 1:15.

A variety of proton donor may be used to prepare the ketal of formula (4B). In general, the proton donor may have a pKa of less than about 0. Suitable proton donors are, for example, those listed above in connection with the preparation of the cyclic ketal of formula (4A).

The molar ratio of the indanone of formula (1') to the proton donor may vary in a very wide range. Preferably, the molar ratio of the indanone of formula (1') to the proton donor is from 1:0.01 to 1:10. More preferably, the molar ratio of the indanone of formula (1') to the proton donor is between and optionally includes any two of the following values: 1:0.02, 1:0.05, 1:0.07, 1:0.1, 1:0.12, 1:0.15, 1:0.18, 1:0.2, 1:0.5, 1:1, 1:2, 1:5, 1:6, 1:7, 1:8, 1:9 or 1:10.

Dehydrating agents suitable for the aim are for example selected from esters of orthoformic acid (preferably trimethyl orthoformate, triethyl orthoformate and triisopropyl orthoformate), dehydrating salts (preferably magnesium sulfate or sodium sulfate) and molecular sieves. The molar ratio of the indanone of general formula (1) to the dehydrating agent may vary in a very wide range. Preferably, the molar ratio of the indanone (1) to the dehydrating agent is from 1:0.5 to 1:10. More preferably, the molar ratio of the indanone (1) to the dehydrating agent is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:7, 1:8, or 1:9.

According to a third embodiment of this aspect of the invention, the protected indanone of formula (4) is an enol ether of formula (4C):

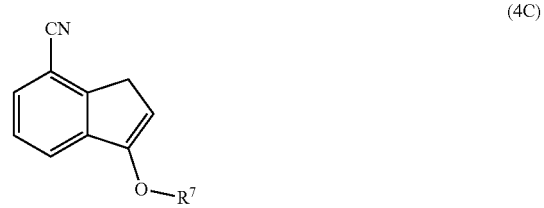

(4C)

in which:
R$^7$ is selected from the group consisting of a linear or branched (C1-C8)alkyl- optionally substituted with a (C6-C10)aryl-, R$^8$C(O)— (preferably CH$_3$C(O)—) and (R$^9$)$_3$Si— (preferably (CH$_3$)$_3$Si—, (t-Bu)Me$_2$Si— and (t-Bu)Ph$_2$Si);
R$^8$, and R$^9$ are, independently of each other, a linear or branched (C1-C8)alkyl- optionally substituted with a (C6-C10)aryl-.

The indanone of formula (1') can be converted into the enol ether of formula (4C) by treatment with an acylating agent (preferably acetic anhydride), a silylating agent (preferably trimethylsilyl chloride, tert-butyldimethylsilyl chloride and tert-butyldiphenylsilyl chloride) normally in the presence of a base, either organic or inorganic, preferably a tertiary amine, optionally in an inert solvent such as dichloromethane or toluene.

Alternatively, when $R^7$ is a linear or branched (C1-C8) alkyl- optionally substituted with a (C6-C10)aryl-, the enol ether of formula (4C) may be formed by contacting the indanone of formula (1') with an alcohol optionally in the presence of a proton donor and/or a dehydrating agent (preferably according to a procedure equivalent to those detailed above in respect of the ketal of formula (4B)) followed by distillation of the alcohol. Those of ordinary skill in the art are familiar with suitable distillation techniques.

As another option, the enol ether of formula (4C) may be formed by contacting the indanone of formula (1') with a proton acceptor and a dialkyl sulfate. A variety of proton acceptors are suitable for use in the preparation of the enol ether of formula (4C). In general, the proton acceptor has a pKa greater than 13, or more preferably greater than 20. Non-limiting examples of suitable proton acceptors having this characteristic include hydroxides of alkali metals and alkaline earth metals (such as, for example, NaOH and $Ca(OH)_2$), as well as group 1 salts of carbanions, alkyl amides, and hydrides (such as, for example, butyllithium, lithium methylamide, lithium isopropylamide, sodium hydride).

The amount of proton acceptor used in this step may vary very widely. In general, the molar ratio of the indanone of formula (1') to the proton acceptor may range from 1:1 to 1:3. In certain embodiments, the molar ratio of the indanone of formula (1') to the proton acceptor may be between and optionally includes any two of the following values: 1:1.2, 1:1.4, 1:1.5, 1:1.6, 1:1.8, 1:2, 1:2.2, 1:2.4, 1:2.6 or 1:2.8.

Dialkyl sulfates suitable for the aim include, for example, dimethyl sulfate, diethyl sulfate, dipropyl sulfate, diisopropyl sulfate, dibutyl sulfate, dipentyl sulfate, and dibenzyl sulfate.

The molar ratio of the indanone of formula (1') to the dialkyl sulfate may range from 1:1 to 1:3. Preferably, the molar ratio of the indanone of formula (1') to the dialkyl sulfate is between and optionally includes any two of the following values: 1:1.2, 1:1.4, 1:1.6, 1:1.8, 1:2, 1:2.2, 1:2.4, 1:2.6 or 1:2.8.

Step c) of the process of the invention is normally performed in the presence of a solvent. Suitable solvents include nonpolar solvents, aprotic polar solvents, polar protic solvents, and combinations thereof. Non-limiting examples of suitable nonpolar solvents include benzene, toluene, tert-butyl methyl ether, chlorobenzene, chloroform, cyclohexane, dichloromethane, dichloroethane, di-tert-butyl ether, diethyl ether, diglyme, diisopropyl ether, ethylene oxide, fluorobenzene, heptane, hexane, and combinations thereof. Suitable aprotic solvents include, for example, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl acetate, ethyl formate, formamide, hexachloroacetone, hexamethylphosphoramide, methyl acetate, N-methylacetamide, N-methylformamide, methoxyethane, morpholine, nitrobenzene, nitromethane, propionitrile, propyl acetate, butyl acetate, sulfolane, tetramethylurea, tetrahydrofuran (THF), 2-methyl tetrahydrofuran, tetrahydropyran, trichloromethane, and combinations thereof. Polar protic solvents suitable for the aim include, e.g., alcohols such as methanol, ethanol, n-propanol, iso-propanol, n-butanol, iso-butanol, tert-butanol, pentanol, or mixtures thereof. In a preferred embodiment, the solvent is toluene, benzene, iso-propanol or a mixture thereof.

The volume of the solvent is normally from 1 mL to 50 mL per gram of the indanone of formula (1'). Preferably the volume of the solvent is between and optionally includes any two of the following values: 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL or 45 mL per gram of the indanone of formula (1'). More preferably said volume is from 3 mL to 8 mL per gram of the indanone of formula (1').

The treatment of said protected indanone of formula (4) (preferably the cyclic ketal of formula (4A), the ketal of formula (4B), or the enol ether of formula (4C)) with hydroxylamine or a salt thereof so as to provide an amidoxime of formula (5) a tautomer or a salt thereof, according to step d), can be preferably accomplished in at least one solvent, preferably an organic solvent, more preferably an alcohol (e.g., methanol, ethanol, isopropanol and tert-butanol), a polar aprotic solvent (e.g. dimethylformamide, dimethylacetamide) or a mixture thereof. More preferably step d) is carried out in a mixture of solvents comprising an organic solvent miscible with water (e.g. an alcohol) and water.

Step d) is conveniently carried out at a temperature from 0 to the reflux temperature of the solvent used, more preferably from 20 to 50° C. (e.g., the temperature is between and optionally includes any two of the following values: 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C. or 49° C.).

The volume of the solvent is normally from 1 mL to 50 mL per gram of the protected indanone of formula (4). Preferably, the volume of the solvent is between and optionally includes any two of the following values: 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL or 45 mL per gram of the protected indanone of formula (4).

The ratio between the solvents in said mixtures can vary in a very wide range; preferably when a mixture comprising an alcohol and water is used, said ratio is from 500:1 to 100:1 (V/V), more preferably from 400:1 to 150:1 (V/V), even more preferably from 300:1 to 200:1 (V/V).

Preferably step d) is carried out in the presence of a base when a salt of hydroxylamine.

The molar ratio of the protected indanone of formula (4) to the hydroxylamine or the salt thereof (preferably a hydrochloride salt thereof), may range from 1:1 to 1:10. In certain embodiments, the molar ratio of the protected indanone of formula (4) to the hydroxylamine or the salt thereof may be between and optionally includes any two of the following values: 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

The base optionally used in step d) is preferably a tertiary amine (cyclic or acyclic, such as triethylamine, N,N-diisopropylethylamine, N,N-diisopropylmethylamine, N-methylpyrrolidine, N-methylmorpholine, N,N-dicyclohexylmethylamine, N,N-diethylaniline, pyridine, 2-methylpyridine, 2,6-dimethylpyridine, 2,4,6-trimethylpyridine, 4-dimethylaminopyridine), or an alkoxide (preferably methoxide, ethoxide or tert-butoxide) of sodium, lithium or potassium.

The molar ratio of the hydroxylamine salt to the base, when used, may conveniently range from 1:1 to 1:5. In certain embodiments, the molar ratio of the hydroxylamine salt to the base may be between and optionally includes any two of the following values: 1:1.1, 1:1.2, 1:1.3, 1:1.4, 1:1.5, 1:1.6, 1:1.7, 1:1.8, 1:1.9, 1:2, 1:2.5, 1:3, 1:3.5, 1:4, or 1:4.5.

According to a preferred embodiment of this aspect of the invention, step d) involves mixing a dispersion (preferably a suspension) comprising a hydroxylamine salt (preferably a hydrochloride salt thereof) with a base (preferably a tertiary amine or an alkoxide of sodium, lithium or potassium) and, subsequently, with the protected indanone of formula (4).

The amidoxime of formula (5), the tautomer or the salt thereof, is further converted into a protected indanone of formula (6) according to step e), for example, by treatment with a compound of formula (8):

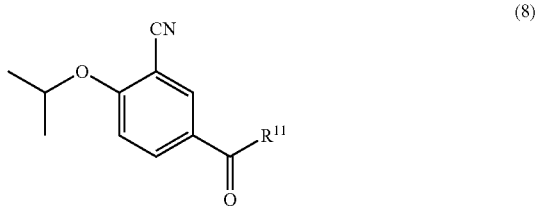

(8)

in which $R^{11}$ is selected from the group consisting of a linear or branched (C1-C6)alkoxy-, OH, imidazole and a halogen.

Preferably the amidoxime of formula (5), the tautomer or the salt thereof, is converted into a protected indanone of formula (6) by treatment with a compound of formula (8) in which $R^{11}$ is imidazole.

For example, when in the compound of formula (8) $R^{11}$ is (C1-C6)alkoxy, it can be reacted with the amidoxime of formula (5), the tautomer or the salt thereof, in the presence of a solvent at a temperature normally from 25° C. to the reflux temperature of the solvent used. Alternatively, when in the compound of formula (8) $R^{11}$ is (C1-C6)alkoxy-, it can be hydrolysed to the corresponding carboxylic acid according to known methods, for example by reaction with a base such as sodium hydroxide, lithium hydroxide or potassium hydroxide, or by reaction with an acid, e.g. hydrogen chloride optionally dissolved in an organic solvent, hydrochloric acid or sulfuric acid. Said carboxylic acid can be further reacted with the amidoxime of formula (5), the tautomer or the salt thereof, in the presence of a coupling agent such as 1-ethyl-3-(3-dimethylaminopropyl)carbodiimide (EDCI), benzotriazol-1-yl-oxytripyrrolidinophosphonium hexafluorophosphate (PyBOP), bromotripyrrolidinophosphonium hexafluorophosphate (PyBroP), 1,1'-carbonyldiimidazole (CDI), 1-propanephosphonic anhydride (T3P), isobutyl chloroformate (IBCF), N,N,N',N'-tetramethylchloroformamidinium hexafluorophosphate (TCFH), N-ethoxycarbonyl-2-ethoxy-1,2-dihydroquinoline (EEDQ) or N,N'-dicyclohexylcarbodiimide (DCC), optionally in the presence of an organic base such as triethylamine, N,N-diisopropylethylamine or pyridine. This step is preferably carried out in an organic solvent such as tetrahydrofuran, 2-methyl tetrahydrofuran, cyclopentyl methyl ether, dioxane, or N,N-dimethylformamide. Said carboxylic acids can be, alternatively, reacted with a source of chlorine, such as thionyl chloride ($SOCl_2$), phosphorus trichloride ($PCl_3$), phosphorus pentachloride ($PCl_5$), oxalyl chloride (($COCl)_2$), in an organic solvent, preferably a chlorinated solvent such as dichloromethane, at a temperature from 35° C. to 60° C. to yield the corresponding acyl chloride, which is further reacted with the amidoxime of formula (5), the tautomer or the salt thereof, preferably in the presence of a base, so as to provide a protected indanone of formula (6).

As another option, when in the compound of formula (8) $R^{11}$ is imidazole, it can be reacted with the amidoxime of formula (5), the tautomer or the salt thereof, in the presence of a solvent, preferably an ether (more preferably tetrahydrofuran, 2-methyltetrahydrofuran, cyclopentyl methyl ether), an aromatic hydrocarbon (e.g. toluene) or a polar aprotic solvent (e.g. dimethylformamide, dimethylacetamide) or a mixture thereof. Preferably this operation is carried out at a temperature from 25° C. to the reflux temperature of the solvent used, preferably from 40° C. to 110° C., more preferably from 55° C. to 85° C.

Alternatively, when in the compound of formula (8) $R^{11}$ is a halogen, it can be reacted with the amidoxime of formula (5), the tautomer or the salt thereof, in a suitable solvent, at a temperature normally from −25° C. to 40° C. and optionally in the presence of at least one base, either inorganic or organic, preferably a tertiary amine (cyclic or acyclic), such as triethylamine, N,N-diisopropylethylamine, N,N-diisopropylmethylamine, N-methylpyrrolidine, N-methylmorpholine, N,N-dicyclohexylmethylamine, N,N-diethylaniline, pyridine, 2-methylpyridine, 2,6-dimethylpyridine, 2,4,6-trimethylpyridine or 4-dimethylaminopyridine.

The molar ratio of the amidoxime of formula (5), the tautomer or the salt thereof, to the compound of formula (8) may normally range from 1:1 to 1:10. In certain embodiments, the molar ratio of the amidoxime of formula (5) to the compound of formula (8) may be between and optionally includes any two of the following values: 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

The molar ratio of the protected amidoxime of formula (5), the tautomer or the salt thereof, to the coupling agent may conveniently range from 1:1 to 1:10. In certain embodiments, the molar ratio of the amidoxime of formula (5), the tautomer or the salt thereof, to the coupling agent may be between and optionally includes any two of the following values: 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

The volume of the solvent optionally used in step e) is normally from 1 mL to 50 mL per gram of the amidoxime of formula (5), the tautomer or the salt thereof. Preferably, the volume of the solvent is between and optionally includes any two of the following values: 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL per gram of the amidoxime of formula (5), the tautomer or the salt thereof.

A variant of the process object of this aspect of the invention includes an additional and optional step e'), carried out after step e), comprising heating the mixture resulting from step e) (namely the mass resulting from the reaction between the compound of formula (8) and an amidoxime of formula (5), (5A), (5B) or (5C), a tautomer or a salt of any one of them) preferably a mass comprising a compound of general formula (6'), a salt or a tautomer thereof, more preferably a mass comprising a compound of general formula (6'A), (6'B) or (6'C), a tautomer or a salt of any one of them, to a temperature from 50° C. to 120° C. so as to increase the rate of conversion into the protected indanone of formula (6).

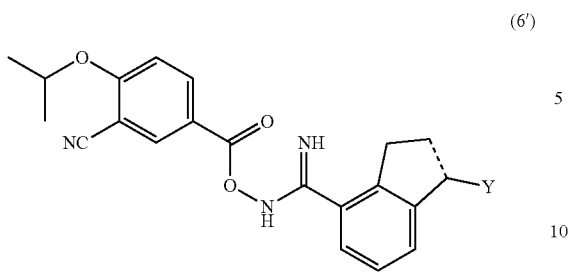 (6')

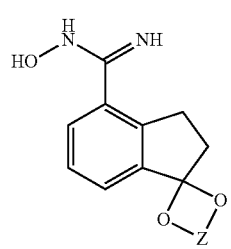 (5A)

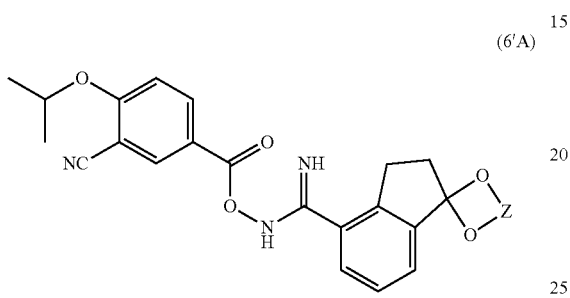 (6'A)

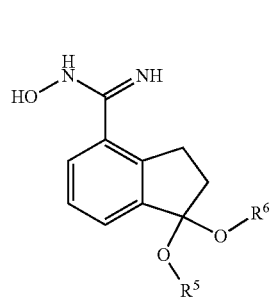 (5B)

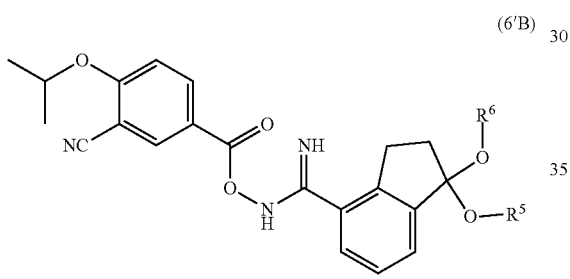 (6'B)

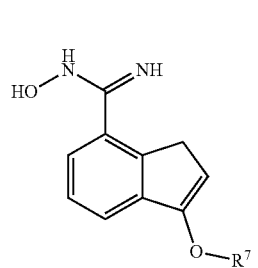 (5C)

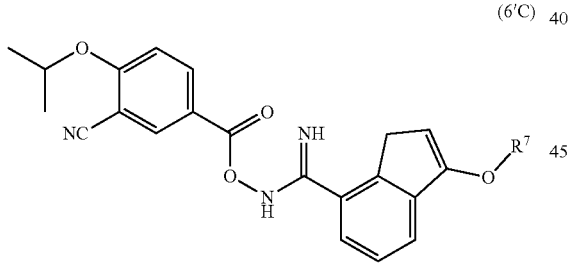 (6'C)

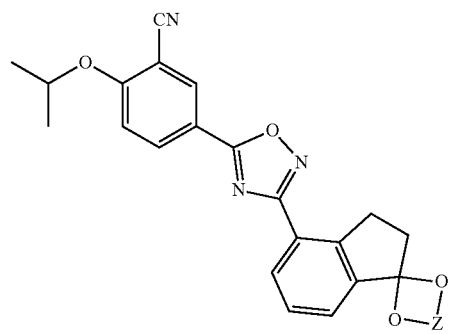 (6A)

wherein the substituents assume the meanings reported above.

According to a preferred embodiment of this aspect of the invention, step e) is carried out by mixing the compound of formula (8) with an ether (preferably tetrahydrofuran, 2-methyl tetrahydrofuran, cyclopentyl methyl ether), a coupling agent (preferably 1,1'-carbonyldiimidazole (CDI) or 1-propanephosphonic anhydride (T3P)) and, subsequently, with the amidoxime of formula (5), the tautomer or the salt thereof.

According to a more preferred embodiment of this aspect of the invention, step e) or e') leads, depending upon the starting amidoxime of formula (5A), (5B) or (5C), the tautomer or the salt thereof, to the protected indanone of formula (6A), (6B) or (6C):

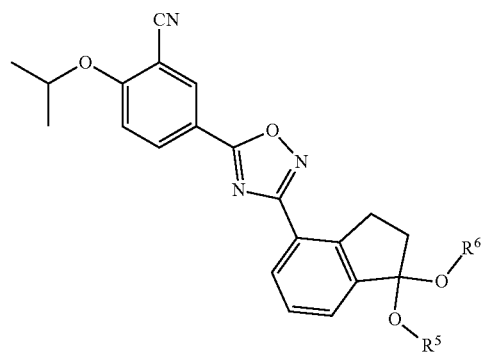 (6B)

-continued (6C)

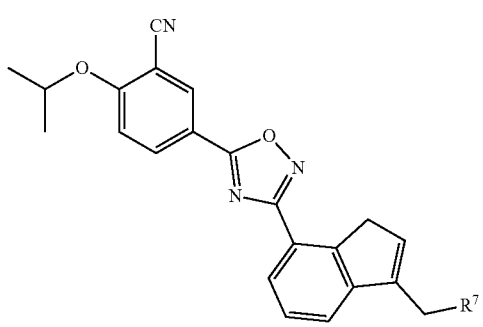

wherein the substituents assume the meanings reported above.

The following step f) comprises converting said protected indanone of formula (6), preferably a protected indanone of formula (6A), (6B) or (6C), into an indanone of formula (1″) by treatment with at least one proton donor.

A variety of proton donors are suitable for use in this reaction. In general, the proton donor may have a pKa of less than 0, or more preferably of less than −2. Non-limiting examples of proton donors having this characteristic include hydrogen halides (e.g., hydrochloric acid (HCl), hydrobromic acid (HBr), hydroiodic acid (HI), and the like); halogen oxoacids (e.g., chloric acid ($HClO_3$), perchloric acid ($HClO_4$), and corresponding compounds for bromine and iodine); sulfuric acid ($H_2SO_4$); fluoroantimonic acid; fluoroboric acid; hexafluorophosphoric acid; boric acid; and sulfonic acids (e.g., methanesulfonic acid, ethanesulfonic acid, benzenesulfonic acid, p-toluenesulfonic acid, camphorsulfonic acid or trifluoromethanesulfonic acid). In a preferred embodiment, the proton donor is p-toluenesulfonic acid.

The molar ratio of the protected indanone of formula (6) to the proton donor may vary in a very wide range. Preferably, the molar ratio of the protected indanone of formula (6) to the proton donor is from 1:0.01 to 1:10. More preferably, the molar ratio of the protected indanone of formula (6) to the proton donor is between and optionally includes any two of the following values: 1:0.02, 1:0.05, 1:0.07, 1:0.1, 1:0.12, 1:0.15, 1:0.18, 1:0.2, 1:0.5, 1:1, 1:2, 1:5, 1:6, 1:7, 1:8 or 1:9.

Contact with the proton donor may be performed in the presence of a solvent. Suitable solvents are detailed above in respect of step c). Preferably this step is carried out in a ketone (more preferably acetone, 2-butanone or 3-pentanone) or a mixture thereof with an ether (preferably cyclopentyl methyl ether). The reaction may be conducted at a temperature from 10° C. to 80° C., e.g., at a temperature between and optionally including any two of the following values: 15° C., 20° C., 25° C., 30° C., 35° C., 40° C., 45° C., 50° C., 55° C., 60° C., 65° C., 70° C. or 75° C. In preferred embodiments, the reaction is performed at a temperature from 10° C. to 30° C.

Alternatively, when in the protected indanone of formula (6C) $R^7$ is $R^3C(O)$—, step f) involves a typical reaction of hydrolysis or deprotection of an enol ether, e.g. basic or acid hydrolysis. In the case when $R^7$ is $(R^9)_3Si$—, step f) comprises one of the hydrolytic conditions generally known in the field for its removal, e.g., in the case when $R^7$ is a sterically hindered silyl group such as tert-butyldimethylsilyl (TBDMS) or tert-butyldiphenylsilyl (TBDPS) by action of a fluoride ion (e.g. tetrabutylammonium fluoride) or of hydrogen fluoride.

According to another option, said indanone of formula (1″) can be prepared through oxidation of the alcohol of formula (1‴).

(1‴)

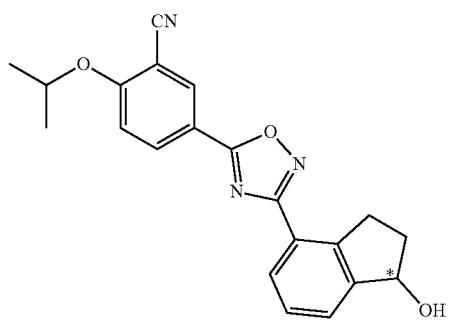

The alcohol of formula (1‴) is commercially available; alternatively, it can be prepared according to standard techniques in organic synthesis, for example, using the procedure described in the international application WO 2009/151529 A1.

Oxidizing conditions suitable for the aim are generally known and described, for example in S. D. Burke (Ed.), *Handbook of Reagents for Organic Synthesis, Oxidizing and Reducing Agents*, Wiley (1999, reprinted July 2005) page 1. Preferred oxidation conditions include:

employing the Swern oxidation (by treating with oxalyl chloride ($COCl)_2$ or trifluoroacetic anhydride (TFAA), dimethylsulfoxide (DMSO) and a tertiary amine) or one of its variation, such as the Corey-Kim oxidation (by treating with N-chlorosuccinimide, dimethyl sulfide and a tertiary amine) or the Pfitzner-Moffat oxidation (by treating with dicyclohexyl carbodiimide (DCC), DMSO and a catalytic amount of phosphoric acid);

using bis(acetoxy)iodobenzene and 2,6,6-tetramethylpiperidin-1-oxyl (TEMPO);

treating with hypervalent iodine based oxidizing agents such as 2-iodoxybenzoic acid (IBX) or Dess-Martin periodinane (DMP);

using a catalytic amount of tetrapropylammonium perruthenate (TPAP) with a co-oxidant such as N-methylmorpholine-N-oxide (NMO) (referred to as the Ley oxidation);

treating with TEMPO and sodium hypochlorite (NaOCl) optionally in the presence of sodium or potassium bromide (Anelli oxidation);

treating with trichloroisocyanuric acid optionally in the presence of TEMPO; or using dimethyl sulfoxide (DMSO) as the oxidant, activated by the sulfur trioxide pyridine complex in the presence of a tertiary amine (known as Parikh-Doering oxidation).

Step a) of the process object of the first aspect of the invention comprises reacting an indanone of general formula (1), preferably an indanone of formula (1') or (1″), with a compound of general formula (2), so as to provide a compound of general formula (3), preferably a compound of general formula (3A1), (3A2) or a mixture thereof, said step being performed in the absence of titanium alkoxides (preferably in the absence of titanium-based Lewis acids, more preferably in the absence of metal-based Lewis acids);

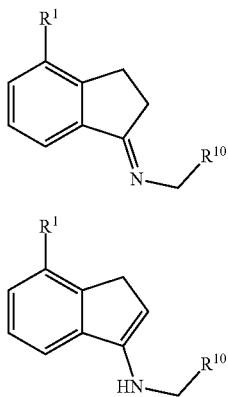

(3A1)

(3A2)

wherein the substituents assume the meanings reported above.

According to a first embodiment of this aspect of the invention, the compound of general formula (3) prepared according to step a) is a compound of general formula (3A):

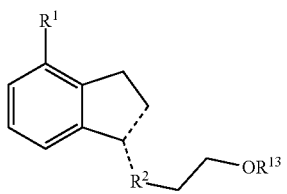

(3A)

in which the substituents and dashed lines assume the meanings reported above and $R^{13}$ is selected from the group consisting of H and Pg.

Preferably this step comprises contacting an indanone of general formula (1), more preferably an indanone of formula (1') or (1"), with a compound of general formula (2A) (i.e. a compound of general formula (2) in which $R^{10}$ is selected from the group consisting of —$CH_2OH$ and —$CH_2OPg$) and optionally with a proton donor, a dehydrating agent or a combination thereof so that a compound of general formula (3A) is formed.

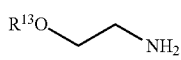

(2A)

The preparation of a compound of general formula (3A) can be conveniently carried out in a solvent or a mixture of solvents in which the indanone of general formula (1) is soluble and the compound of general formula (3A), product of the reaction, is insoluble, preferably in a solvent or a mixture of solvents in which the indanone is soluble and the compound of general formula (3A) is insoluble in the reaction conditions.

The inventors have surprisingly found that by selecting a solvent with these features it is possible to obtain excellent yields and high chemical purity of the desired product simply by filtering or decanting it from the reaction mixture.

Examples of solvents suitable for the aim are aromatic compounds (such as benzene, toluene and xylene), halogenated aromatic compounds (such as chlorobenzene); aliphatic hydrocarbon compounds (such as hexane and heptane), alcohols (preferably methanol, ethanol or isopropanol) or a mixture of said solvents. According to a preferred embodiment of this aspect of the invention, an alcohol (more preferably methanol, ethanol or isopropanol) or a mixture comprising an alcohol and an aromatic compound (more preferably benzene or toluene) is used in step a).

The volume of the solvent or of the mixture of solvents used in the preparation of compound of general formula (3A) is normally from 5 mL to 150 mL per gram of indanone (1). Preferably, the volume of the solvent is between and optionally includes any two of the following values: 10 mL, 15 mL, 20 mL, 25 mL, 30 mL, 35 mL, 40 mL, 45 mL, 50 mL, 55 mL, 60 mL, 65 mL, 70 mL, 75 mL, 80 mL, 85 mL, 90 mL, 95 mL, 100 mL, 105 mL, 110 mL, 115 mL, 120 mL, 125 mL, 130 mL, 135 mL, 140 mL or 145 mL per gram of indanone (1).

The ratio between the solvents in said mixtures can vary in a very wide range; preferably when a mixture comprising an aromatic compound and an alcohol is used, said ratio is from 3:1 to 20:1 (V/V), more preferably from 3.5:1 to 10:1 (V/V), even more preferably from 4:1 to 8:1 (V/V).

More preferably the preparation of compound of general formula (3A) is carried out in a solvent or a mixture of solvents having a boiling point lower than 120° C., preferably lower than 100° C., more preferably lower than 90° C., even more preferably lower than 85° C.

The use of a solvent or a mixture of solvents complying with this feature has the further advantageous effect of avoiding subtraction of 2-aminoethanol (i.e., a compound of general formula (2A) in which $R^{13}$ is H) from the reaction mixture so ensuring achievement of acceptable yields (i.e. at least 65%, preferably at least 70%, more preferably at least 75%, even more preferably at least 80%, most preferably at least 85%, said percentages being expressed on a molar basis) even when the molar ratio of the compound of general formula (2A) to the indanone of general formula (1) is lower than 10:1, preferably lower than 8:1, more preferably lower than 6:1, even more preferably lower than 5:1.

The molar ratio of the indanone of general formula (1) to the compound of general formula (2A) may vary in a very wide range. Preferably, the molar ratio of the indanone of general formula (1) to the compound of general formula (2) is from 1:1 to 1:10. More preferably, the molar ratio of the indanone (1) to the compound of general formula (2) is between and optionally includes any two of the following values: 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

Proton donors suitable for the aim are for example selected from those referred to above in respect of step c).

The molar ratio of the indanone of general formula (1) to the proton donor may vary in a very wide range. Preferably, the molar ratio of the indanone (1) to the proton donor is from 1:0.001 to 1:1. More preferably, the molar ratio of the indanone (1) to the proton donor is between and optionally includes any two of the following values: 1:0.002, 1:0.005, 1:0.007, 1:0.01, 1:0.015, 1:0.02, 1:0.03, 1:0.04, 1:0.05, 1:0.06, 1:0.07, 1:0.08, 1:0.09, 1:0.1, 1:0.2, 1:0.3, 1:0.4, 1:0.5, 1:0.6, 1:0.7, 1:0.8, or 1:0.9.

Dehydrating agents suitable for the aim are for example selected from esters of orthoformic acid (preferably trimethyl orthoformate, triethyl orthoformate and triisopropyl orthoformate), dehydrating salts (preferably magnesium sulfate or sodium sulfate) and molecular sieves. Preferably this step is carried out with concurrent removal of water, e.g. using a Dean-Stark trap or by azeotropic distillation.

The removal of water by azeotropic distillation or using a Dean-Stark trap, preferably a Dean-Stark condenser containing molecular sieves, has the advantageous effect of ensuring high recovery yields (i.e. at least 65%, preferably at least 70%, more preferably at least 75%, even more preferably at least 80%, said percentages being expressed on a molar basis) of the compound of general formula (3A).

The molar ratio of the indanone of general formula (1) to the dehydrating agent may vary in a very wide range. Preferably, the molar ratio of the indanone (1) to the dehydrating agent is from 1:0.5 to 1:10. More preferably, the molar ratio of the indanone (1) to the dehydrating agent is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:7, 1:8, or 1:9.

According to a second embodiment of this aspect of the invention, the compound of general formula (3) prepared according to step a) is a compound of general formula (3B):

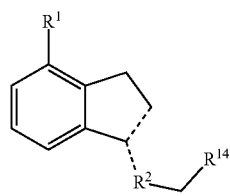

(3B)

in which the substituents and dashed lines assume the meaning reported above and $R^{14}$ is $-CO_2R^{12}$.

Preferably this step comprises contacting said indanone of general formula (1), more preferably an indanone of formula (1') or (1''), with a compound of general formula (2B) (i.e. a compound of general formula (2) in which $R^{10}$ is $R^{14}$) and optionally with a proton donor and/or a dehydrating agent so that the compound of general formula (3B) is formed.

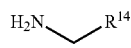

(2B)

This step can be performed using any one of the methods described above with respect to the compound of general formula (3A).

According to a more preferred embodiment of this aspect of the invention, step a) leads, depending upon the starting indanone of formula (1') or (11''), to a compound of general formula (3A'), (3A''), (3B'), (3B''), (3A'''), (3A''''), (3B''') or (3B''''):

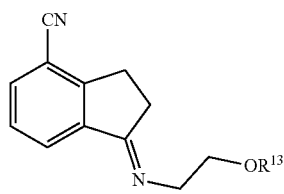

(3A')

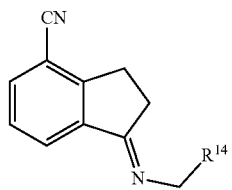

(3B')

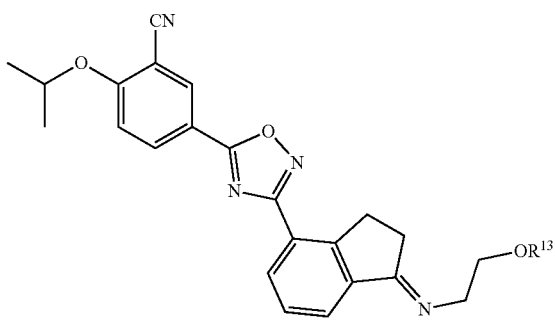

(3A'')

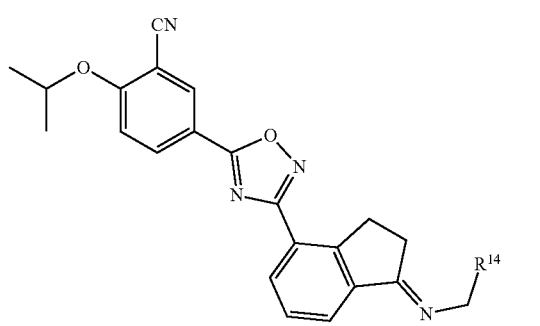

(3B'')

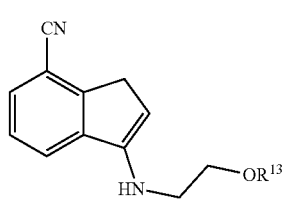

(3A''')

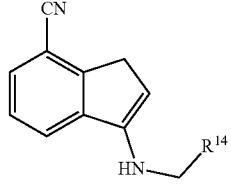

(3B''')

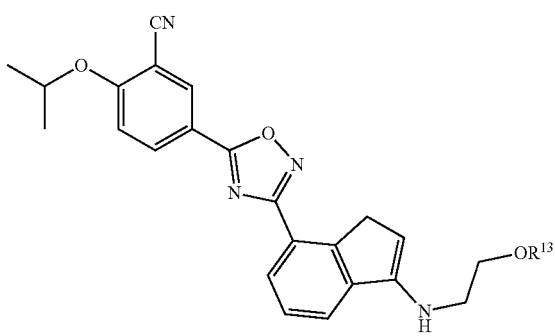

(3A'''')

(3B'''')

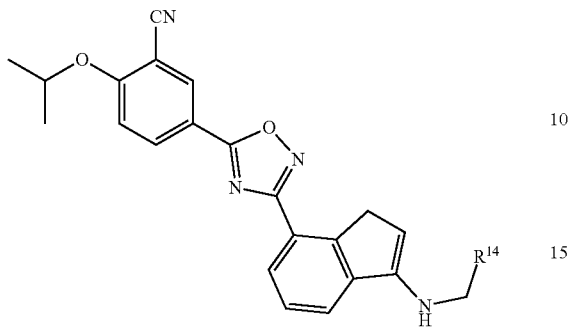

wherein the substituents assume the meanings reported above.

The thus obtained compound of general formula (3), preferably a compound of general formula (3A), (3B), (3A1) or (3A2), more preferably a compound of general formula (3A'), (3A''), (3B'), (3B''), (3A'''), (3A''''), (3B''') or (3B''''), optionally isolated, is then converted, according to step b) of the process, into a compound of general formula (7), preferably an enantiomerically enriched mixture thereof, more preferably an enantiomerically pure form thereof.

According to a first embodiment of this aspect of the invention, step b) is carried out by treating the compound of general formula (3), preferably a compound of general formula (3A), (3B), (3A1) or (3A2), more preferably a compound of general formula (3A'), (3A''), (3B'), (3B''), (3A'''), (3A''''), (3B''') or (3B''''), with a reducing agent so that a compound of formula (7), preferably a compound of general formula (7A'), (7A''), (7B') or (7B''), in the form of a racemic mixture is obtained.

(7A')

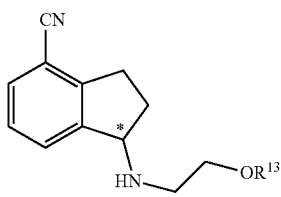

(7B')

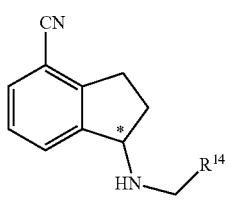

(7A'')

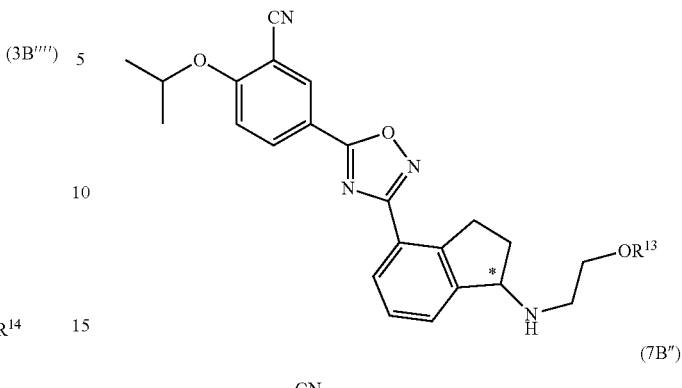

(7B'')

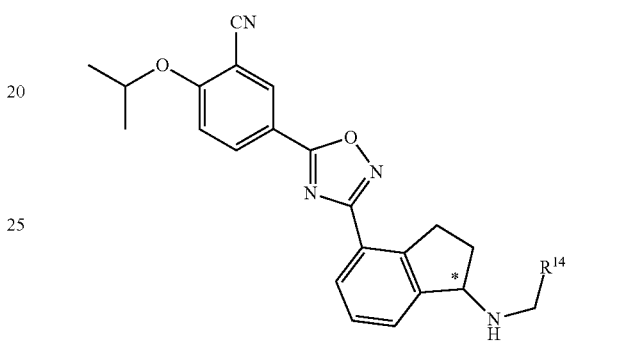

wherein the substituents assume the meanings reported above.

Reducing agents suitable for the purpose are generally known in the art and described, for example, in S. D. Burke (Ed.), *Handbook of Reagents for Organic Synthesis, Oxidizing and Reducing Agents*, Wiley (1999, reprinted July 2005) page 6; preferably, this step is carried out using as reducing agent a boron hydride (for example sodium, lithium or potassium borohydride or sodium triacetoxyborohydride), or borane complexed with a Lewis base, for example ammonia, an amine (primary, secondary or tertiary), a pyridine, a sulfide, a phosphine or an ether. Alternatively, the reducing agent can be selected from the group comprising aluminium hydrides (for example aluminium hydride, sodium, lithium or potassium aluminum hydride, diisobutylamlumium hydride and sodium, lithium or potassium tert-butoxyaluminium hydride). This step can be also conducted using as the reducing agent sodium dithionite ($Na_2S_2O_4$) or using hydrogen or a hydrogen source in the presence of a catalytic system comprising an achiral mono- or bidentate phosphine and at least one transition metal such as ruthenium, rhodium, iridium, nickel, palladium, platinum or salts thereof, said transition metal being optionally supported on an inert matrix such as carbon, silica or alumina or on an organic polymer matrix.

The molar ratio of the compound of general formula (3) to the reducing agent may vary in a very wide range. Preferably, the molar ratio of the compound of general formula (3) to the reducing agent is from 1:0.5 to 1:10. More preferably, the molar ratio of the compound of general formula (3) to the reducing agent is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:7, 1:8, or 1:9.

According to a second embodiment of this aspect of the invention, step b) involves a stereoselective reduction of the compound of general formula (3), preferably a compound of general formula (3A), (3B), (3A1) or (3A2), more preferably a compound of general formula (3A'), (3A"), (3B'), (3B"), (3A'''), (3A''''), (3B''') or (3B''''), so as to yield a compound of general formula (7), preferably a compound of general formula (7A'), (7A"), (7B') or (7B"), in enantiomerically enriched or enantiomerically pure form.

The stereoselective reduction of the compound of general formula (3), preferably a compound of general formula (3A), (3B), (3A1) or (3A2), more preferably a compound of general formula (3A'), (3A"), (3B'), (3B"), (3A'''), (3A''''), (3B''') or (3B''''), can be performed in the presence of at least one asymmetric hydrogenation catalysts and hydrogen donor.

Hydrogen donors include hydrogen, primary and secondary alcohols, primary and secondary amines, carboxylic acids and their esters and salts with amines, dehydrogenatable hydrocarbons, and any combination thereof.

Primary and secondary alcohols which may be employed as hydrogen donors comprise commonly from 1 to 10 carbon atoms, preferably from 2 to 7 carbon atoms, and more preferably 3 or 4 carbon atoms. Examples of primary and secondary alcohols which may be represented as hydrogen donors include methanol, ethanol, propan-1-ol, propan-2-ol, butan-1-ol, butan-2-ol, cyclopentanol, cyclohexanol, benzyl alcohol, and menthol. When the hydrogen donor is an alcohol, secondary alcohols are preferred, especially propan-2-ol and butan-2-ol.

Primary and secondary amines which may be employed as hydrogen donors comprise commonly from 1 to 20 carbon atoms, preferably from 2 to 14 carbon atoms, and more preferably 3 to 8 carbon atoms. Examples of primary and secondary amines which may be represented as hydrogen donors include ethylamine, propylamine, isopropylamine, butylamine, isobutylamine, hexylamine, diethylamine, dipropylamine, di-isopropylamine, dibutylamine, di-isobutylamine, dihexylamine, benzylamine, dibenzylamine and piperidine. When the hydrogen donor is an amine, primary amines are preferred, especially primary amines comprising a secondary alkyl group, particularly isopropylamine and isobutylamine. Carboxylic acids or their esters which may be employed as hydrogen donors comprise commonly from 1 to 10 carbon atoms, preferably from 1 to 3 carbon atoms. In certain embodiments, the carboxylic acid is advantageously a beta-hydroxy-carboxylic acid. Esters may be derived from the carboxylic acid and a (C1-C10) alcohol. Examples of carboxylic acids which may be employed as hydrogen donors include formic acid, lactic acid, ascorbic acid and mandelic acid. The most preferred carboxylic acid is formic acid. In certain preferred embodiments, when a carboxylic acid is employed as hydrogen donor, at least a part of the carboxylic acid is present as salt, preferably an amine, an ammonium or a metal salt. Preferably, when a metal salt of the carboxylic acid is used, the metal is selected from the alkali or alkaline earth metals of the periodic table, and more preferably is selected from the group I elements, such as lithium, sodium or potassium. Amines which may be used to form such salts include both aromatic and non-aromatic amines, also primary, secondary and tertiary amines and comprise typically from 1 to 20 carbon atoms. Tertiary amines, especially trialkylamines, are preferred. Examples of amines which may be used to form salts include trimethylamine, triethylamine, di-isopropylethylamine and pyridine. The most preferred amine is triethylamine. When at least some of the carboxylic acid is present as an amine salt, particularly when a mixture of formic acid and triethylamine is employed, the molar ratio of acid to amine is from 1:1 to 50:1, more preferably from 1:1 to 10:1, and even more preferably is 5:2. Said carboxylic acid (preferably formic acid) and amine (preferably a trialkylamine, more preferably triethylamine) may be added separately to the reaction mass or, preferably, combined in advance so as to form a mixture (preferably an azeotropic mixture) to be added to the reaction mass. A preferred example of said mixture comprising a carboxylic acid and an amine is an azeotropic mixture comprising formic acid and an amine, which, more preferably, is a 5:2 (moles/moles) formic acid-triethylamine azeotropic mixture.

When at least some of the carboxylic acid is present as a metal salt, particularly when a mixture of formic acid and a group I metal salt is employed, the molar ratio of the acid to the metal ions present is from 1:1 to 50:1, preferably from 1:1 to 10:1, and even more preferably is 2:1.

Dehydrogenatable hydrocarbons which may be employed as hydrogen donors comprise hydrocarbons which have a propensity to aromatise or hydrocarbons which have a propensity to form highly conjugated systems. Examples of dehydrogenatable hydrocarbons which may be employed as hydrogen donors include cyclohexadiene, cyclohexene, tetralin, dihydrofuran and terpenes.

Transition metal complexes are used as the asymmetric hydrogenation catalysts for the stereoselective reduction, and, more specifically, those comprising a metal belonging to groups 8, 9 and 10 of the periodic table of elements. The transition metal complexes used according to the present invention are, for example, compounds of formula (9) or formula (10):

$$M_m L_n X'_p Y'_q \qquad (9)$$

$$[M_m L_n X'_p Y'_q] Z'_s \qquad (10)$$

wherein M is a transition metal of group VIII of the periodic table of elements; L is a chiral ligand; X' is a halogen atom, a carboxylate group, an allyl group, a 1,5-cyclooctadiene or a norbornadiene; Y' is a ligand; Z' is an anion; and m, n', p, q and s are each an integer from 0 to 5.

The following is the description of the preferable embodiments of the transition metal complexes mentioned above.

As to formula (9):

1) When M is Ir or Rh, X' is then Cl, Br or I, and when L is a monodentate ligand, then m=p=2, n'=4 and q=0; and when L is a bidentate ligand, then m=n'=p=2 and q=0.

2) When M is Ru, then:

(i) X' is Cl, Br or I, and Y' is a trialkylamino group, and when L is a monodentate ligand, then m=2, n'=p=4 and q=1; and when L is a bidentate ligand, then m=n'=2, p=4, and q=1, or (ii) X' is Cl, Br, or I, and Y' is a pyridyl group or a pyridyl group substituted on the ring, and when L is a monodentate ligand, then m=1, n'=p=2 and q=2; and when L is a bidentate ligand, then m=n'=1, p=2 and q=2, or (iii) X' is a carboxylato group, and when L is a monodentate ligand, then m=1, n'=p=2 and q=0; and when L is a bidentate ligand, m=n'=1, p=2 and q=0;

(iv) X' is Cl, Br or I, and when L is a monodentate ligand, then m=p=2, n'=4 and q=0; and when L is a bidentate ligand, then m=n'=p=2 and q=0;

3) When M is Pd:

(i) X' is Cl, Br or I, and when L is a monodentate ligand, then m=1, n'=2, p=2 and q=0; and when L is a bidentate ligand, m=n'=1, p=2 and q=0, or (ii) X' is an allyl group, and when L is a monodentate ligand, then m=p=2, n'=4 and q=0; and when L is a bidentate ligand, then m=n'=p=2 and q=0.

4) When M is Ni, X is then Cl, Br or I, and when L is a monodentate ligand, then m=1, n'=2, p=2 and q=0; and when L is a bidentate ligand, then m=n'=1, p=2 and q=0.

As to formula (10):

1) When M is Ir or Rh, then X' is 1,5-cyclooctadiene or norbornadiene, and Z' is $BF_4$, $ClO_4$, OTf, $PF_6$, $SbF_6$ or $BPh_4$, and m=n'=p=s=1 and q=0, or m=s=1, n=2 and p=q=0.

2) When M is Ru, then:

(i) X' is Cl, Br or I, Y' is a neutral ligand such as an aromatic compound and an olefinic compound, Z' is Cl, Br, I, $1_3$ or sulfonate, and when L is a monodentate ligand, then m=p=s=q=1 and n'=2; and when L is a bidentate ligand, then m=n'=p=s=q=1, or (ii) X is Cl, Br or I, Z' is $BF_4$, $ClO_4$, OTf, $PF_6$, $SbF_6$ or $BPh_4$, and when L is a monodentate ligand, then m=1, n'=2, p=q=0 and s=2; and L is a bidentate ligand, then m=n'=1, p=q=0 and s=2;

3) When M is Pd or Ni, then:

(i) Z' is $BF_4$, $ClO_4$, OTf, $PF_6$, $SbF_6$ or $BPh_4$, and when L is a monodentate ligand, then m=1, n'=2, p=q=0 and s=2; and when L is a bidentate ligand, then m=n'=1, p=q=0 and s=2.

Preferably in formulae (9) and (10), the transition metal includes ruthenium (Ru), rhodium (Rh), iridium (Ir), palladium (Pd), nickel (Ni).

The chiral ligands represented by L are the same or different, and include monodentate ligands and bidentate ligands. Optically active phosphine ligands, such as optically active bidentate phosphine ligands and chiral diamines are preferable chiral ligands.

More preferred examples of optically active bidentate phosphine ligands include cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted-phospholano)benzene (DuPHOS), 1,2-bis(substituted-phospholano)ethane (BPE), 1-((substituted-phospholano)-2-(diphenylphosphino)benzene (UCAP-Ph), 1-(bis(3,5-dimethylphenyl)phosphino)-2-(substituted-phospholano)benzene (UCAP-DM), 1-((substituted-phospholano)-2-(bis(3,5-di(t-butyl)-4-methoxyphenyl)phosphino)benzene (UCAP-DTBM), 1-((substituted-phospholano)-2-(di-naphthalen-1-ylphosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl) (H3-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis(diphenylphosphino)-6,6'-dimethyl-1,1'-biphenyl (BICHEP), ((5,6),(5',6')-bis(methylenedioxy)biphenyl-2,2'-diyl)(bisdiphenylphosphine) (SEGPHOS), ((5,6),(5',6')-bis(methylenedioxy)biphenyl-2,2'-diyl)(bis(3,5-dimethylphenyl)phosphine) (DM-SEGPHOS) and ((5,6),(5',6')-bis(methylenedioxy)biphenyl-2,2'-diyl)(bis(3,5-di(tert-butyl)-4-methoxyphenyl)phosphine) (DTBM-SEGPHOS), 2,2',6,6'-tetramethoxy-4,4'-bis(diphenylphosphino)-3,3'-bipyridine (P-Phos), 4,12-bis(diphenylphosphino)-[2.2]-paracyclophane (Phanephos), and 1-(diphenylphosphino)-2-[1-[(diphenylphosphino)methylamino]ethyl]ferrocene (MeBoPhoz) or a combination thereof.

The chiral ligands represented by L can be used in enantiomerically enriched form or in the form of a single enantiomer.

Examples of chiral diamines ligands include diamines of formula (14):

(14)

in which:

$R^i$, $R^j$, $R^k$ or $R^l$ are independently hydrogen, a saturated or unsaturated alkyl group, a saturated or unsaturated cycloalkyl group, an aryl group, a urethane or a sulphonyl group;

$R^e$, $R^f$, $R^g$ or $R^h$ are independently hydrogen, a saturated or unsaturated alkyl group, a saturated or unsaturated cycloalkyl group, an aryl group; alternatively, $R^e$ together with —$CR^f$-$A_t$-$CR^g$, $R^e$ together with —$CR^f$-$A_t$-$CR^h$, $R^f$ together with —$CR^e$-$A_t$-$CR^g$ or $R_f$ together with —$CR^e$-$A_t$-$CR^h$ may form a 4- to 8-membered cycloalkyl optionally substituted by 1, 2 or 3 substituents independently selected among (C1-C6)alkyl-;

A is a linking group comprising one or two substituted or unsubstituted carbon atoms; and t is 0 or 1.

Preferably at least one of $R^e$, $R^f$, $R^g$ or $R^h$ is hydrogen.

Alkyl groups may be straight chain or branched alkyl groups (e.g. C1-C20) such as methyl, ethyl, propyl, isopropyl, butyl, iso-butyl, sec-butyl, tert-butyl, pentyl, hexyl, heptyl, octyl, nonyl, decyl, dodecyl, and stearyl; "cycloalkyl" is meant to encompass, e.g., (C3-C10)cycloalkyl-groups such as cyclopropyl, cyclobutyl, cyclopentyl, cyclohexyl or adamantly. Aryl groups may be phenyl (Ph), naphthyl (Np) or anthracyl and heteroaryl groups such as pyridyl. The alkyl groups may be optionally substituted with one or more substituents such as halide (Cl, Br, F or I) or alkoxy groups, e.g. methoxy, ethoxy or propoxy groups. The aryl groups may be optionally substituted with one or more substituent such as halide (Cl, Br, F or I), (C1-C20)alkyl-, (C1-C20)alkoxy-, amino ($NR^m$, where $R^m$=hydrogen or alkyl), hydroxy, carboxy ($CO_2R^n$, $R^n$=H or alkyl) or sulfonate (mesyl, tosyl, trimethylphenylsulfonyl, triisopropylphenylsulfonyl) groups. Suitable substituted aryl groups include 4-methylphenyl (tolyl), 3,5-dimethylphenyl (xylyl), 4-methoxyphenyl and 4-methoxy-3,5-dimethylphenyl.

$R^i$, $R^j$, $R^k$ or $R^l$ may be the same or different and are preferably selected from the group consisting of hydrogen, methyl, ethyl, isopropyl, cyclohexyl, phenyl, 4-methylphenyl mesyl, tosyl, trimethylphenylsulfonyl (preferably 2,4,6-trimethylphenylsulfonyl) and triisopropylphenylsulfonyl (preferably 2,4,6-triisopropylphenylsulfonyl).

More preferably $R^i$, $R^j$, $R^k$ are the same and are hydrogen while $R^l$ is mesyl, tosyl, trimethylphenylsulfonyl (preferably 2,4,6-trimethylphenylsulfonyl) and triisopropylphenylsulfonyl (preferably 2,4,6-triisopropylphenylsulfonyl).

$R^e$, $R^f$, $R^g$ or $R^h$ may be the same or different and are preferably hydrogen, methyl, ethyl, propyl, iso-propyl, butyl, iso-butyl, sec-butyl, tert-butyl, cycloalkyl groups such as cyclohexyl, aryl groups such as substituted or unsubstituted phenyl or naphthyl groups.

In the present invention $R^e$ together with —$CR^f$-$A_t$-$CR^g$, $R^e$ together with —$CR^f$-$A_t$-$CR^h$, $R^f$ together with —$CR^e$-$A_t$-$CR^g$ or $R^f$ together with —$CR^e$-$A_t$-$CR^h$ may form one or more 4- to 8-membered cycloalkyl. The ring structure may comprise a 4- to 7-membered alkyl or heteroalkyl ring, preferably a 5- or 6-membered alkyl or heteroalkyl ring, more preferably a cyclohexyl ring.

Specific examples of chiral diamines ligands include N-p-tosyl-1,2-diphenylethylenediamine (Ts-DPEN), N-methanesulfonyl-1,2-diphenylethylenediamine (Ms-DPEN), N-[1,2-diphenyl-2-[(3-phenylpropyl)amino]ethyl]-4-methyl-benzenesulfonamide (C3-teth-Ts-DPEN), N-[1,2-diphenyl-2-[(4-phenylbutyl)amino]ethyl]-4-methyl-benzenesulfonamide (C4-teth-Ts-DPEN), N-[1,2-diphenyl-2-[(3-phenylpropyl)amino]ethyl]-methanesulfonamide (C3-teth-Ms-DPEN), N-[1,2-diphenyl-2-[(4-phenylbutyl)amino]ethyl]-methanesulfonamide (C4-teth-Ms-DPEN), N-[1,2-diphenyl-2-[(3-phenylpropyl)amino]ethyl]-2,4,6-trimethyl-benzenesulfonamide (C3-teth-Mts-DPEN), N-[1,2-diphenyl-2-[(4-phenylbutyl)amino]ethyl]-2,4,6-trimethyl-benzenesulfonamide (C4-teth-Mts-DPEN), N-[1,2-diphenyl-2-[(3-phenylpropyl)amino]ethyl]-2,4,6-triisopropyl-benzenesulfonamide (C3-teth-Tris-DPEN), N-[1,2-diphenyl-2-[(4-phenylbutyl)amino]ethyl]-2,4,6-triisopropyl-benzenesulfonamide (C4-teth-Tris-DPEN), N-p-tosyl-1,2-cyclohexanediamine (Ts-DACH).

Preferably $R^e$, $R^f$, $R^g$ or $R^h$ or linking group A are chosen such that the ligand may be homochiral, i.e. (R,R) or (S,S) or have one (R) and one (S) centre. Preferably the chiral diamine is homochiral.

Linking group A provides a bond between the carbon atoms to which the amine groups —$NR^iR^k$ and —$NR^iR^j$ are linked or, in the case when t is 1, comprises one or two substituted or unsubstituted carbon atoms. Substituting groups may replace one or both hydrogen atoms on the carbon atoms. The substituting groups may comprise one or more (C1-C20) alkyl-, (C1-C20)alkoxy-, or amino (NR°, where R°=hydrogen or alkyl). The substituting groups may form one or more ring structures, e.g. a 4- to 7-membered ring structures incorporating one or more carbon atoms making up the linking group. Thus linking group A may comprise one or two carbon atoms forming part of one or more aromatic ring structures. The ligands represented by Y' are the same or different and include neutral ligands such as aromatic compounds and olefinic compounds. Examples of the aromatic compounds include benzene, p-cymene, 1,3,5-trimethylbenzene (mesitylene) and hexamethylbenzene. Examples of olefinc compounds include ethylene, 1,5-cyclooctadiene (cod), cyclopentadiene and norbornadiene (nbd). Examples of other neutral ligands include N,N-dimethylformamide (DMF), acetonitrile, benzonitrile, acetone and chloroform.

The halogen atoms represented by X' include a chlorine atom, a bromine atom and an iodine atom.

The anions represented by Z' in formula (10) include $BF_4$, $ClO_4$, OTf, $PF_6$, $SbF_6$, $BPh_4$, Cl, Br, I, $I_3$ and sulfonate, wherein Tf represents a triflate group ($SO_2CF_3$).

Specific examples of transition metal complexes useful for the aim include rhodium complexes (preferably [Rh(L)Cl]$_2$, [Rh(L)Br]$_2$, [Rh(L)I]$_2$, [Rh(cod)(L)]$BF_4$, [Rh(cod)(L)]$ClO_4$, [Rh(cod)(L)]$PF_6$, [Rh(cod)(L)]$BPh_4$, [Rh(cod) (L)]OTf, [Rh(nbd)(L)]$BF_4$, [Rh(nbd)(L)]$ClO_4$, [Rh(nbd)(L)]$PF_6$, [Rh(nbd)(L)]$BPh_4$, [Rh(nbd)(L)]OTf and [Rh(L)$_2$]$ClO_4$), ruthenium complexes (preferably Ru(OAc)$_2$(L), Ru$_2$Cl$_4$(L)$_2$NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(pcymene)(L)]I, [Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$, Ru(OCOCF$_3$)$_2$(L), [{RuCl(L)}$_2$(p-Cl)$_3$][Me$_2$NH$_2$] and [{RuCl(L)}$_2$ (p-Cl)$_3$][Et$_2$NH$_2$]), iridium complexes ([Ir(L)Cl]$_2$, [Ir(L)Br]$_2$, [Ir(L)I]$_2$, [Ir(cod)(L)]BF$_4$, [Ir(cod)(L)]ClO$_4$, [Ir(cod)(L)]PF$_6$, [Ir(cod)(L)]BPh$_4$, [Ir(cod)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$ and [Ir(nbd)(L)]OTf), pallidum complexes (preferably PdCl$_2$(L), (Tc-allyl)Pd(L), [Pd(L)]BF$_4$, [Pd(L)]ClO$_4$, [Pd(L)]PF$_6$, [Pd(L)]BPh$_4$ and [Pd(L)]OTf) and nickel complexes (preferably NiCl$_2$(L), NiBr$_2$(L) and NiI$_2$(L)).

Homogeneous catalysts of rhodium, ruthenium or iridium coordinated with chiral ligands such as Ts-DPEN, Ms-DPEN, Ts-DACH, C3-teth-TsDPEN, C4-teth-TsDPEN, C3-teth-MsDPEN, C4-teth-MsDPEN, C3-teth-MtsDPEN, C3-teth-TrisDPEN, C4-teth-TrisDPEN, PhanePhos, Binap, P-Phos, H-[P-H8-BINOL]-BoPhoz, and MeBoPhoz are even more preferred examples of asymmetric hydrogenation catalysts.

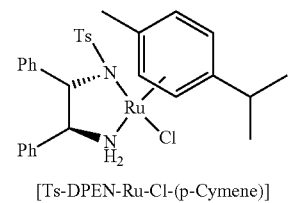

[Ts-DPEN-Ru-Cl-(p-Cymene)]

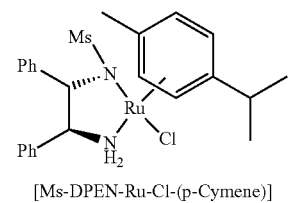

[Ms-DPEN-Ru-Cl-(p-Cymene)]

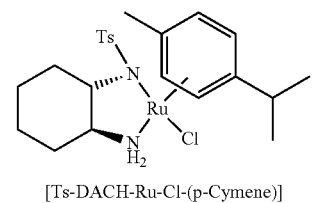

[Ts-DACH-Ru-Cl-(p-Cymene)]

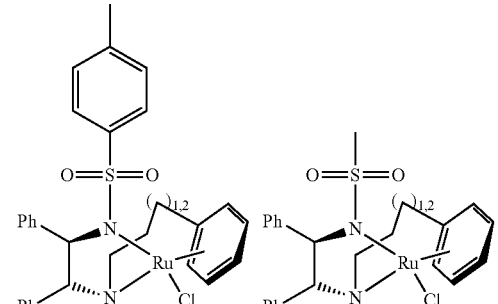

C3 and C4-
[(R,R)-teth-TsDpen RuCl]

C3 and C4-
[(R,R)-teth-MsDpen RuCl]

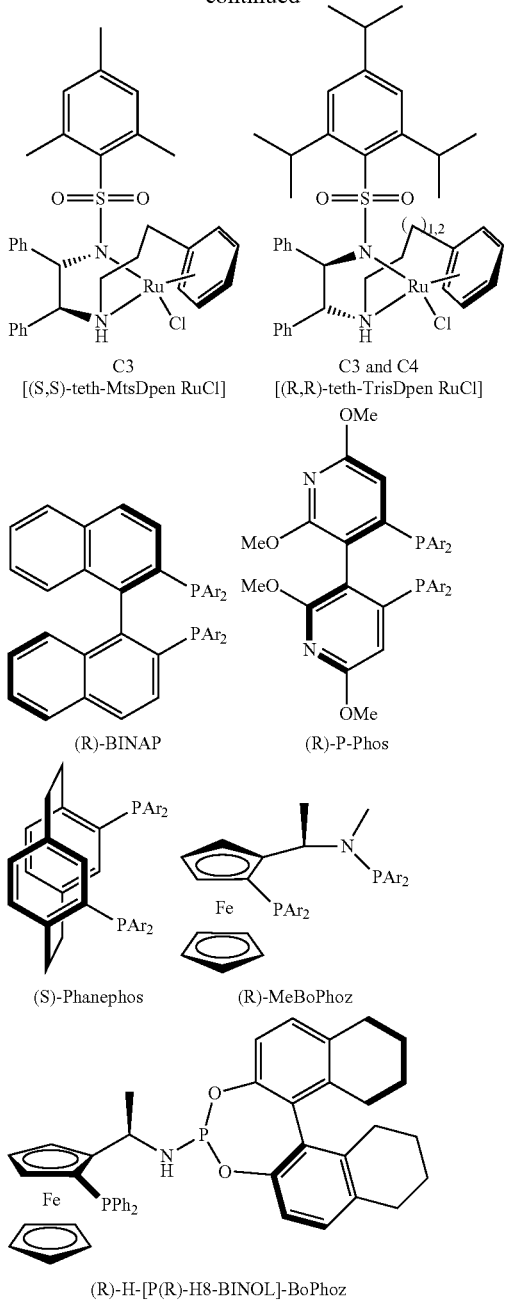

In step b), the asymmetric hydrogenation catalyst is conveniently used in a stoichiometry from 0.0001 to 20 mol %, preferably from 0.01 to 5 mol %, more preferably from 0.02 to 4 mol %, even more preferably from 0.03 to 2 mol %, compared to the molar quantity of the compound of general formula (3).

Although 1 atmosphere (atmospheric pressure) (0.1 MPa) of hydrogen may be enough for the stereoselective reduction, the pressure of hydrogen is conveniently from 1 to 100 atm. (0.1 to 10 MPa), or more preferably from 2 to 80 atm. (0.2 to 8 MPa).

The molar ratio of the compound of general formula (3) to the hydrogen donor may vary in a very wide range. Preferably, the molar ratio of the compound of general formula (3) to the hydrogen donor is from 1:1 to 1:50. More preferably, the molar ratio of the compound of general formula (3) to the hydrogen donor is between and optionally includes any two of the following values: 1:1, 1:2, 1:3, 1:4, 1:5, 1:6, 1:7, 1:8, 1:9, 1:10, 1:12, 1:13, 1:14, 1:15, 1:16, 1:17, 1:18, 1:19, 1:20, 1:25, 1:30, 1:35, 1:40 or 1:45.

Step b), being it performed under stereoselective conditions or not, is conveniently carried out in a solvent, for example selected from the group consisting of aliphatic hydrocarbons (such as pentane, hexane, heptane, octane, decane, cyclohexane), aromatic hydrocarbons (such as benzene, toluene, xylene), halogenated hydrocarbons (such as dichloromethane, 1,2-dichloroethane, chloroform, carbon tetrachloride, o-dichlorobenzene), ethers (such as diethyl ether, diisopropyl ether, tert-butyl methyl ether, dimethoxyethane, ethyleneglycol diethyl ether, tetrahydrofuran, 1,4-dioxane, 1,3-dioxolane) alcohols (such as methanol, ethanol, 2-propanol, 1-butanol, 2-butanol, tert-butanol, 2-ethoxyethanol, benzyl alcohol), polyalcohols (such as ethylene glycol, propylene glycol, 1,2-propanediol, glycerol), amides (such as N,N-dimethylformamide, N,N-dimethylacetamide), sulfoxides (such as dimethyl sulfoxide), cyano-containing organic compounds (such as acetonitrile), N-methylpyrrolidone, fluorine containing aliphatic alcohol (such as 2,2,2-trifluoroethanol) and water.

Optionally step b) is carried out in the presence of at least one acid or of iodine. Acids suitable for the aim include for example inorganic acids, organic acids, and Lewis acids. Examples of suitable inorganic acids include, for example, hydrochloric acid, hydrobromic acid, sulfuric acid, phosphoric acid, tetrafluoroboric acid, perchloric acid, and periodic acid. Suitable organic acids include, for example, carboxylic acids (e.g. formic acid, acetic acid, valeric acid, hexanoic acid, citric acid, chloroacetic acid, dichloroacetic acid, trichloroacetic acid, trifluoroacetic acid, benzoic acid, salicylic acid, oxalic acid, succinic acid, malonic acid, phthalic acid, tartaric acid, malic acid, and glycolic acid), and sulfonic acids (e.g. methanesulfonic acid, benzenesulfonic acid, p-toluenesulfonic acid and trifluoromethanesulfonic acid). Suitable Lewis acids, are, e.g., halogenated aluminiums (e.g. aluminium chloride and aluminium bromide). halogenated dialkylaluminiums (e.g. diethylaluminium chloride, diethylaluminium bromide, and diisoproylaluminium chloride), tri-alkoxy aluminiums (e.g. triethoxyaluminium, triisopropoxyaluminium and tri-t-butoxyaluminium), titanium halides (e.g. titanium tetrachloride), tetraalkoxy titaniums (e.g. titanium isopropoxide), halogenated borons (e.g. boron trifluoride, boron trichloride, boron tribromide and boron trifluoride-diethyl ether complex), zinc halides (e.g. zinc chloride and zinc bromide). Each of these acids may be used alone or in combination with any one of the others.

Preferably step b) is carried out in a solvent or in a solvent mixture comprising at least one alcohol (e.g. selected from the group consisting of methanol, ethanol and 2-propanol), more preferably in the presence of an acid.

Even more preferably step b) is carried out in a fluorine containing aliphatic alcohol or in a solvent mixture comprising it, said fluorine containing aliphatic alcohol being, more preferably, 2,2,2-trifluoroethanol.

Step b) is normally performed at a temperature from 15 to 120° C., preferably from 20 to 100° C., more preferably from 30 to 80° C., even more preferably from 40 to 70° C. However, step b) can be carried out at a temperature from −30 to 0° C., or at a temperature from 100 to 250° C.

The volume of the solvent or of the mixture of solvents used in the preparation of compound of general formula (7) is normally from 1 mL to 150 mL per gram of the compound of general formula (3). Preferably, the volume of the solvent is between and optionally includes any two of the following values: 2 mL, 3 mL, 4 mL, 5 mL, 6 mL, 7 mL, 8 mL, 9 mL, 10 mL, 15 mL, 20 mL, 25 mL, 30 mL, 35 mL, 40 mL, 45 mL, 50 mL, 55 mL, 60 mL, 65 mL, 70 mL, 75 mL, 80 mL, 85 mL, 90 mL, 95 mL, 100 mL, 105 mL, 110 mL, 115 mL, 120 mL, 125 mL, 130 mL, 135 mL, 140 mL or 145 mL per gram of the compound of general formula (3).

According to a preferred embodiment of this aspect of the invention, step b) is carried out in the presence of a compound of general formula (2) (preferably a compound of general formula (2A) or (2B)).

The presence of a compound of general formula (2) (preferably a compound of general formula (2A) or (2B)) has the advantageous effect of ensuring a high conversion yield (i.e. at least 75%, preferably at least 80%, more preferably at least 85%, even more preferably at least 90%, said percentages being expressed on a molar basis) of the compound of general formula (3) (preferably a compound of general formula (3A), (3B), (3A1) or (3A2), more preferably a compound of general formula (3A'), (3A"), (3B'), (3B"), (3A'''), (3A''''), (3B''') or (3B'''')) into the compound of general formula (7) (preferably a compound of general formula (7A'), (7A"), (7B') or (7B")).

The molar ratio of the compound of general formula (3) to the compound of general formula (2), when used, may vary in a very wide range. Preferably, the molar ratio of the compound of general formula (3) to the compound of general formula (2) is from 1:0.5 to 1:10. More preferably, the molar ratio of the compound of general formula (3) to the compound of general formula (2) is between and optionally includes any two of the following values: 1:1, 1:1.5, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

According to a more preferred embodiment of this aspect of the invention, steps a) and b) are carried out without isolating the compound of general formula (3), preferably a compound of general formula (3A), (3B), (3A1) or (3A2), more preferably a compound of general formula (3A'), (3A"), (3B'), (3B"), (3A'''), (3A''''), (3B''') or (3B'''').

Even more preferably steps a) and b) are performed one-pot by mixing a compound of general formula (3) (preferably a compound of general formula (3A), (3B), (3A1) or (3A2), more preferably a compound of general formula (3A'), (3A"), (3B'), (3B"), (3A'''), (3A''''), (3B''') or (3B'''')), a compound of general formula (2) (preferably a compound of general formula (2A) or (2B)), and at least one asymmetric hydrogenation catalyst in the presence of a hydrogen donor and, optionally, of at least one dehydrating agent different from a titanium alkoxide (preferably different from a titanium-based Lewis acid, more preferably different from a metal-based Lewis acid), thus leading to the direct preparation of the compound of general formula (7), preferably a compound of general formula (7A'), (7A"), (7B') or (7B"), in enantiomerically enriched or enantiomerically pure form.

A variant of the process object of this aspect of the invention includes an additional and optional step g), carried out after step b), comprising converting said compound of general formula (7), preferably a compound of general formula (7A'), (7A"), (7B') or (7B"), into Ozanimod or a salt thereof (preferably a salt of Ozanimod with hydrogen chloride or with a chiral Brønsted acid, more preferably a salt with a chiral Brønsted acid selected from the group consisting of (1R)-(−)-10-camphorsulfonic acid, (1S)-(+)-10-camphorsulfonic acid, N-formyl-L-leucine, L-(−)-malic acid, D-(+)-malic acid, (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid).

The optional step g) of the process of the invention can be carried out according to five alternative synthetic schemes, discussed below as g.1), g.2), g.3), g.4) and g.5).

The synthetic scheme g.1) can be performed when in the compound of general formula (7) $R^1$ is a 1,2,4-oxadiazole attached to the bicycle via carbon 3 and substituted in position 5 with a 3'-cyano-4'-isopropoxyphenyl group and $R^{10}$ is —CH$_2$OPg, and involves the deprotection of the oxygen protecting group. Deprotection conditions are those generally known to the person skilled in the art, such as those described in Theodora W. Green, *Protective Groups in Organic Synthesis*, John Wiley & Sons (1999) on pages 23-113 (for ethers), on pages 113-148 (for silyl ethers), on pages 149-179 (for esters) or on pages 179-187 (for carbonates). All these procedures are herein incorporated by reference.

The synthetic scheme g.2) can be performed when in the compound of general formula (7) $R^1$ is a 1,2,4-oxadiazole attached to the bicycle via carbon 3 and substituted in position 5 with a 3'-cyano-4'-isopropoxyphenyl group and $R^{10}$ is —CO$_2$R$^{12}$, and involves the reduction of a carboxylic moiety (being it either an ester or an acid) to the corresponding alcohol. Suitable reducing conditions are generally known in the field. Preferably this step is carried out according to one of the procedures described above to operate step b).

The synthetic scheme g.3) can be performed when in the compound of general formula (7) $R^1$ is —CN and $R^{10}$ is —CH$_2$OPg, and involves (i) the deprotection of the oxygen protecting group and (ii) the formation of the 1,2,4-oxadiazole attached to the bicycle via carbon 3 and substituted in position 5 with a 3'-cyano-4'-isopropoxyphenyl group (said steps (i) and (ii) being performed in any order). Conditions suitable for the aim include, e.g., those specified above to operate steps g.1), d), e) and e').

The synthetic scheme g.4) can be performed when in the compound of general formula (7) $R^1$ is —CN and $R^{10}$ is —CO$_2$R$^{12}$, and involves (iii) the reduction of a carboxylic moiety and (iv) the formation of the 1,2,4-oxadiazole attached to the bicycle via carbon 3 and substituted in position 5 with a 3'-cyano-4'-isopropoxyphenyl group (said steps (iii) and (iv) being performed in any order). Conditions suitable for the aim include, for example, those specified above to operate steps g.2), d), e) and e').

The synthetic scheme g.5) can be performed when in the compound of general formula (7) $R^1$ is —CN and $R^{10}$ is CH$_2$OH, and involves the formation of the 1,2,4-oxadiazole attached to the bicycle via carbon 3 and substituted in position 5 with a 3'-cyano-4'-isopropoxyphenyl group, optionally after having protected the hydroxyl and/or the amino moieties. Conditions suitable for the aim include, for example, those specified in Theodora W. Green, *Protective Groups in Organic Synthesis*, John Wiley & Sons (1999) for the protection of alcohols (see in particular pages 23-113 for ethers, pages 113-148 for silyl ethers, pages 149-179 for esters and pages 179-187 for carbonates), those described above to operate steps g.1), d) and e) or the procedures described under paragraphs [310] and [366] to [372] of WO 2011/060392 A1.

Conditions suitable for the protection of the amino group are, e.g., described below in respect of step k.2.2)

According to a further aspect thereof, the present invention relates to a process for the preparation of an enantiomerically pure amine of general formula (12) or a salt thereof, said process comprising:

h) providing an azide of formula (13):

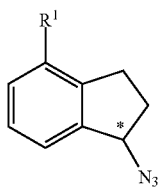
(13)

i) converting said azide of formula (13) into an amine of formula (12):

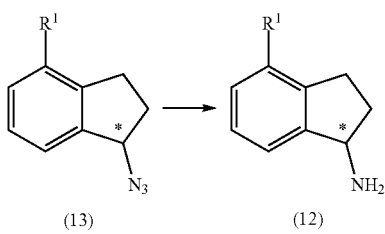
(13)    (12)

j) optionally converting said amine of formula (12) into an enantiomerically pure amine of formula (12) or an enantiomerically pure salt thereof by treatment with a chiral or an achiral Brønsted acid;

wherein $R^1$ assumes the meanings reported above; said process being characterized in that step i) is performed according to Staudinger reaction conditions.

According to a first preferred embodiment of this aspect of the invention, an azide of formula (13A) (i.e. an azide of general formula (13) in which $R^1$ is —CN), more preferably an enantiomerically enriched azide of general formula (13A), even more preferably an enantiomerically pure azide of formula (13A) is provided in step h).

According to a second preferred embodiment of this aspect of the invention, an azide of formula (13B) (i.e. an azide of general formula (13) in which $R^1$ is a 1,2,4-oxadiazole attached to the bicycle via carbon 3 and substituted in position 5 with a 3'-cyano-4'-isopropoxyphenyl group), more preferably an enantiomerically enriched azide of general formula (13B), even more preferably an enantiomerically pure azide of formula (13B) is provided in step h).

The azide of formula (13A) and the enantiomerically enriched or pure versions thereof are commercially available; alternatively, they can be prepared according to standard techniques in organic synthesis, for example, using a procedure analogous to that described in the international application WO 2011/060389 A1. The azide of formula (13B), preferably an enantiomerically enriched or pure version thereof, can be prepared using a procedure analogous to that described in WO 2011/060389 A1 starting from an indanone of formula (1").

Alternatively, the azide of formula (13B), preferably an enantiomerically enriched or pure version thereof, can prepared according to the following steps:

h.1) treating an azide of formula (13A) with hydroxylamine or a salt thereof so as to provide an amidoxime of formula (5A1), a tautomer or a salt thereof:

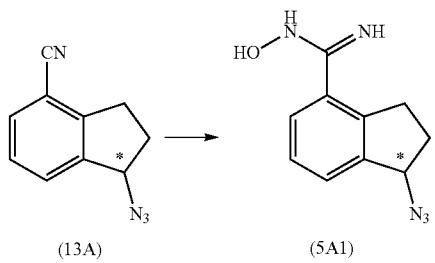 [SMILES: N#Cc1cccc2c1CCC2N=[N+]=[N-] ; [N-]=[N+]=NC1CCc2c(C(=N)NO)cccc21]
(13A)    (5A1)

h.2) converting said amidoxime of formula (5A1), the tautomer or the salt thereof, into the azide of formula (13B):

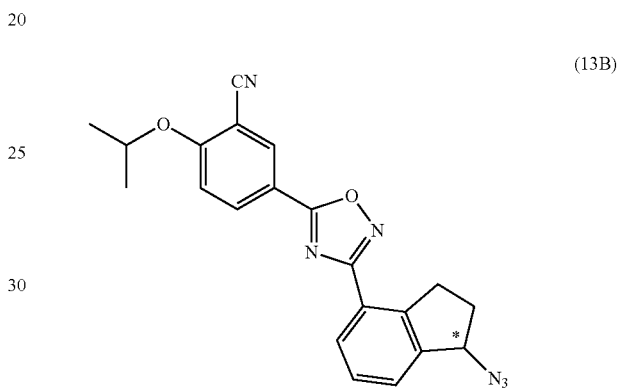
(13B)

Step h.1) entails the treatment of the azide of formula (13A), preferably an enantiomerically enriched azide of formula (13A), more preferably an enantiomerically pure azide of formula (13A), with hydroxylamine or a salt thereof so as to provide an amidoxime of formula (5A1), a tautomer or a salt thereof, preferably an enantiomerically enriched amidoxime of formula (5A1), a tautomer or a salt thereof, more preferably an enantiomerically pure amidoxime of formula (5A1), a tautomer or a salt thereof.

Preferably this step is performed according to one of the procedures detailed above in respect of step d).

The amidoxime of formula (5A1), the tautomer or the salt thereof, is further converted, according to step h.2), into the azide of formula (13B), preferably into an enantiomerically enriched version thereof, more preferably an enantiomerically pure azide of formula (13B), by treatment with a compound of formula (8).

Preferably this step is performed according to one of the procedures detailed above in respect of step e).

A variant of the process object of this aspect of the invention includes an additional and optional step h.2'), carried out after step h.2), comprising heating the mass resulting from the reaction between the compound of formula (8) and the amidoxime of formula (5A1), the tautomer or the salt thereof, preferably a mass comprising a compound of general formula (6A1), a tautomer or a salt thereof, to a temperature normally from 50° C. to 120° C. so as to increase the rate of conversion into the enantiomerically pure azide of formula (13B).

(6A1)

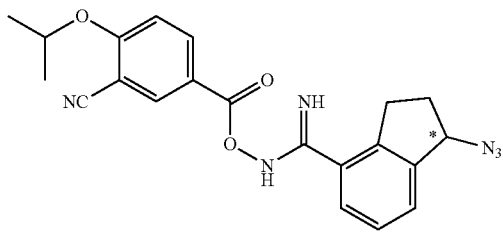

In step i), the azide of formula (13), preferably an azide of formula (13A) or (13B), more preferably an enantiomerically enriched version of any one of them, even more preferably an enantiomerically enriched pure azide of formula (13), (13A) or (13B), is reduced to the corresponding amine of formula (12), preferably an amine of formula (12A) or (12B), more preferably an enantiomerically enriched azide of formula (12), (12A) or (12B), even more preferably an enantiomerically pure azide of formula (12), (12A) or (12B), according to Staudinger reaction conditions.

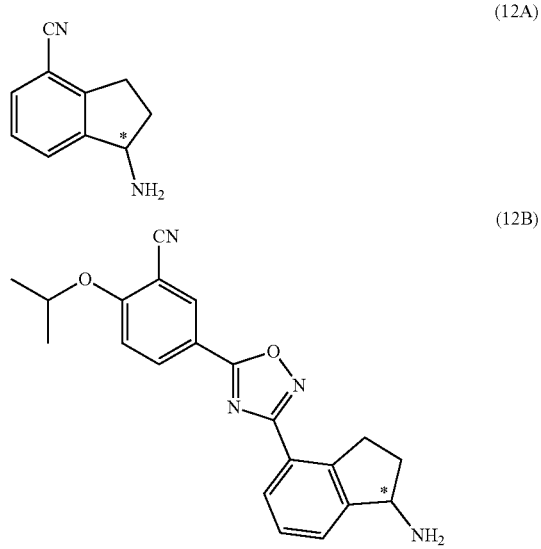

The Staudinger reaction occurs between a phosphine and an azide to produce a phosphazide, which loses $N_2$ to form an iminophosphorane. In the presence of water, this intermediate hydrolyses spontaneously to yield a primary amine and the corresponding phosphine oxide. Preferably, said reduction can be performed by treating the azide of formula (13), more preferably the azide of formula (13A) or (13B), even more preferably an enantiomerically enriched version of any one of them, most preferably an enantiomerically pure azide of formula (13), (13A) or (13B), with an optionally supported trivalent phosphorus compound, such as a trialkyl- or triarylphosphine (e.g. tris-(3-hydroxypropyl)phosphine or preferably triphenylphosphine), in a polar aprotic solvent, such as an ether (e.g., tert-butyl methyl ether, di-tert-butyl ether, diethyl ether, diisopropyl ether, cyclopentyl methyl ether or, preferably, tetrahydrofuran or 2-methyltetrahydrofuran), an aromatic hydrocarbon (such as benzene, toluene, xylene) or a mixture of said solvents.

According to a preferred embodiment of this aspect of the invention a mixture of an ether (preferably tetrahydrofuran or 2-methyltetrahydrofuran) and an aromatic hydrocarbon (preferably toluene) is used in step i).

Step i) is normally performed at a temperature from 10° C. to the reflux temperature of the solvent or mixture of solvents used, preferably at a temperature from 15 to 80° C., more preferably from 20 to 70° C., even more preferably from 25 to 60° C.

The volume of the solvent or of the mixture of solvents used in the preparation of the amine of formula (12) is normally from 5 mL to 100 mL per gram of the azide of formula (13). Preferably, the volume of the solvent is between and optionally includes any two of the following values: 10 mL, 15 mL, 20 mL, 25 mL, 30 mL, 35 mL, 40 mL, 45 mL, 50 mL, 55 mL, 60 mL, 65 mL, 70 mL, 75 mL, 80 mL, 85 mL, 90 mL, or 95 mL per gram of the azide of formula (13).

The molar ratio of the azide of formula (13) to the optionally supported trivalent phosphorus compound may vary in a very wide range. Preferably, the molar ratio of the azide of formula (13) to the optionally supported trivalent phosphorus compound is from 1:0.5 to 1:10. More preferably, the molar ratio of the azide of formula (13) to the optionally supported trivalent phosphorus compound is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:3, 1:4, 1:5, 1:6, 1:7, 1:8, or 1:9.

The optional step j) of the process object of this aspect of the invention can be carried out according to three alternative synthetic schemes, discussed below as j.1), j.2) and j.3).

The synthetic scheme j.1) can be performed when an enantiomerically pure amine of formula (12) (preferably an enantiomerically pure amine of formula (12A) or (12B)) is produced in step i), and involves the treatment of said enantiomerically pure amine with a Brønsted acid, being either chiral or achiral, preferably formic acid or tartaric acid.

The molar ratio of the enantiomerically pure amine of formula (12) to the achiral or chiral Brønsted acid may vary in a very wide range. Preferably, the molar ratio of the enantiomerically pure amine of formula (12) to the achiral or chiral Brønsted acid is from 1:0.5 to 1:2. More preferably, the molar ratio of the enantiomerically pure amine of formula (12) to the achiral or chiral Brønsted acid is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9 or 1:2.

The synthetic scheme j.2) can be carried out when an enantiomerically enriched amine of formula (12) (preferably an enantiomerically enriched amine of formula (12A) or (12B)) is produced in step i), and comprises treating said enantiomerically enriched amine (12), (12A) or (12B) with a chiral Brønsted acid, preferably a chiral Brønsted acid selected from the group consisting of (1R)-(−)-10-camphorsulfonic acid, (1S)-(+)-10-camphorsulfonic acid, N-formyl-L-leucine, L-(−)-malic acid, D-(+)-malic acid, (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid, to obtain an enantiomerically pure salt of the amine of formula (12), (12A) or (12B) through diastereomeric salt resolution.

More preferably step j.2) entails the treatment of an enantiomerically enriched amine of formula (12) (preferably an enantiomerically enriched amine of formula (12A) or (12B)) with a chiral Brønsted acid selected from the group consisting of (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid.

The diastereomeric salt resolution may be performed by heating the mass resulting from the addition of the chiral Brønsted acid to a temperature next to the boiling point of the solvent used, followed by cooling to a temperature from 0 to 30° C. The formation of the salt is complete within some minutes but the reaction time can be extended to several hours without causing any disturbance.

Examples of solvents suitable for the formation and fractionation of the salts in the diastereomeric salt resolution are water miscible solvents, such as alcohols (e.g. methanol, ethanol, 2-propanol, 1-butanol) optionally in mixture with water.

The molar ratio of the enantiomerically enriched amine of formula (12) to the chiral Brønsted acid may vary in a very wide range. Preferably, the molar ratio of the enantiomerically enriched amine of formula (12) to the chiral Brønsted acid is from 1:0.5 to 1:2. More preferably, the molar ratio of the enantiomerically enriched amine of formula (12) to the achiral or chiral Brønsted acid is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9 or 1:2.

The synthetic scheme j.3) can be carried out when an amine of formula (12) in the form of a racemic mixture is produced in step i). Preferably synthetic scheme j.3) comprises treating said racemic amine (12) with a chiral Brønsted acid, preferably a chiral Brønsted acid selected from the group consisting of (1R)-(−)-10-camphorsulfonic acid, (1S)-(+)-10-camphorsulfonic acid, N-formyl-L-leucine, L-(−)-malic acid, D-(+)-malic acid, (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid, to obtain an enantiomerically pure salt of the amine of formula (12), (12A) or (12B) through diastereomeric salt resolution.

More preferably synthetic scheme j.3) entails the treatment of a racemic amine of formula (12) with a chiral Brønsted acid selected from the group consisting of (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid.

The molar ratio of the racemic amine of formula (12) to the chiral Brønsted acid may vary in a very wide range. Preferably, the molar ratio of the racemic amine of formula (12) to the achiral or chiral Brønsted acid is from 1:0.5 to 1:2. More preferably, the molar ratio of the racemic amine of formula (12) to the achiral or chiral Brønsted acid is between and optionally includes any two of the following values: 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9 or 1:2.

According to a more preferred embodiment of this aspect of the invention, the enantiomerically pure salt of the amine of formula (12A) resulting from step i) or j), is an enantiomerically pure salt of the amine of formula (12A) with L-(+)-tartaric acid, preferably an enantiomerically pure L-(+)-hemitartrate salt of the amine of formula (12A). More preferably said enantiomerically pure L-(+)-hemitartrate salt of the amine of formula (12A) shows an X-ray powder diffraction pattern that, when collected with the Kα radiation of copper ($\lambda$=1.5406 Å), is characterized by peaks at:

I. 6.84°, 19.20°, 22.68° and 25.68°±0.2° 2θ; or
II. 6.84°, 16.16°, 19.20°, 22.68° and 25.68°±0.2° 2θ.

Even more preferably said enantiomerically pure L-(+)-hemitartrate salt of the amine of formula (12A) shows an X-ray powder diffraction pattern that, when collected with the Kα radiation of copper ($\lambda$=1.5406 Å), is characterized by at least 4 peaks (±0.2° 2θ) selected from Table 1A or 1B:

TABLE 1A

| °2θ | d space (Å) | $I_{rel}$ (%) |
|---|---|---|
| 6.84 | 12.9126 | 59 |
| 16.16 | 5.4804 | 49 |
| 16.96 | 5.2236 | 40 |
| 19.20 | 4.6190 | 90 |
| 22.68 | 3.9175 | 100 |
| 25.68 | 3.4662 | 56 |
| 36.60 | 2.4532 | 33 |

TABLE 1B

| °2θ | d space (Å) | $I_{rel}$ (%) |
|---|---|---|
| 6.84 | 12.9126 | 59 |
| 12.32 | 7.1786 | 35 |
| 16.16 | 5.4804 | 49 |
| 16.96 | 5.2236 | 40 |
| 19.20 | 4.6190 | 90 |
| 20.56 | 4.3164 | 27 |
| 20.88 | 4.2510 | 29 |
| 22.68 | 3.9175 | 100 |
| 25.68 | 3.4662 | 56 |
| 26.36 | 3.3783 | 26 |
| 26.64 | 3.3435 | 24 |
| 28.40 | 3.1401 | 28 |
| 36.60 | 2.4532 | 33 |

A variant of the process object of this aspect of the invention includes an additional and optional step k), carried out after either step i) or j), comprising converting said enantiomerically pure amine of general formula (12) or the salt thereof (preferably an enantiomerically pure amine of formula (12A), (12B) or a salt of any one of them), into an enantiomerically pure compound of general formula (7) (preferably Ozanimod) or a salt thereof (preferably a salt with a chiral or achiral Brønsted acid, more preferably a salt with a chiral Brønsted acid selected from the group consisting of (1R)-(−)-10-camphorsulfonic acid, (1 S)-(+)-10-camphorsulfonic acid, N-formyl-L-leucine, L-(−)-malic acid, D-(+)-malic acid, (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid).

Preferably a hydrochloride salt of an enantiomerically pure compound of general formula (7) (more preferably Ozanimod) is prepared in the additional and optional step k).

More preferably the optional step k) is carried out according to scheme k.1), said scheme k.1) comprising treating the enantiomerically pure amine of general formula (12) or the salt thereof, preferably an enantiomerically pure amine of formula (12A) or (12B) or a salt of any one of them, with a compound of formula (15) so as to provide an enantiomerically pure compound of general formula (7) or a salt thereof:

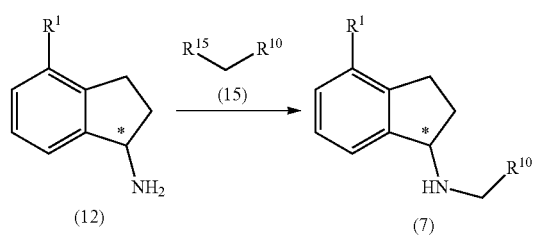

wherein the substituents assume the meanings reported above, and

R[15] is a leaving group able to undergo a nucleophilic substitution, such as for example, a mesylate, a tosylate, a nosylate, a triflate, a nonaflate, a fluorosulfonate, or a halogen.

Scheme k.1) can be performed by treating the enantiomerically pure amine of general formula (12) or the salt thereof, preferably an enantiomerically pure amine of formula (12A), (12B) or a salt of any one of them, with a compound of formula (15). Preferably scheme k.1) is carried out in the presence of a base, either organic or inorganic, optionally in an inert solvent such as, toluene, butyl acetate, tert-butyl methyl ether, chlorobenzene, chloroform, cyclohexane, dichloromethane, dichloroethane, di-tert-butyl ether, diethyl ether, diglyme, diisopropyl ether, fluorobenzene, heptane, hexane, and combinations thereof.

More preferably scheme k.1) is carried out in toluene, dichloromethane or a mixture thereof. More preferably this step comprises contacting the enantiomerically pure amine of general formula (12) or the salt thereof, preferably the enantiomerically pure amine of formula (12A), (12B) or a salt of any one of them, with a compound of formula (15A) (i.e. a compound of formula (15) in which R[10] is —CH$_2$OR[13] and R[13] assumes the meanings reported above) or a compound of formula (15B) (i.e. a compound of general formula (15) in which R[10] is —CO$_2$R[12] and R[12] assumes the meanings reported above) so as to provide an enantiomerically pure compound of formula (7A) and (7B), respectively, or a salt of any one of them.

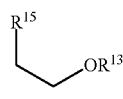
(15A)

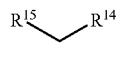
(15B)

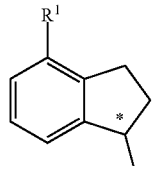
(7A)

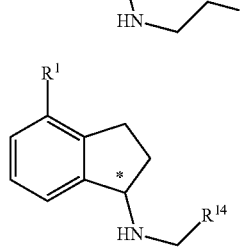
(7B)

More preferably the base used in scheme k.1) is a tertiary amine (cyclic or acyclic), such as triethylamine, N,N-diisopropylethylamine, N,N-diisopropylmethylamine, N-methylpyrrolidine, N-methylmorpholine, N,N-dicyclohexylmethylamine, N,N-diethylaniline, pyridine, 2-methylpyridine, 2,6-dimethylpyridine, 2,4,6-trimethylpyridine or 4-dimethylaminopyridine.

Even more preferably scheme k.1) is carried out by mixing at least one tertiary amine (preferably an acyclic tertiary amine, more preferably triethylamine or N,N-diisopropylethylamine), a compound of formula (15), (15A) or (15B) (preferably a solution of a compound of formula (15), (15A) or (15B) in an organic solvent compatible with the nitrogen alkylation step, as defined above) and an enantiomerically pure amine of general formula (12) or a salt thereof, preferably an enantiomerically pure amine of formula (12A), (12B) or a salt of any one of them, more preferably a dispersion of an enantiomerically pure amine of general formula (12), (12A) or (12B) in the same solvent used to solubilize the compound of formula (15), (15A) or (15B).

The molar ratio of the enantiomerically pure amine of general formula (12) to the compound of formula (15) may normally range from 1:1 to 1:5, preferably from 1:1 to 1:4.5, more preferably from 1:1 to 1:4, even more preferably from 1:1 to 1:3.5. In certain embodiments, the molar ratio of the enantiomerically pure amine of general formula (12) to the compound of formula (15) may be between and optionally includes any two of the following values: 1:1.05, 1:1.1, 1:1.15, 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8, 1:1.85, 1:1.9, 1:1.95, 1:2, 1:2.5, 1:3, or 1:3.5.

The molar ratio of the enantiomerically pure amine of general formula (12) to the base may normally range from 1:1 to 1:10. In certain embodiments, the molar ratio of the enantiomerically pure amine of general formula (12) to the base may be between and optionally includes any two of the following values: 1:1.05, 1:1.1, 1:1.15, 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8, 1:1.85, 1:1.9, 1:1.95, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

The volume of the inert solvent is normally from 1 mL to 50 mL per gram of the enantiomerically pure amine of general formula (12). Preferably the volume of the solvent is between and optionally includes any two of the following values: 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL or 45 mL per gram of the enantiomerically pure amine of general formula (12). More preferably said volume is from 3 mL to 10 mL per gram of the enantiomerically pure amine of general formula (12).

According to a more preferred embodiment of this aspect of the invention, optional step k) comprises converting an enantiomerically pure amine of formula (12A) or a salt thereof into an enantiomerically pure amine of formula (7'''') or a salt thereof according to synthetic scheme k.2, said scheme comprising the following steps:

k.2.1) treating an enantiomerically pure amine of formula (12A) or a salt thereof with a compound of formula (15) so as to form an enantiomerically pure compound of formula (7') or a salt thereof:

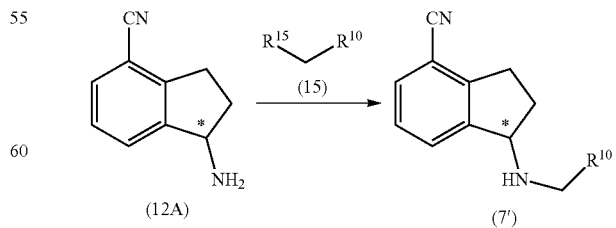

k.2.2) converting the enantiomerically pure compound of formula (7') or the salt thereof into an enantiomerically pure compound of formula (7''):

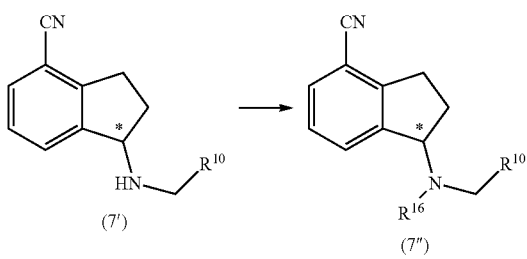

k.2.3) treating said enantiomerically pure compound of formula (7") with hydroxylamine or a salt thereof so as to provide an enantiomerically pure amidoxime of formula (5'), a tautomer or a salt thereof:

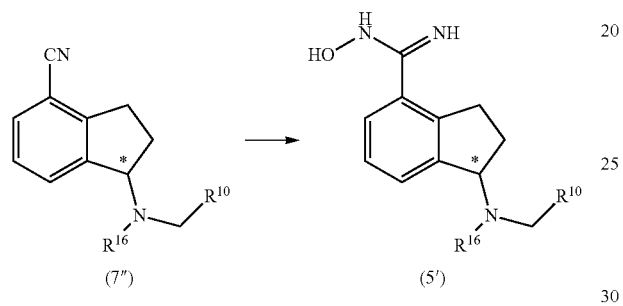

k.2.4) converting said enantiomerically pure amidoxime of formula (5'), the tautomer or the salt thereof, into an enantiomerically pure protected compound of formula (7'''):

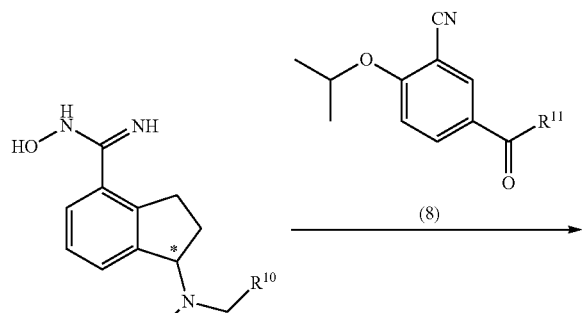

k.2.5) converting said enantiomerically pure protected compound of formula (7''') into an enantiomerically pure amine of formula (7'''') or a salt thereof:

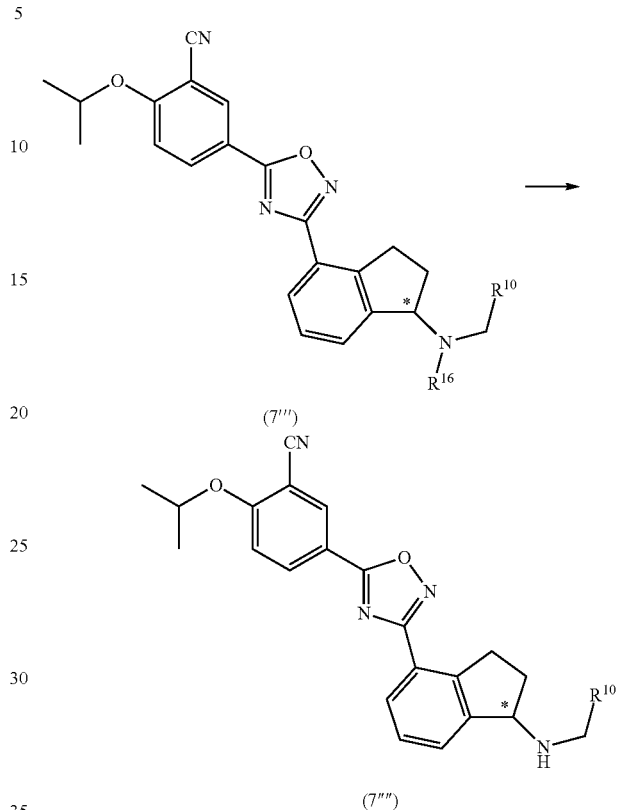

wherein the substituents assume the meanings reported above and $R^{16}$ is a nitrogen protecting group.

Step k.2.1) entails treating the enantiomerically pure amine of general formula (12A) or a salt thereof with a compound of formula (15), preferably a compound of formula (15A) or (15B) (as defined above), so as to form an enantiomerically pure compound of general formula (7'), (7A'), or (7B') respectively or a salt of any one of them.

Preferably this step is performed according to one of the procedures detailed above in respect of scheme k.1).

Step k.2.2) includes the treatment of the enantiomerically pure compound of general formula (7') or a salt thereof, preferably an enantiomerically pure compound of formula (7A'), (7B') or a salt of any one of them, with a nitrogen protecting agent so as to form an enantiomerically pure compound of formula (7"), preferably an enantiomerically pure compound of formula (7A1") or (7B1").

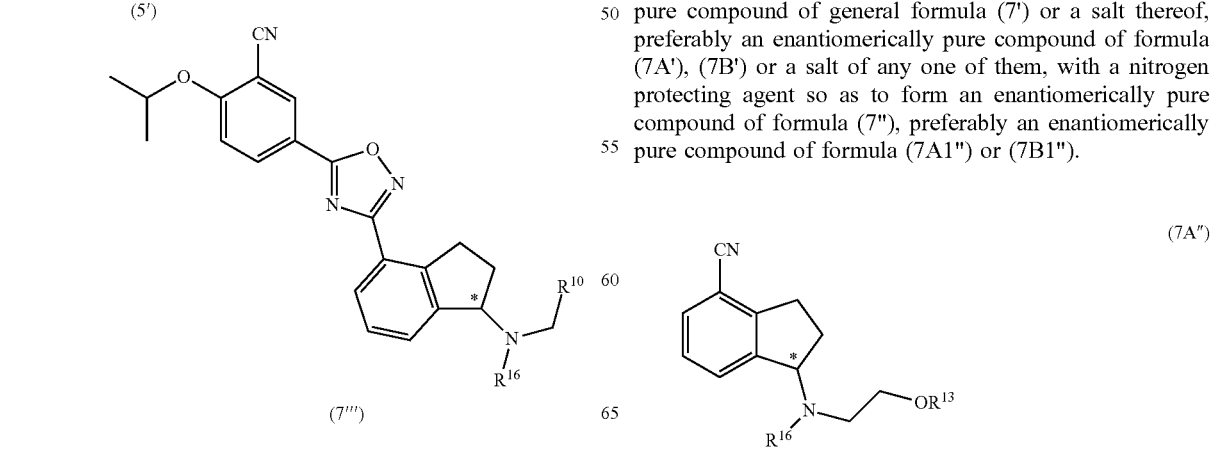

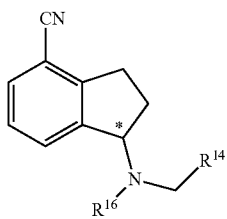

(7B'')

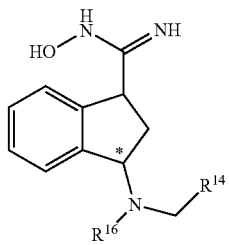

(5B¢)

Preferably this step is performed according to one of the procedures described in Theodora W. Green, *Protective Groups in Organic Synthesis*, John Wiley & Sons (1999). pages 503-598, which are herein incorporated by reference. More preferably this step is performed by treating the enantiomerically pure compound of general formula (7'), (7A'), (7B') or a salt of any one of them with a nitrogen protecting agent, preferably di-tert-butyldicarbonate (Boc$_2$O), benzyl chloroformate (CbzCl), N-(benzyloxycarbonyloxy)succinimide (Cbz-OSu) or dibenzyl dicarbonate (Cbz$_2$O). Optionally step k.2.2) is carried out in an aprotic polar solvent, such as dimethylacetamide, dimethylformamide, N-methylpyrrolidone, tetrahydrofuran, acetonitrile, ethyl acetate, or in a chlorinated solvent, such as dichloromethane, or a mixture thereof, optionally in the presence of a tertiary amine preferably triethylamine.

The molar ratio of the enantiomerically pure compound of formula (7') or the salt thereof to the nitrogen protecting agent may normally range from 1:1 to 1:5, preferably from 1:1 to 1:4.5, more preferably from 1:1 to 1:4, even more preferably from 1:1 to 1:3.5. In certain embodiments, the molar ratio of the enantiomerically pure amine of general formula (7') to the nitrogen protecting agent may be between and optionally includes any two of the following values: 1:1.05, 1:1.1, 1:1.15, 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8, 1:1.85, 1:1.9, 1:1.95, 1:2, 1:2.5 or 1:3.

The molar ratio of the enantiomerically pure compound of formula (7') to the tertiary amine, when used, may range from 1:1 to 1:10. In certain embodiments, the molar ratio of the enantiomerically pure compound of formula (7') to the tertiary amine may be between and optionally includes any two of the following values: 1:1.05, 1:1.10, 1:1.15, 1:1.20, 1:1.25, 1:1.30, 1:1.35, 1:1.40, 1:1.45, 1:1.50, 1:1.55, 1:1.60, 1:1.65, 1:1.70, 1:1.75, 1:1.80, 1:1.85, 1:1.9, 0 1:1.95, 1:2, 1:2.5, 1:3, 1:3.5, 1:4, 1:4.5, 1:5, 1:5.5, 1:6, 1:6.5, 1:7, 1:7.5, 1:8, 1:8.5, 1:9, or 1:9.5.

Step k.2.3) entails the treatment of the enantiomerically pure compound of formula (7'') (preferably an enantiomerically pure compound of formula (7A1'') or (7B1'')) with hydroxylamine or a salt thereof so as to provide an enantiomerically pure amidoxime of formula (5'), (5A') or (5B'), a tautomer or a salt of any one of them.

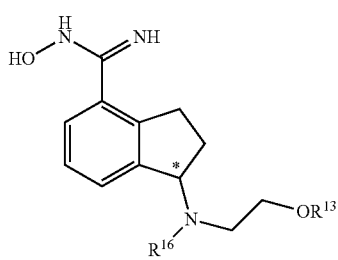

(5A¢)

Preferably this step is performed according to one of the procedures detailed above in respect of step d).

The enantiomerically pure amidoxime of formula (5'), the tautomer or the salt thereof, preferably an enantiomerically pure amidoxime of formula (5A') or (5B'), a tautomer or a salt of any one of them, is further converted into an enantiomerically pure protected compound of formula (7''') (preferably an enantiomerically pure protected compound of formula 7A''') or (7B''')) according to step k.2.4).

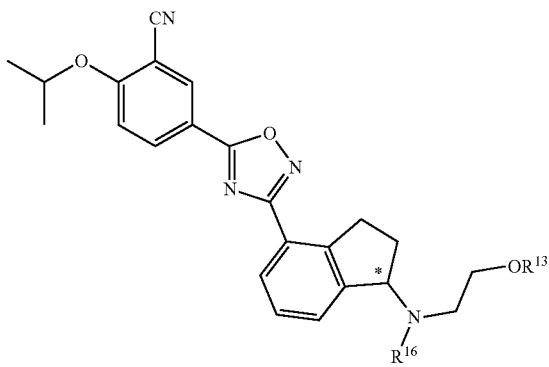

(7A''')

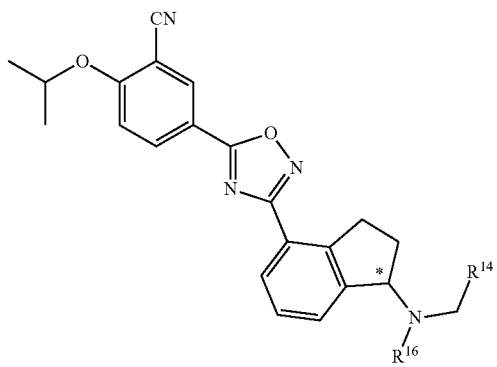

(7B''')

Preferably this step is performed by treatment with a compound of formula (8), more preferably according to one of the operations detailed above in respect of step e).

A variant of the process object of this aspect of the invention includes an additional and optional step k.2.4'), carried out after step k.2.4), comprising heating the mass resulting from the reaction between the compound of formula (8) and the enantiomerically pure amidoxime of formula (5') (5A'), (5B'), a tautomer or a salt of any one of them, preferably a mass comprising a compound of general formula (6''), (6A''), (6B''), a tautomer or a salt of any one of them, to a temperature from 50° C. to 120° C. so as to increase the rate of conversion into the enantiomerically pure protected compound of formula (7'''), (7A''') or (7B''').

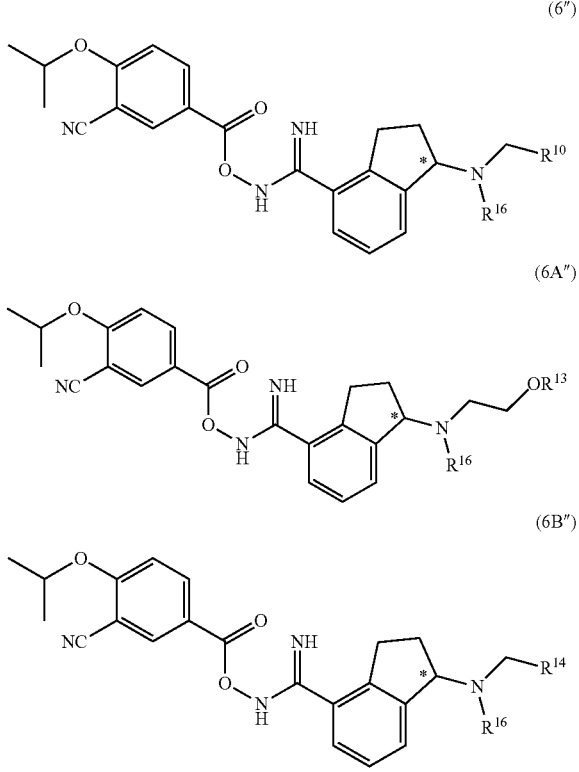

In an alternative embodiment of this aspect of the invention, an additional and optional step k.2.4") is carried out after either step k.2.4) or k.2.4'), comprising converting the enantiomerically pure protected compound of formula (7'''), (7A''') or (7B''') into an enantiomerically pure protected compound of formula (7C''').

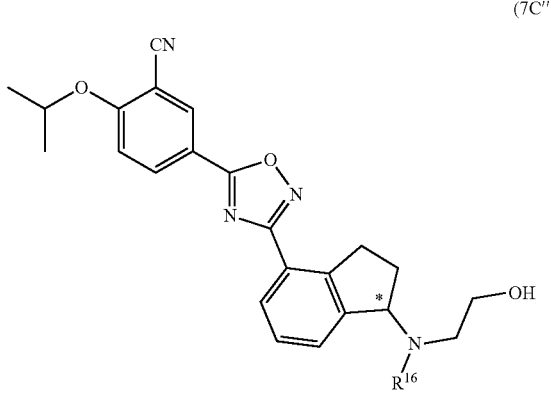

Preferably step k.2.4") is performed according to one of the procedures detailed above in respect of step g) (g.1) to g.5)).

The following step k.2.5), entails converting the enantiomerically pure protected compound of formula (7'''), preferably an enantiomerically pure protected compound of formula (7A'''), (7B''') or (7C'''), into an enantiomerically pure amine of formula (7''''), preferably an enantiomerically pure protected amine of formula (7A''), (7B''), or a salt of any one of them, more preferably ozanimod, even more preferably a hydrochloride salt of ozanimod.

Step k.2.5) can be performed using one of the methods known in the field to remove an amino protecting group, for example one of those described in Theodora W. Green, *Protective Groups in Organic Synthesis*, John Wiley & Sons (1999), pages 503-598, which are herein incorporated by reference. Preferably, in the case when Pg forms together with the nitrogen atom a carbamate group, said de-protection step may be operated according to the procedures detailed on pages 504-540 of the text referred to above. According to an even more preferred embodiment of this aspect of the invention, in the case when Pg is a benzyloxy carbonyl, step k.2.5) can be carried out by treatment with hydrogen in the presence of a catalyst (e.g. palladium, platinum or nickel) optionally supported on an appropriate carrier (such as carbon, barium sulfate or calcium carbonate) in an alcohol (preferably methanol or ethanol) or an aqueous mixture thereof. Conversely, when Pg is a tert-butoxy carbonyl, k.2.5) can be carried out according to one of the procedures described in Theodora W. Green, *Protective Groups in Organic Synthesis*, John Wiley & Sons (1999), pages 520-522. Preferably this step is performed by treating the enantiomerically pure protected indanone of formula (7'''), (7A''') or (7B''') with a solution of hydrogen chloride in water or in an organic solvent so as to provide a hydrochloride salt of an enantiomerically pure amine of formula (7''''), preferably hydrochloride salt of an enantiomerically pure amine of formula (7A'') or (7B''), more preferably a hydrochloride salt of ozanimod.

In a possible variant of this embodiment of the invention, an additional and optional step k.2.5') is carried out after step k.2.5), said step k.2.5') comprising converting the enantiomerically pure amine of formula (7'''') or the salt thereof, preferably an enantiomerically pure amine of formula (7A'') or (7B'') or a salt of any one of them, into ozanimod or a salt thereof, preferably a hydrochloride salt of ozanimod.

Preferably optional step k.2.5') is carried out according to one of the procedures detailed above in respect of step g) (g.1) to g.5)).

Compounds (1''), (3), (3A), (3B), (3A1), (3A2), (3A'), (3A''), (3B'), (3B''), (3A'''), (3A''''), (3B'''), (3B''''), (4), (4A), (4B), (4C), (5), (5A), (5B), (5B'), (5C), (5A1), (6), (6'), (6'A), (6'B), (6'C), (6A), (6B), (6B''), (6C), (6A1), (7A'), (7B'), (7A'') with the proviso that $R^{13}$ is different from H, (7B'') with the proviso that $R^{14}$ is different from $-CO_2H$, (8) with the proviso that $R^{11}$ is imidazole or a halogen and (13B) are novel and are a further object of the present invention. When anyone of the compounds described in the present application are obtained with a degree of chemical purity not suitable for the inclusion in a medicament, the processes object of the present invention entails a further step of purification, for example by means of chromatography or crystallization, optionally after formation of an addition compound, such as for example a salt (preferably a hydrochloride salt) or a co-crystal, or by washing with an organic solvent or an aqueous solution, optionally adjusting the pH.

The invention will be further illustrated by the following examples.

XRPD: Analyses were performed on an APD 2000 Ital Structures diffractometer, using a CuKα tube (35 kV, 30 mA, λ=1.5406 Å) as the X-ray source. Data collection was made in step scan mode and in Bragg-Brentano configuration in the range of 2° to 40°, sampling at 0.04° with 2 seconds acquisition time. Samples were accurately ground and placed in the hollow of an aluminium sampler. The instrument was previously calibrated by means of zinc oxide, then allowing acquisition and elaboration of data by means of WinAcq32 software. Laboratory temperature 25±5° C.

EXAMPLES

Example 1

Preparation of methyl 5',5'-dimethyl-2,3-dihydrospiro[indene-1,2'-[1,3]dioxane]-4-carbonitrile, compound of formula (4) wherein the dashed line indicates a single bond, and Y, together with the carbon atom to which it is bonded, forms a cyclic ketal.

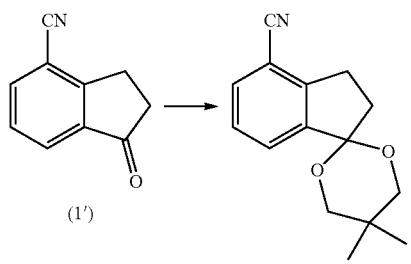 [SMILES: N#Cc1cccc2c1CCC2=O ; CC1(C)COC2(CCc3c(C#N)cccc32)OC1]

To a solution of 1-oxo-2,3-dihydro-1H-indene-4-carbonitrile (30 g, 0.19 mol) in toluene (200 mL), neopentyl glycol (19.6 g, 0.19 mol) and p-toluenesulfonic acid (0.72 g, 0.0038 mol) were added under stirring at 25° C. Trimethyl orthoformate (26.4 g, 0.24 mol) was added thereto and the mixture was maintained under stirring at 20-25° C. until complete conversion (about 12 hours). The reaction was cooled to 5° C., then a 10% aqueous solution of $Na_2CO_3$ (150 mL) and toluene (100 mL) were added thereto. The resulting phases were separated and the aqueous layer was extracted with toluene (80 mL). The collected organic phases were evaporated under reduced pressure up to obtain a residue which was triturated in 2-propanol (130 mL) for 1 hour. The resulting solid was filtered, washed with 2-propanol and dried at 40° C. under reduced pressure yielding 28.6 g of the title compound (yield: 62%).

$^1$H NMR (300 MHz, DMSO-$d_6$, δ ppm, J Hz) δ: 7.78 (dd, J=25.6, 7.6, 2H), 7.47 (t, J=7.7, 1H), 3.73 (d, J=11.2, 2H), 3.49 (d, J=11.2, 2H), 3.04 (t, J=6.9, 2H), 2.46 (d, J=6.9, 2H), 1.25 (s, 3H), 0.80 (s, 3H).

Example 2

Preparation of N-hydroxy-5',5'-dimethyl-2,3-dihydrospiro[indene-1,2'-[1,3]dioxane]-4-carboximidamide, compound of formula (5) wherein the dashed line indicates a single bond, and Y, together with the carbon atom to which it is bonded, forms a cyclic ketal.

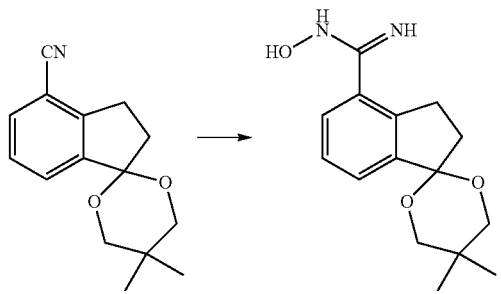 [SMILES: CC1(C)COC2(CCc3c(C#N)cccc32)OC1 ; CC1(C)COC2(CCc3c(C(=N)NO)cccc32)OC1]

To a dispersion of hydroxylamine hydrochloride (20.3 g, 292.2 mmol) in ethanol (490 mL), triethylamine (31.5 g, 311.7 mmol) was added. The mixture was maintained under stirring at 25° C. for one hour then methyl 5',5'-dimethyl-2,3-dihydrospiro[indene-1,2'-[1,3]dioxane]-4-carbonitrile (23.7 g, 97.4 mmol) was added thereto. The reaction was maintained under stirring at the same temperature until complete conversion (about 48 hours), then the resulting solid was filtered, washed with ethanol and dried at 40° C. under reduced pressure, thus yielding 20 g of the title compound (quantitative yield).

$^1$H NMR (500 MHz, DMSO-$d_6$, δ ppm, J Hz) δ: 9.55 (s, 1H), 7.47 (dd, J=7.6, 1.2, 1H), 7.41 (dd, J=7.6, 1.2, 1H), 7.28 (dd, J=8.0, 7.3, 1H), 5.72 (s, 2H), 3.71 (d, J=11.1, 2H), 3.47 (dt, J=11.3, 1.1, 2H), 3.02 (t, J=6.9, 2H), 2.34 (dd, J=7.4, 6.5, 2H), 1.26 (s, 3H), 0.78 (s, 3H).

Example 3

Preparation of 5-(3-(5',5'-dimethyl-2,3-dihydrospiro[indene-1,2'-[1,3]dioxan]-4-yl)-1,2,4-oxadiazol-5-yl)-2-isopropoxybenzonitrile, compound of formula (6) wherein the dashed line indicates a single bond, and Y, together with the carbon atom to which it is bonded, forms a cyclic ketal.

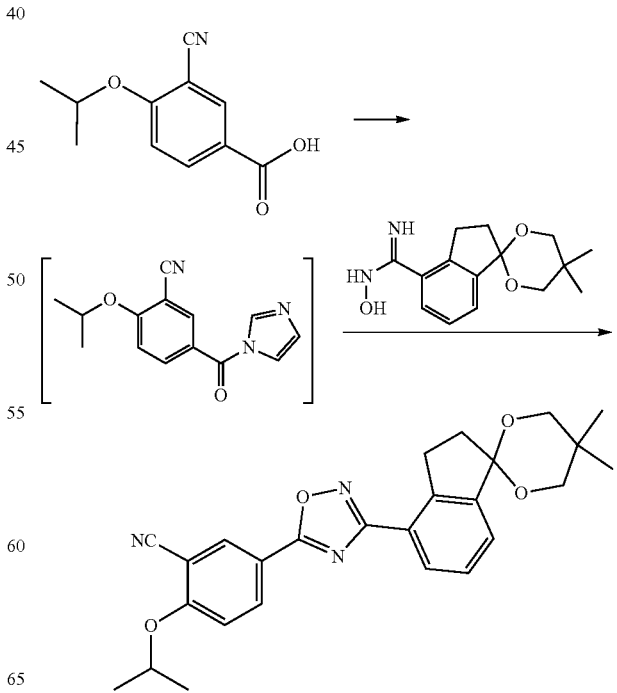

To a dispersion of 3-cyano-4-isopropoxybenzoic acid (17 g, 82.8 mmol) in cyclopentyl methyl ether (300 mL) heated to 55° C., 1,1'-carbonyldiimidazole (20.8 g, 128.3 mmol) was added portionwise. The mixture was maintained under stirring at the same temperature until complete conversion (about 1 hour), then N-hydroxy-5',5'-dimethyl-2,3-dihydrospiro[indene-1,2'-[1,3]dioxane]-4-carboximidamide (22.9 g, 82.8 mmol) was added thereto. The reaction was heated to 80° C. and maintained under stirring at the same temperature until complete conversion (about 12 hours). Then it was cooled to 60° C. Cyclopentyl methyl ether (200 mL) and a 0.5N aqueous solution of sodium hydroxide (200 mL) were added thereto. The resulting phases were separated at 50° C. and the organic layer was washed with water (200 mL) at the same temperature. The organic phase was evaporated under reduced pressure up to obtain a solid which was used in the next step without further manipulation.

$^1$H NMR (500 MHz, CDCl$_3$, δ ppm, J Hz) δ=8.46 (dd, J=14.3, 2.1, 1H), 8.22 (dd, J=7.7, 1.2, 1H), 7.76 (dd, J=7.6, 1.2, 1H), 7.49 (tt, J=7.6, 0.8, 1H), 7.15 (dd, J=12.3, 9.0, 2H), 4.86-4.83 (m, 1H), 3.87-3.82 (m, 2H), 3.63 (dt, J=11.5, 1.3, 2H), 2.85-2.80 (m, 2H), 2.57 (dd, J=7.4, 6.5, 2H), 1.50 (t, J=5.6, 6H), 0.94 (s, 3H), 0.87 (s, 3H).

Example 4

Preparation of 2-isopropoxy-5-(3-(1-oxo-2,3-dihydro-1H-inden-4-yl)-1,2,4-oxadiazol-5-yl)benzonitrile, Compound of Formula (1")

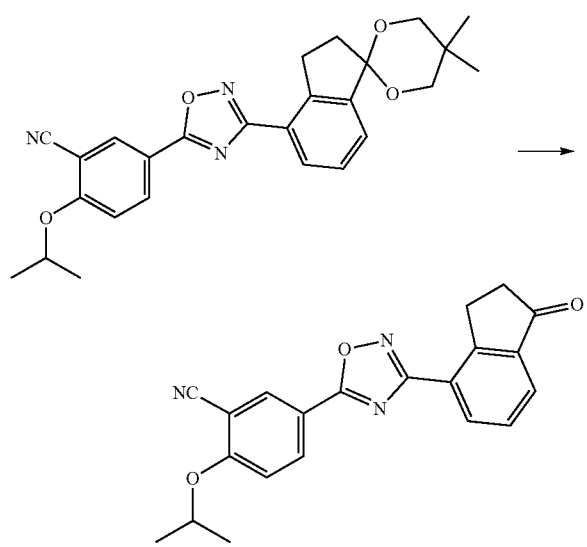

To a dispersion of 5-(3-(5',5'-dimethyl-2,3-dihydrospiro[indene-1,2'-[1,3]dioxan]-4-yl)-1,2,4-oxadiazol-5-yl)-2-isopropoxybenzonitrile (30 g, 67.3 mmol) in acetone (400 mL), p-toluenesulfonic acid (1.28 g, 6.73 mmol) was added. The mixture was maintained under stirring at 25° C. until complete conversion (about 2 hours), then the resulting solid was filtered, washed with acetone and dried at 45° C. under reduced pressure, thus yielding 22.6 g of the title compound (yield: 93%).

$^1$H NMR (500 MHz, CDCl$_3$, δ ppm, J Hz) δ: 8.50 (dd, J=7.6, 1.2, 1H), 8.47 (d, J=2.2, 1H), 8.38 (dd, J=8.9, 2.2, 1H), 7.96 (dd, J=7.6, 1.1, 1H), 7.60 (tt, J=7.6, 0.8, 1H), 7.16 (d, J=9.0, 1H), 4.88-4.79 (m, 1H), 3.61-3.55 (m, 2H), 2.86-2.80 (m, 2H), 1.51 (d, J=6.1, 6H).

Example 5

Preparation of 5-(3-(1-((2-hydroxyethyl)imino)-2,3-dihydro-1H-inden-4-yl)-1,2,4-oxadiazol-5-yl)-2-isopropoxybenzonitrile, compound of formula (3) wherein dashed line linked to R$^2$ indicates a double bond, R$^2$ is N, R$^{10}$ is —CH$_2$OH and R$^1$ is a 1,2,4-oxadiazole, said 1,2,4-oxadiazole being attached to the bicycle via carbon 3 and substituted in position 5 with a 3'-cyano-4'-isopropoxyphenyl group.

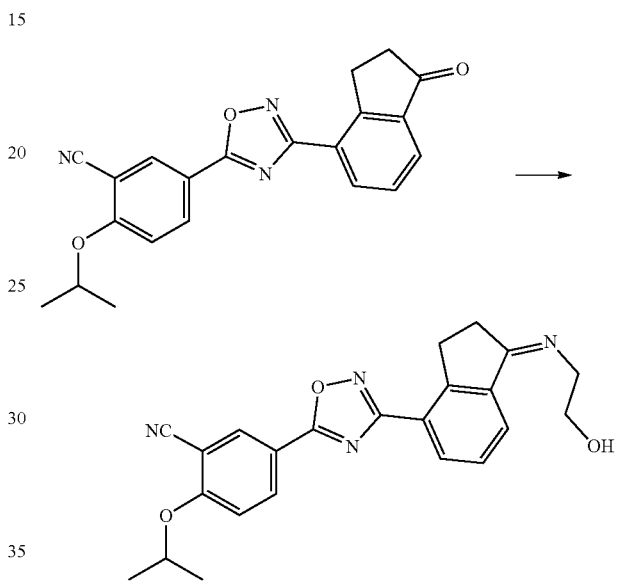

To a dispersion of 2-isopropoxy-5-(3-(1-oxo-2,3-dihydro-1H-inden-4-yl)-1,2,4-oxadiazol-5-yl)benzonitrile (500 mg, 1.39 mmol) in a 4:1 (V/V) mixture of toluene and ethanol (60 mL), p-toluenesulfonic acid (4.7 mg, 0.0247 mmol) and 2-aminoethanol (340 mg, 5.54 mmol) were added. The mixture was maintained under reflux conditions and the formed water distilled out using a Dean-Stark condenser containing activated 4A molecular sieves. The formation of a precipitate was observed during the course of the reaction. After complete conversion (about 12 hours), the mixture was cooled to 20-25° C. and the solid filtered, washed with toluene and dried at 40° C. under reduced pressure, thus yielding 540 mg of the title compound (yield: 96%).

$^1$H NMR (500 MHz, CDCl$_3$, δ ppm, J Hz) δ: 8.36 (d, J=2.1, 1H), 8.33 (dd, J=8.9, 2.2, 1H), 8.30 (dd, J=7.6, 1.2, 1H), 8.03 (dd, J=7.7, 1.1, 1H), 7.50 (dd, J=8.0, 7.2, 1H), 7.14 (d, J=8.9, 1H), 4.84 (hept, J=6.1, 1H), 4.04 (t, J=5.1, 2H), 3.64 (t, J=5.1, 2H), 3.40-3.33 (m, 2H), 2.81-2.74 (m, 2H), 1.51 (d, J=6.1, 6H)

Example 6

Preparation of racemic Ozanimod, compound of formula (7) wherein R$^2$ is NH, R$^{10}$ is —CH$_2$OH and R$^1$ is a 1,2,4-oxadiazole, said 1,2,4-oxadiazole being attached to the bicycle via carbon 3 and substituted in position 5 with a 3'-cyano-4'-isopropoxyphenyl group.

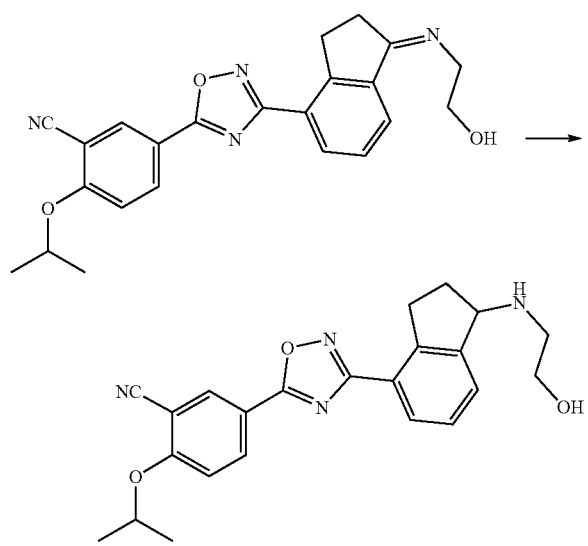

To a dispersion of 5-(3-(1-((2-hydroxyethyl)imino)-2,3-dihydro-1H-inden-4-yl)-1,2,4-oxadiazol-5-yl)-2-isopropoxybenzonitrile (100 mg, 0.25 mmol) in ethanol (1 mL) and dichloromethane (1 mL) maintained at 0° C., sodium borohydride (9.4 mg, 0.25 mmol) was added. The mixture was gently heated to 40° C. and maintained under stirring at the same temperature until complete conversion (about 1 hours). The mixture was cooled to 25° C. then water (5 mL) was added thereto. Dichloromethane and ethanol were evaporated under reduced pressure, then dichloromethane (10 mL) was added to the mixture. The phases were separated and the aqueous layer was counter-extracted with dichloromethane. The collected organic phases were evaporated under reduced pressure thus yielding 90 mg of the title compound (yield: 90%) with spectral data in accordance with those reported in EP 2291080 B1.

Example 7

Preparation of 1-((2-hydroxyethyl)imino)-2,3-dihydro-1H-indene-4-carbonitrile, compound of formula (3) wherein the dashed line linked to $R^2$ indicates a double bond, $R^2$ is N, $R^{10}$ is —CH$_2$OH and $R^1$ is —CN.

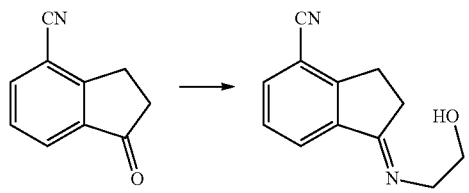 [SMILES: N#Cc1cccc2c1CCC2=O ; N#Cc1cccc2c1CC/C2=N\CCO]

To a dispersion of 1-oxo-2,3-dihydro-1H-indene-4-carbonitrile (2.0 g, 12.7 mmol) in methanol (20 mL), trimethyl orthoformate (1.6 g, 15.24 mmol) and 2-aminoethanol (816 mg, 13.37 mmol) were added. The mixture was maintained under stirring at 50° C. until complete conversion (about 3 hours), then it was evaporated under reduced pressure up to obtain a residue which was used in the next step without further manipulation.

Example 8

Preparation of 1-((2-hydroxyethyl)amino)-2,3-dihydro-1H-indene-4-carbonitrile, compound of formula (7) wherein $R^2$ is NH, $R^{10}$ is —CH$_2$OH and $R^1$ is —CN.

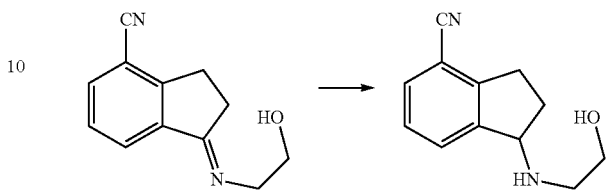

To a dispersion of the residue prepared in example 7 in methanol (20 mL) at 0° C., sodium borohydride (360 mg, 9.52 mmol) was added. The mixture was maintained under stirring at 25° C. until complete conversion (about 1 hour), then water (10 mL) was added thereto. Methanol was evaporated under reduced pressure, then dichloromethane (20 mL) was added to the mixture. The phases were separated and the aqueous layer was counter-extracted with dichloromethane. The organic layer was evaporated under reduced pressure up to obtain a dense oil which was used in the next step without further manipulation.

Example 9

Preparation of 1-((2-hydroxyethyl)amino)-2,3-dihydro-1H-indene-4-carbonitrile hydrochloride, hydrochloride salt of a compound of formula (7) wherein $R^2$ is NH, $R^{10}$ is —CH$_2$OH and $R^1$ is —CN.

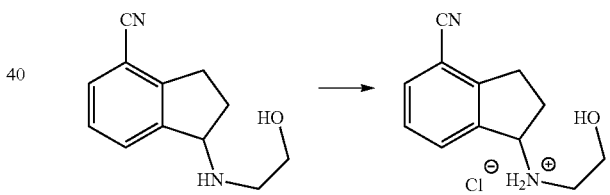

To a solution of the oil prepared in example 8 in methanol (10 mL) cooled to 5° C., a 12% (w/w) solution of hydrogen chloride in methanol (21.7 g, 59.5 mmol) was added. The mixture was maintained under stirring at 25° C. for 1 hour, then the resulting solid was filtered, washed with methanol and dried at 40° C. under reduced pressure, thus yielding 2.4 g of the title compound (yield: 79% over 3 steps).

$^1$H NMR (500 MHz, DMSO-d$_6$, δ ppm, J Hz) δ: 9.44 (s, 2H), 8.10 (d, J=7.7, 1H), 7.85 (dd, J=7.7, 0.9, 1H), 7.52 (t, J=7.7, 1H), 5.27 (t, J=5.2, 1H), 4.89 (dd, J=8.2, 4.6, 1H), 3.72 (q, J=5.3, 2H), 3.34-3.25 (m, 5H), 3.10-2.99 (m, 2H), 2.97 (dt, J=12.6, 5.5, 1H), 2.59-2.47 (m, 3H), 2.29 (ddt, J=13.8, 9.2, 4.9, 1H).

Example 10

Preparation of 1-((2-hydroxyethyl)imino)-2,3-dihydro-1H-indene-4-carbonitrile, compound of formula (3) wherein the dashed line linked to $R^2$ indicates a double bond, $R^2$ is N, $R^{10}$ is —CH$_2$OH and $R^1$ is —CN.

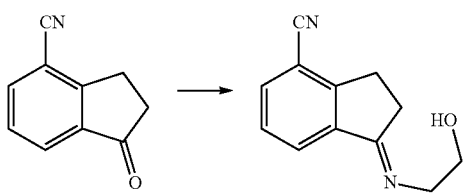 [SMILES: N#Cc1cccc2c1CCC2=O ; N#Cc1cccc2c1CC/C2=N\CCO]

To a solution of 1-oxo-2,3-dihydro-1H-indene-4-carbonitrile (600 mg, 3.82 mmol) in benzene (25 mL), 2-aminoethanol (233 mg, 3.82 mmol) and p-toluenesulfonic acid (7.2 mg, 0.0382 mmol) were added. The mixture was maintained under reflux conditions and the formed water distilled out using a Dean-Stark condenser containing activated 4A molecular sieves. After complete conversion (about 16 hours), the mixture was cooled to 25° C. and evaporated under reduced pressure. The resulting crude was dissolved in ethyl acetate (10 mL) and precipitated by adding petroleum ether (40 mL) thereto. The solid was filtered, washed with petroleum ether and dried under reduced pressure so as to provide 600 mg of the title compound (yield: 80%).

$^1$H NMR (400 MHz, CDCl$_3$, δ ppm, J Hz) δ: 7.96 (d, J=7.6, 1H), 7.63 (d, J=8.0, 1H), 7.34 (t, J=7.6, 1H), 3.90 (t, J=5.2, 2H), 3.53 (m, 2H), 3.19 (t, J=6.0, 2H), 2.74 (t, J=6.0, 2H), 2.48 (bs, 1H).

Example 11

Preparation of methyl 5',5'-dimethyl-2,3-dihydrospiro[indene-1,2'-[1,3]dioxane]-4-carbonitrile, compound of formula (4) wherein the dashed line indicates a single bond, and Y, together with the carbon atom to which it is bonded, forms a cyclic ketal.

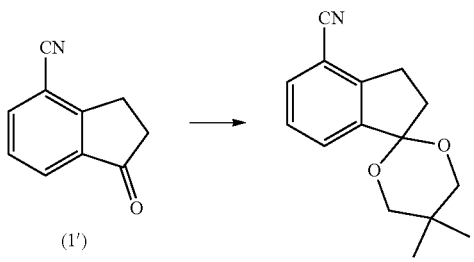 [SMILES: N#Cc1cccc2c1CCC2=O ; CC1(C)COC2(CCc3c(C#N)cccc32)OC1]

To a dispersion of 1-oxo-2,3-dihydro-1H-indene-4-carbonitrile (15 g, 95.5 mmol) in 2-propanol (60 mL), neopentyl glycol (14.9 g, 143.2 mmol) and p-toluenesulfonic acid (0.36 g, 1.91 mmol) were added under stirring at 25° C. Trimethyl orthoformate (13.2 g, 124.2 mmol) was added thereto and the mixture was maintained under stirring at 20-25° C. until complete conversion (about 6 hours). The reaction was cooled to 0° C. and maintained under stirring at the same temperature for 30 minutes. The resulting precipitate was filtered, washed with 2-propanol and dried under reduced pressure so as to provide 21.6 g of the title compound (yield: 93%) with spectral data in accordance with those reported in example 1.

Example 12

Preparation of Ozanimod, (S) enantiomer of the compound of formula (7) wherein R$^2$ is NH, R$^{10}$ is —CH$_2$OH and R$^1$ is a 1,2,4-oxadiazole, said 1,2,4-oxadiazole being attached to the bicycle via carbon 3 and substituted in position 5 with a 3'-cyano-4'-isopropoxyphenyl group.

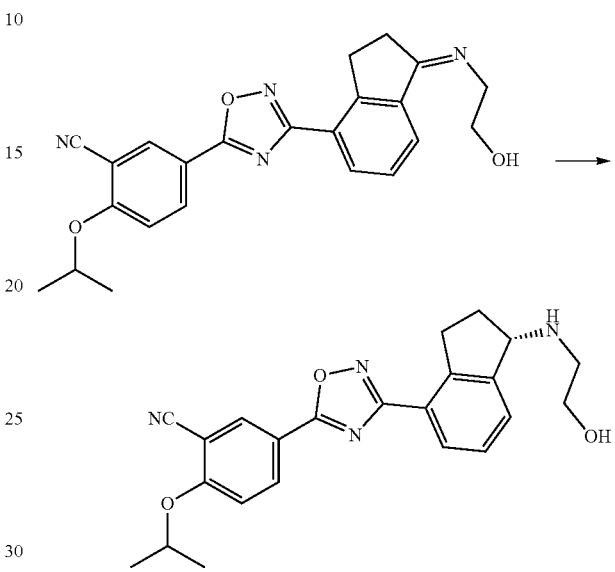

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C3-[(S,S)-teth-MtsDPEN RuCl] (1.6 mg, 0.0025 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=99%.

Example 13

Preparation of Ozanimod, (S) enantiomer of the compound of formula (7) wherein R$^2$ is NH, R$^{10}$ is —CH$_2$OH and R$^1$ is a 1,2,4-oxadiazole, said 1,2,4-oxadiazole being attached to the bicycle via carbon 3 and substituted in position 5 with a 3'-cyano-4'-isopropoxyphenyl group.

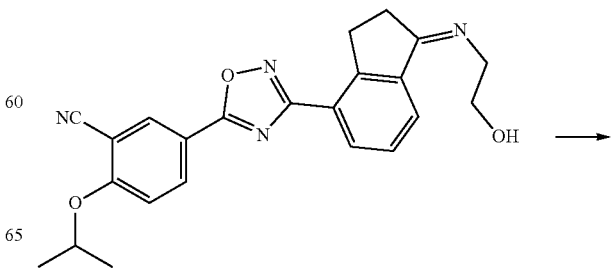

-continued

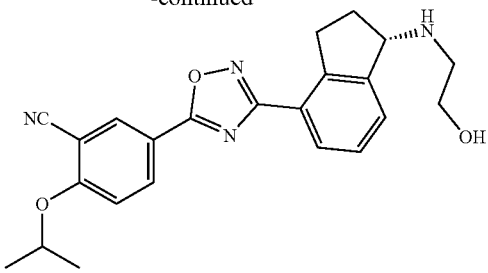

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C3-[(S,S)-teth-TrisDPEN RuCl] (1.8 mg, 0.0025 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)>99%.

Example 14

Preparation of Ozanimod, (S) enantiomer of the compound of formula (7) wherein $R^2$ is NH, $R^{10}$ is —$CH_2OH$ and $R^1$ is a 1,2,4-oxadiazole, said 1,2,4-oxadiazole being attached to the bicycle via carbon 3 and substituted in position 5 with a 3'-cyano-4'-isopropoxyphenyl group.

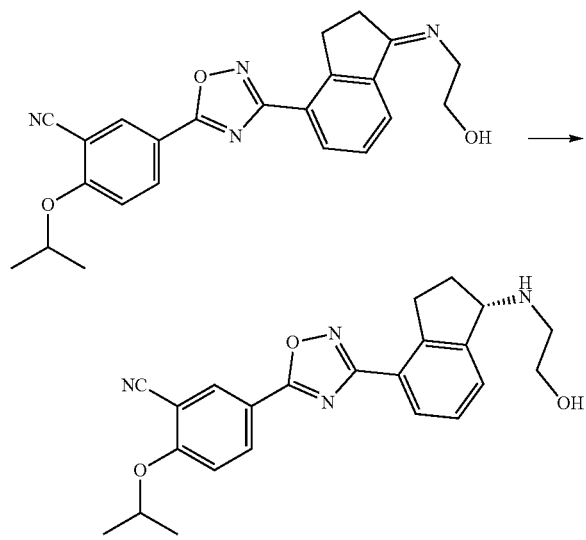

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C4-[(S,S)-teth-TsDPEN RuCl] (1.6 mg, 0.0025 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=90%.

Example 15

Preparation of Ozanimod, (S) enantiomer of the compound of formula (7) wherein $R^2$ is NH, $R^{10}$ is —$CH_2OH$ and $R^1$ is a 1,2,4-oxadiazole, said 1,2,4-oxadiazole being attached to the bicycle via carbon 3 and substituted in position 5 with a 3'-cyano-4'-isopropoxyphenyl group.

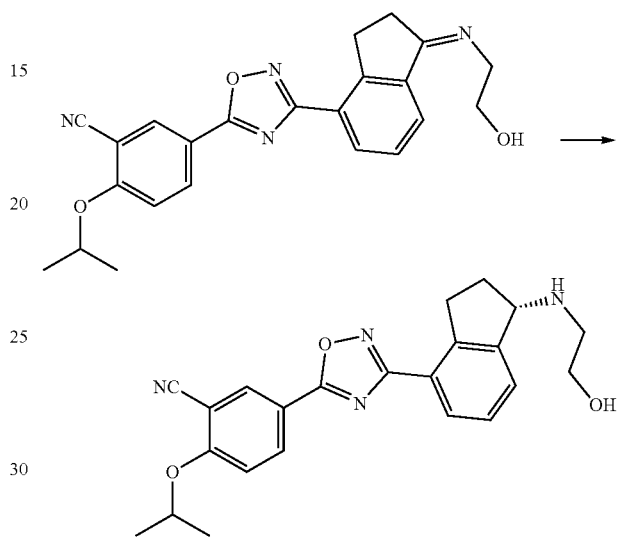

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C4-[(S,S)-teth-TrisDPEN RuCl] (1.9 mg, 0.0025 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=98%.

Example 16

Preparation of Ozanimod, (S) enantiomer of the compound of formula (7) wherein $R^2$ is NH, $R^{10}$ is —$CH_2OH$ and $R^1$ is a 1,2,4-oxadiazole, said 1,2,4-oxadiazole being attached to the bicycle via carbon 3 and substituted in position 5 with a 3'-cyano-4'-isopropoxyphenyl group.

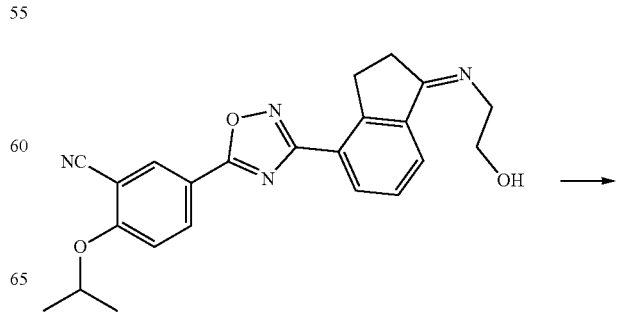

-continued

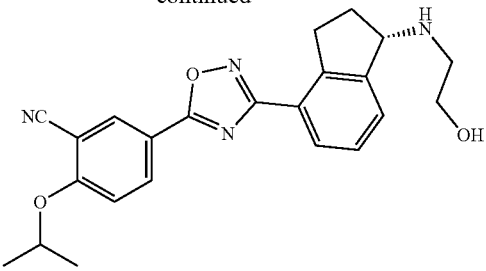

To a dispersion of 5-(3-(1-((2-hydroxyethyl)imino)-2,3-dihydro-1H-inden-4-yl)-1,2,4-oxadiazol-5-yl)-2-isopropoxybenzonitrile (150 mg, 0.37 mmol) in 2,2,2-trifluoroethanol (3 mL), C3-[(S,S)-teth-MtsDPEN RuCl] (1.2 mg, 0.0019 mmol) and formic acid triethylamine complex 5:2 (161 mg, 1.86 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=99%.

Example 17

Preparation of Ozanimod, (S) enantiomer of the compound of formula (7) wherein $R^2$ is NH, $R^{10}$ is —CH$_2$OH and $R^1$ is a 1,2,4-oxadiazole, said 1,2,4-oxadiazole being attached to the bicycle via carbon 3 and substituted in position 5 with a 3'-cyano-4'-isopropoxyphenyl group.

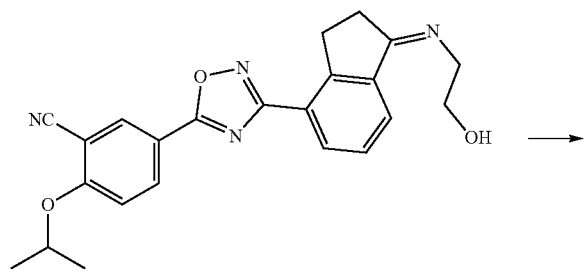

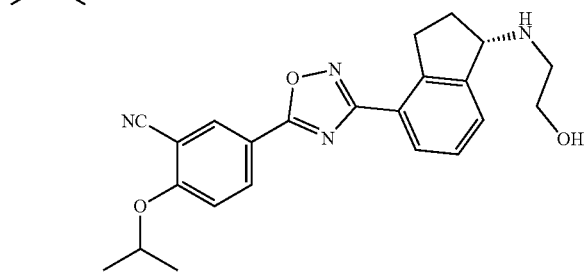

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C3-[(S,S)-teth-TsDPEN RuCl] (1.5 mg, 0.0025 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=88%.

Example 18

Preparation of Ozanimod, (S) enantiomer of the compound of formula (7) wherein $R^2$ is NH, $R^{10}$ is —CH$_2$OH and $R^1$ is a 1,2,4-oxadiazole, said 1,2,4-oxadiazole being attached to the bicycle via carbon 3 and substituted in position 5 with a 3'-cyano-4'-isopropoxyphenyl group.

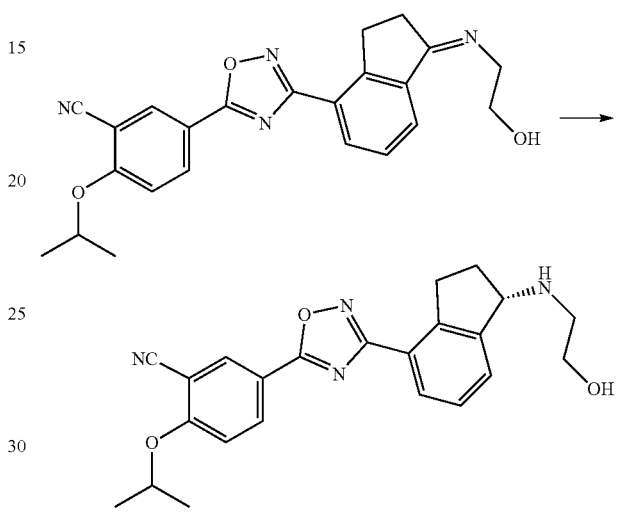

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C3-[(S,S)-teth-MsDPEN RuCl] (1.4 mg, 0.0025 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=86%.

Example 19

Preparation of Ozanimod, (S) enantiomer of the compound of formula (7) wherein $R^2$ is NH, $R^{10}$ is —CH$_2$OH and $R^1$ is a 1,2,4-oxadiazole, said 1,2,4-oxadiazole being attached to the bicycle via carbon 3 and substituted in position 5 with a 3'-cyano-4'-isopropoxyphenyl group.

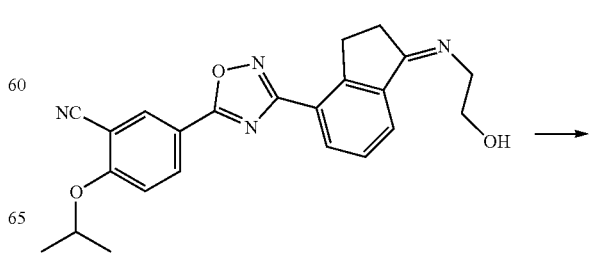

-continued

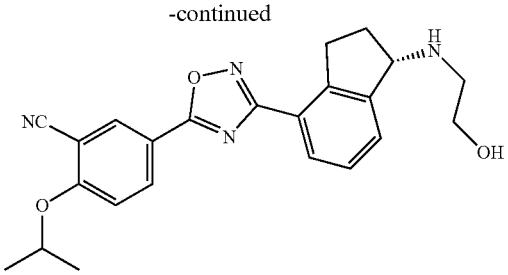

To a dispersion of 5-(3-(1-((2-hydroxyethyl)imino)-2,3-dihydro-1H-inden-4-yl)-1,2,4-oxadiazol-5-yl)-2-isopropoxybenzonitrile (100 mg, 0.25 mmol) in tetrahydrofuran (2.5 mL), (R)-H-[P(R)-H8-BINOL]-BoPhoz (7.3 mg, 0.01 mmol), iodine (3.1 mg, 0.025 mmol) and [Ir(COD)Cl]$_2$ (3.3 mg, 0.005 mmol) were added. After 3 cycles of vacuum/nitrogen and 3 cycles of vacuum/hydrogen, the mixture was pressurized to 30 bar of hydrogen heated to 50° C. and maintained under stirring at the same temperature until complete conversion (about 24 hours). The reaction was cooled to 20-25° C., purged with nitrogen, and diluted with methanol. An aliquot of the mixture was analysed by HPLC according to the method described in paragraph [0372] of WO 2011/060392 showing an enantiomeric excess (ee) =71%.

Example 20

Preparation of Ozanimod Hydrochloride.

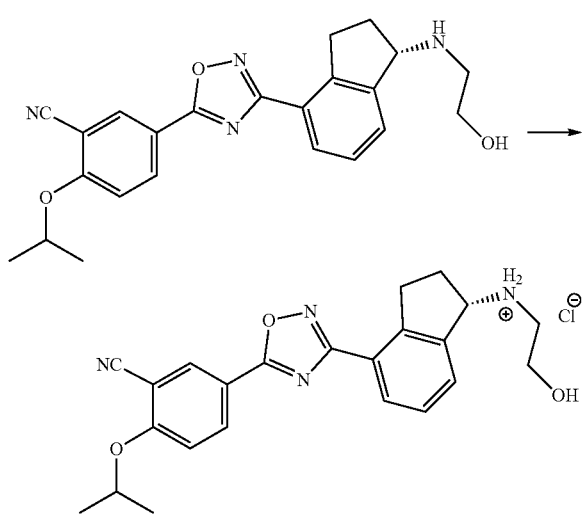

To a dispersion of Ozanimod (9.8 g, 24.8 mmol) in methanol (142 mL) cooled to 5° C., a 10% (w/w) solution of hydrogen chloride in methanol (13.3 g, 36.4 mmol) was added. The mixture was heated to 45° C. and maintained under stirring for 2 hours. Then it was slowly cooled to 25° C. and maintained under stirring at the same temperature for 1 hour. The resulting solid was filtered, washed with methanol and dried under reduced pressure so as to provide 10.3 g of the title compound (yield: 96%) with spectral data in accordance with those reported in paragraph [0372] of WO 2011/060392.

Example 21

Preparation of Ozanimod, (S) enantiomer of the compound of formula (7) wherein $R^2$ is NH, $R^{10}$ is —CH$_2$OH and $R^1$ is a 1,2,4-oxadiazole, said 1,2,4-oxadiazole being attached to the bicycle via carbon 3 and substituted in position 5 with a 3'-cyano-4'-isopropoxyphenyl group.

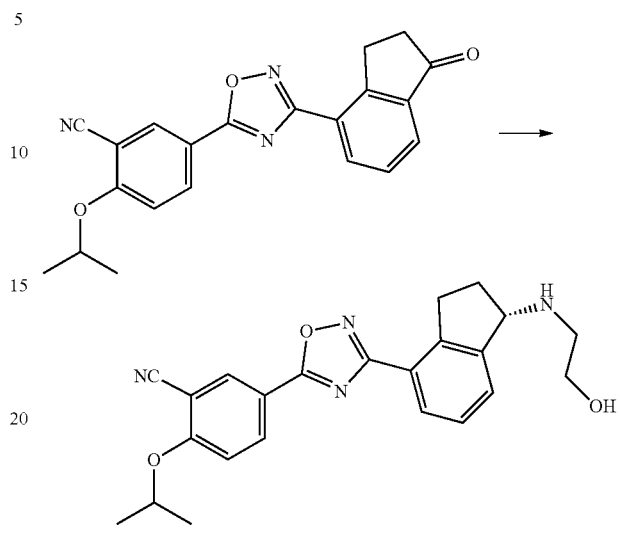

To a dispersion of 2-isopropoxy-5-(3-(1-oxo-2,3-dihydro-1H-inden-4-yl)-1,2,4-oxadiazol-5-yl)benzonitrile (50 mg, 0.14 mmol) in 2,2,2-trifluoroethanol (1 mL), C3-[(S,S)-teth-TrisDPEN RuCl] (2.0 mg, 0.0028 mmol), 2-aminoethanol (17.0 mg, 0.28 mmol) and formic acid triethylamine complex 5:2 (60.2 mg, 0.70 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)>99%.

Example 22

Preparation of Ozanimod, (S) enantiomer of the compound of formula (7) wherein $R^2$ is NH, $R^{10}$ is —CH$_2$OH and $R^1$ is a 1,2,4-oxadiazole, said 1,2,4-oxadiazole being attached to the bicycle via carbon 3 and substituted in position 5 with a 3'-cyano-4'-isopropoxyphenyl group.

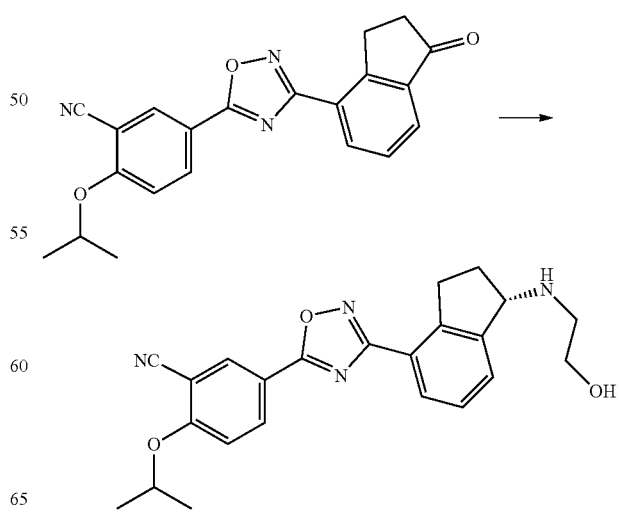

To a dispersion of 2-isopropoxy-5-(3-(1-oxo-2,3-dihydro-1H-inden-4-yl)-1,2,4-oxadiazol-5-yl)benzonitrile (50 mg, 0.14 mmol) in 2,2,2-trifluoroethanol (1 mL), C3-[(S,S)-teth-TsDPEN RuCl] (1.7 mg, 0.0028 mmol), 2-aminoethanol (17.0 mg, 0.28 mmol) and formic acid triethylamine complex 5:2 (60.2 mg, 0.70 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=90%.

Example 23

Preparation of Ozanimod, (S) enantiomer of the compound of formula (7) wherein $R^2$ is NH, $R^{10}$ is —CH$_2$OH and $R^1$ is a 1,2,4-oxadiazole, said 1,2,4-oxadiazole being attached to the bicycle via carbon 3 and substituted in position 5 with a 3'-cyano-4'-isopropoxyphenyl group.

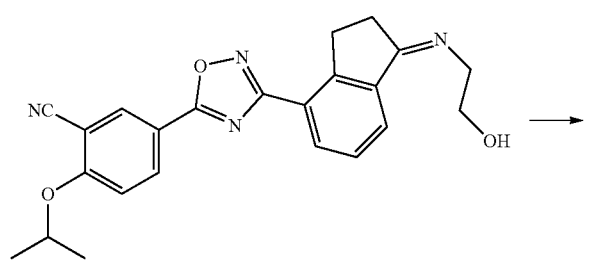

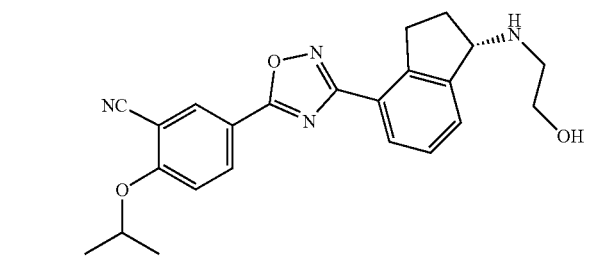

To a dispersion of 5-(3-(1-((2-hydroxyethyl)imino)-2,3-dihydro-1H-inden-4-yl)-1,2,4-oxadiazol-5-yl)-2-isopropoxybenzonitrile (50 mg, 0.12 mmol) in 2,2,2-trifluoroethanol (1 mL), C3-[(S,S)-teth-MtsDPEN RuCl] (1.6 mg, 0.0025 mmol), 2-aminoethanol (7.6 mg, 0.12 mmol) and formic acid triethylamine complex 5:2 (53.7 mg, 0.62 mmol) were added under stirring at 25° C. The mixture was maintained under stirring at 50° C. until complete conversion (about 24 hours), then it was cooled to 20-25° C. and diluted with methanol. An aliquot of the mixture was analysed by HPLC according to the method described in paragraph [0372] of WO 2011/060392 showing an enantiomeric excess (ee)=99%.

Example 24

Preparation of (S)-1-amino-2,3-dihydro-1H-indene-4-carbonitrile, compound of formula (12) wherein $R^1$ is —CN.

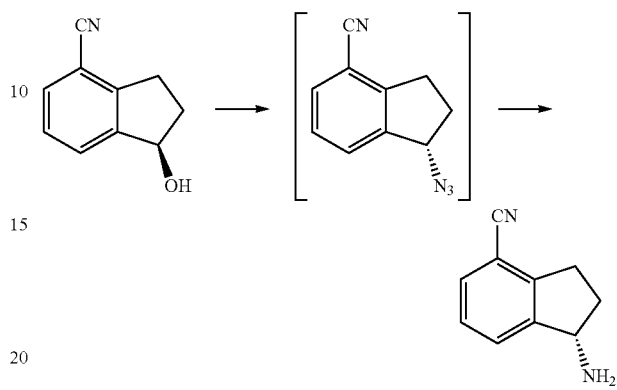

To a solution of (R)-1-hydroxy-2,3-dihydro-1H-indene-4-carbonitrile (5.0 g, 31.4 mmol, enantiomeric ratio R:S=96.5:3.5) in tetrahydrofuran (25 mL) and toluene (50 mL), diphenylphosphoryl azide (10.4 g, 37.7 mmol) was added at 25° C. 1,5-Diazabiciclo(5.4.0)undec-7-ene (6.2 g, 40.8 mmol) was added thereto monitoring that internal temperature does not exceed 25° C. The reaction was maintained under stirring at 25° C. until complete conversion into (S)-1-azido-2,3-dihydro-1H-indene-4-carbonitrile (about 10 hours), then triphenyl phosphine (10.9 g, 41.5 mmol) was added thereto. After complete $N_2$ evolution (about 10 hours), water (75 mL) was added thereto. The reaction was maintained under stirring at 50° C. until complete conversion (about 15 hours), then a 32% (w/w) aqueous solution of sodium hydroxide was added up to obtain a pH>12. The phases were separated and the organic layer was washed with water. Formic acid and water were added up to achieve a pH between 3.5-4, then the phases were separated. The aqueous phase was washed with toluene. 2-methyltetrahydrofuran and a 32% (w/w) aqueous solution of sodium hydroxide were added to the aqueous phase up to obtain a pH>10. The phases were separated and the organic layer was washed with water.

The organic phase was evaporated under reduced pressure so as to provide 8 g of the title compound which was used in the next step without further manipulation (quantitative yield).

Example 25

Preparation of the (L)-(+)-hemitartrate salt of (S)-1-amino-2,3-dihydro-1H-indene-4-carbonitrile, compound of formula (12) wherein $R^1$ is —CN.

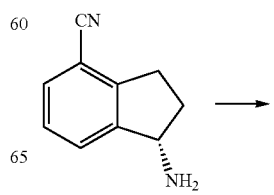

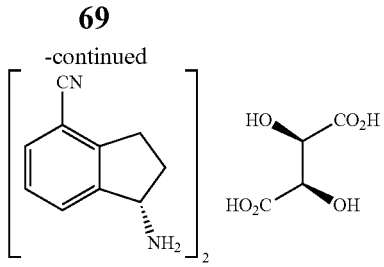

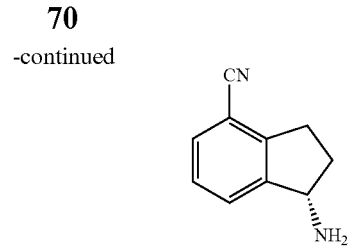

To a solution of (S)-1-amino-2,3-dihydro-1H-indene-4-carbonitrile prepared as described in example 24 in methanol (25 mL) heated to 50° C., a solution of (L)-(+)-tartaric acid (2.6 g, 17.5 mmol) in methanol (12.5 mL) was added. At the end of the addition, the mixture was maintained under stirring at 50° C. for about 30 minutes then cooled to 20° C. The resulting solid was filtered, washed with methanol and dried at 45° C. under reduced pressure thus yielding 7.6 g (yield: 52%, with respect to (R)-1-hydroxy-2,3-dihydro-1H-indene-4-carbonitrile) of the title compound with an enatiomeric ratio S:R=99.99:0.01 (determined according to paragraph [308] of WO 2011/060392).

To a suspension of (L)-(+)-hemitartrate salt of (S)-1-amino-2,3-dihydro-1H-indene-4-carbonitrile prepared as described in example 25 (11.0 g, 47.2 mmol) in dichloromethane (121 mL), a 10% (w/w) solution of potassium carbonate in water (163.2 g, 118.1 mmmol) was added at 25° C. The mixture was maintained under stirring at the same temperature until complete deblocking (about 15 minutes), then the phases were separated. The aqueous layer was counter-extracted with dichloromethane. The collected organic phases were evaporated under reduced pressure thus yielding 6.6 g of the title compound (yield: 88%).

$^1$H NMR (400 MHz, CDCl$_3$, δ ppm, J Hz): δ 7.42 (d, J=7.6, 1H), 7.28 (d, J=7.6, 1H), 7.13 (t, J=7.6, 1H), 4.24 (t, J=7.6, 1H), 3.00-2.93 (m, 1H), 2.79-2.70 (m, 1H), 2.44-2.37 (m, 1H), 1.93 (bs, 2H), 1.60 (dq, J=13.6, 8.8, 1H).

Example 26

Crystallization of the (L)-(+)-hemitartrate salt of (S)-1-amino-2,3-dihydro-1H-indene-4-carbonitrile, compound of formula (12) wherein R$^1$ is —CN.

A suspension of (L)-(+)-hemitartrate salt of (S)-1-amino-2,3-dihydro-1H-indene-4-carbonitrile (34.3 g, 73.5 mmol) with an enantiomeric ratio S:R=93.2:6.8 in methanol (275 mL) was heated to reflux conditions (about 70° C.). Water (about 75 mL) was slowly added up to obtain a solution. The mixture was cooled to 50° C. thus allowing crystallization of the title product. After 1 hour at 50° C. the mixture was cooled to 25° C. and maintained under stirring for 1 hour then cooled to 0° C. and kept at this temperature for 1 additional hour. The solid was filtered, washed with methanol and dried at 45° C. under reduced pressure thus yielding 28.4 g of the title compound with an enatiomeric ratio S:R=99.99:0.01 (determined according to paragraph [308] of WO 2011/060392).

An aliquot of the solid was analysed by XRPD, obtaining the diffractogram shown in FIG. 1.

$^1$H NMR (500 MHz, CDCl$_3$, δ ppm, J Hz) δ: 7.84 (dd, J=7.7, 1.0, 1H), 7.74 (dt, J=7.7, 0.8, 1H), 7.46 (t, J=7.7, 1H), 4.62 (t, J=7.1, 1H), 3.89 (s, 1H), 3.19-3.09 (m, 1H), 2.98 (dt, J=16.4, 7.9, 1H), 2.56-2.45 (m, 2H), 2.00-1.89 (m, 1H).

Example 27

Preparation of (S)-1-amino-2,3-dihydro-1H-indene-4-carbonitrile, compound of formula (12) wherein R$^1$ is —CN.

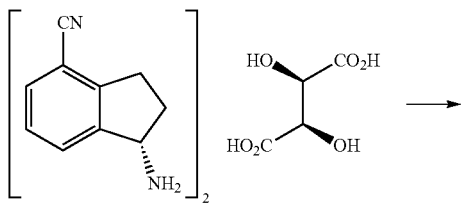

Example 28

Preparation of methyl (S)-(4-cyano-2,3-dihydro-1H-inden-1-yl)glycinate, compound of formula (7') wherein R$^{10}$ is —CO$_2$Me.

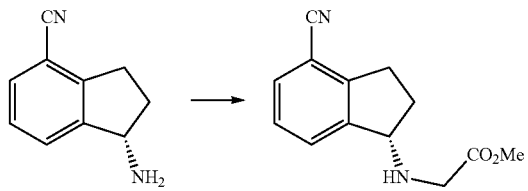 [SMILES: N#Cc1cccc2c1CC[C@@H]2N ; COC(=O)CN[C@H]1CCc2c(C#N)cccc21]

To a suspension of (S)-1-amino-2,3-dihydro-1H-indene-4-carbonitrile (500 mg, 3.2 mmol) in dichloromethane (3 mL), N-ethyldiisopropylamine (531 mg, 4.1 mmol) and a solution of methyl bromoacetate (581 mg, 3.8 mmol) in dichloromethane (2 mL) were added. The mixture was maintained under stirring at 25° C. until complete conversion (about 48 hours), then water (5 mL) and 4N hydrochloric acid (1 mL) were added so as to obtain a pH<2. The layers were separated and the aqueous phase was washed with dichloromethane. The pH of the aqueous layer was adjusted to 7-7.5 with a 5N aqueous solution of sodium hydroxide (0.8 mL). The phases were separated and the aqueous phase was extracted with dichloromethane. The collected organic phases were evaporated under reduced pressure thus yielding 553 mg of the title compound as a brown oil (yield: 76%).

$^1$H NMR (500 MHz, CDCl$_3$, δ ppm, J Hz): δ 7.61-7.48 (m, 2H), 7.32 (tt, J=7.6, 0.8, 2H), 4.34 (t, J=6.5, 1H), 3.77 (s, 3H), 3.59-3.43 (m, 3H), 3.23 (ddd, J=16.9, 8.6, 5.1, 1H), 3.06-2.95 (m, 1H), 2.45 (dddd, J=13.4, 8.4, 7.0, 5.1, 1H), 1.95 (dddd, J=12.8, 8.6, 6.7, 5.9, 2H).

Example 29

Preparation of methyl (S)—N-(tert-butoxycarbonyl)-N-(4-cyano-2,3-dihydro-1H-inden-1-yl)glycinate, compound of formula (7") wherein R$^{10}$ is —CO$_2$Me and R$^{16}$ is —C(O)OtBu.

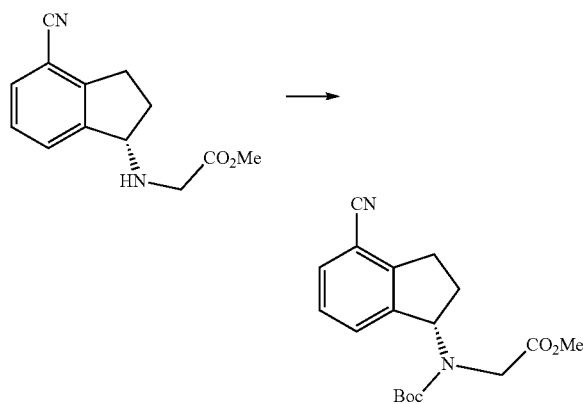

To a solution of methyl (S)-(4-cyano-2,3-dihydro-1H-inden-1-yl)glycinate (1.9 g, 8.2 mmol) in dichloromethane (19 mL), triethylamine (1.2 g, 12.3 mmol) and di-tert-butyl dicarbonate (2.1 g, 9.8 mmol) were added. At the end of the addition, the mixture was maintained under stirring at 25° C. until complete conversion (about 12 hours). After adding water (28 mL) the layers were separated and the organic phase was washed with water. The organic phase was evaporated under reduced pressure and ethanol (19 mL) and imidazole (559 mg, 8.2 mmol) were added thereto. The mixture was maintained under stirring at 25° C. for 30 minutes, then it was evaporated under reduced pressure. Dichloromethane (15 mL) and 1% (w/w) hydrochloric acid (25 mL) were added to the residue. The phases were separated and the organic layer was washed with 1% (w/w) hydrochloric acid and water. The organic layer was evaporated under reduced pressure thus yielding 2.5 g of the title compound as a brown oil (yield: 92%).

$^1$H NMR (500 MHz, CDCl$_3$, δ ppm, J Hz): δ 7.60-7.50 (m, 2H), 7.33 (td, J=7.7, 3.7, 1H), 5.28 (dt, J=27.7, 8.4, 1H), 3.75 (d, J=6.2, 1H), 3.19 (dtd, J=16.7, 8.3, 3.3, 1H), 3.06-2.97 (m, 2H), 2.96 (s, 1H), 2.69 (ttd, J=10.6, 6.8, 2.8, 1H), 1.97-1.82 (m, 1H), 1.50 (s, 9H).

Example 30

Preparation of methyl (S)—N-(tert-butoxycarbonyl)-N-(4-(N'-hydroxycarbamimidoyl)-2,3-dihydro-1H-inden-1-yl)glycinate, compound of formula (5') wherein $R^{10}$ is —CO$_2$Me and $R^{16}$ is —C(O)OtBu.

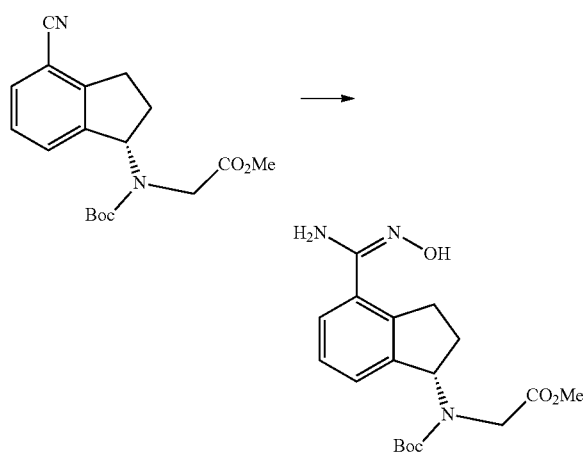

To a solution of methyl (S)—N-(tert-butoxycarbonyl)-N-(4-cyano-2,3-dihydro-1H-inden-1-yl)glycinate (2.4 g, 7.1 mmol) in ethanol (24 mL), triethylamine (2.2 g, 21.4 mmol) and hydroxylamine hydrochloride (1.5 g, 21.4 mmol) were added. At the end of the addition, the mixture was heated to reflux (about 78° C.) and maintained under stirring at the same temperature until complete conversion (about 4 hours). The mixture was cooled to 25° C. and evaporated under reduced pressure. Dichloromethane (20 mL) and a saturated aqueous solution of sodium bicarbonate (15 mL) were added to the residue. The layers were separated and the organic phase was washed with water and brine. The organic layer was evaporated under reduced pressure thus yielding 2.2 g of the title compound as an off-white foam (yield: 86%).

$^1$H NMR (500 MHz, CDCl$_3$, δ ppm, J Hz): δ 7.45-7.39 (m, 1H), 7.37-7.23 (m, 2H), 5.89 (t, J=8.3, 1H), 4.84 (s, 2H), 3.78-3.68 (m, 4H), 3.47 (d, J=17.6, 1H), 3.20 (dtd, J=16.9, 9.1, 2.9, 1H), 2.95 (dt, J=16.9, 8.6, 1H), 2.48 (ddtd, J=21.3, 16.3, 8.2, 2.9, 1H), 1.91 (ddq, J=50.3, 13.2, 8.9, 1H), 1.48 (d, J=9.7, 9H).

Example 31

Preparation of methyl (S)—N-(tert-butoxycarbonyl)-N-(4-(5-(3-cyano-4-isopropoxyphenyl)-1,2,4-oxadiazol-3-yl)-2,3-dihydro-1H-inden-1-yl)glycinate, compound of formula (7''') wherein $R^{10}$ is —CO$_2$Me and $R^{16}$ is —C(O)OtBu.

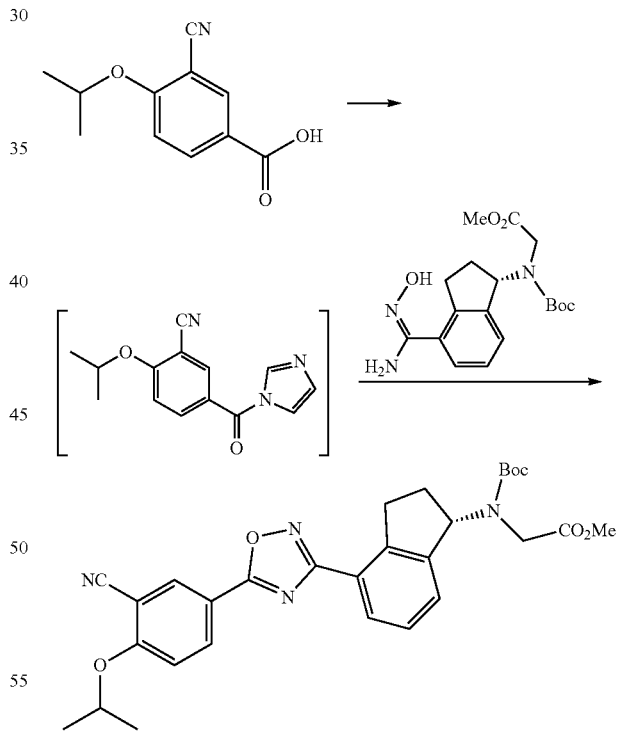

To a solution of 3-cyano-4-isopropoxybenzoic acid (1.3 g, 6.2 mmol) in cyclopentyl methyl ether (13 mL) maintained at 55° C., 1,1'-carbonyldiimidazole (1.6 g, 9.6 mmol) was added portionwise over 20 minutes. The mixture was maintained under stirring at the same temperature until complete conversion (about 1 hour), then a solution of methyl (S)—N-(tert-butoxycarbonyl)-N-(4-(N'-hydroxycarbamimidoyl)-2,3-dihydro-1H-inden-1-yl)glycinate (2.2 g, 6.2 mmol) in cyclopentyl methyl ether (6 mL) was added over 45 minutes.

The reaction mixture was heated to 80° C. and maintained under stirring at the same temperature until complete conversion (about 16 hours). After cooling to 55° C., cyclopentyl methyl ether (19 mL) and water (8 mL) were added and the resulting phases were separated at 50° C. Organic layer was washed with water at the same temperature, concentrated up to obtain a residual volume of 20 mL, then it was heated to 65° C., maintained under stirring at the same temperature for 30 minutes and slowly cooled to 0° C. The resulting solid was filtered, washed with cyclopentyl methyl ether and dried under reduced pressure at 35° C. thus yielding 2.31 g of the title compound as a white solid (yield: 70%).

$^1$H NMR (500 MHz, CDCl$_3$, δ ppm, J Hz): δ 8.45 (d, J=2.1, 1H), 8.36 (dd, J=8.9, 2.2, 1H), 8.14-8.08 (m, 1H), 7.53-7.44 (m, 1H), 7.41 (q, J=7.3, 1H), 7.15 (d, J=8.9, 1H), 4.82 (hept, J=6.1, 1H), 3.75 (d, J=17.7, 1H), 3.71 (d, J=8.4, 3H), 3.51 (d, J=17.8, 1H), 3.46 (ddd, J=12.7, 9.3, 4.2, 1H), 3.18 (ddd, J=17.4, 15.2, 8.0, 1H), 2.59 (ddtd, J=17.0, 13.1, 8.6, 3.3, 1H), 2.05-1.93 (m, 1H), 1.50 (d, J=1.0, 9H), 1.49 (s, 3H), 1.46 (s, 3H).

Example 32

Preparation of methyl (S)—N-(tert-butoxycarbonyl)-N-(4-(5-(3-cyano-4-isopropoxyphenyl)-1,2,4-oxadiazol-3-yl)-2,3-dihydro-1H-inden-1-yl)glycinate, compound of formula (7C''') wherein R$^{16}$ is —C(O)OtBu.

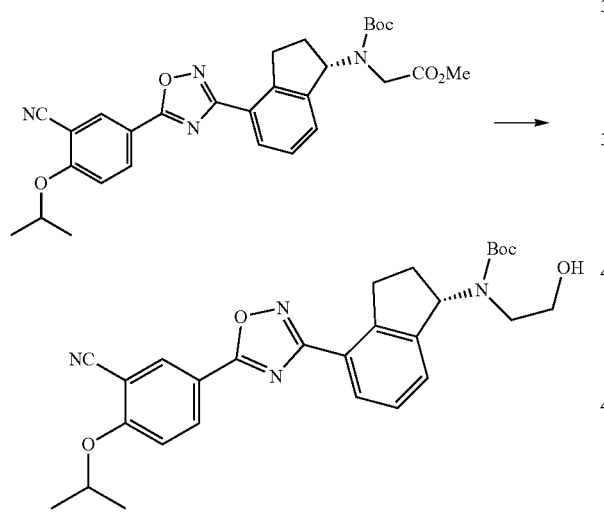

To a solution of methyl (S)—N-(tert-butoxycarbonyl)-N-(4-(5-(3-cyano-4-isopropoxyphenyl)-1,2,4-oxadiazol-3-yl)-2,3-dihydro-1H-inden-1-yl)glycinate (500 mg, 0.9 mmol) in tetrahydrofuran (3 mL) maintained at 25° C., sodium borohydride (92.3 mg, 2.4 mmol) was added. The mixture was heated to reflux (about 65° C.). A solution of methanol (0.6 mL) in tetrahydrofuran (2.3 mL) was slowly added over 4 hours and the reaction mixture was maintained under stirring at the same temperature for about 1 hour. Additional sodium borohydride (35.5 mg, 0.9 mmol) and a solution of methanol (0.2 mL) in tetrahydrofuran (0.4 mL) were added and the mixture was maintained under stirring at 25° C. for about 1 hour. Another portion of sodium borohydride (53.3 mg, 1.4 mmol) and methanol (0.3 mL) were finally added. The mixture was heated to reflux (about 65° C.) and maintained under stirring at the same temperature for about 2 hours. When the reaction was complete, mixture was cooled to 25° C., 1 N hydrochloric acid (2.5 mL) and isopropyl acetate (10 mL) were added, resulting phases were separated and the organic layer was evaporated under reduced pressure thus yielding 410 mg of the title compound as a white foam (yield: 85%).

$^1$H NMR (400 MHz, CDCl$_3$, δ ppm, J Hz): δ 8.28 (s, 1H), 8.20 (d, J=8.0, 1H), 7.98 (d, J=8.0, 1H), 7.43 (d, J=7.6, 1H), 7.24 (t, J=7.6, 1H), 7.01 (d, J=9.2, 1H), 5.18 (d, J=7.2, 1H), 4.80 (t, J=6.4, 1H), 4.75-4.66 (m, 1H), 4.10-4.01 (m, 2H), 3.54-3.32 (m, 3H), 3.10-3.01 (m, 1H), 2.58-2.54 (m, 1H), 1.82-1.75 (m, 1H), 1.41-1.37 (m, 15H).

Example 33

Preparation of ozanimod hydrochloride, the hydrochloride salt of a compound of formula (7'''') wherein R$^{10}$ is —CH$_2$OH.

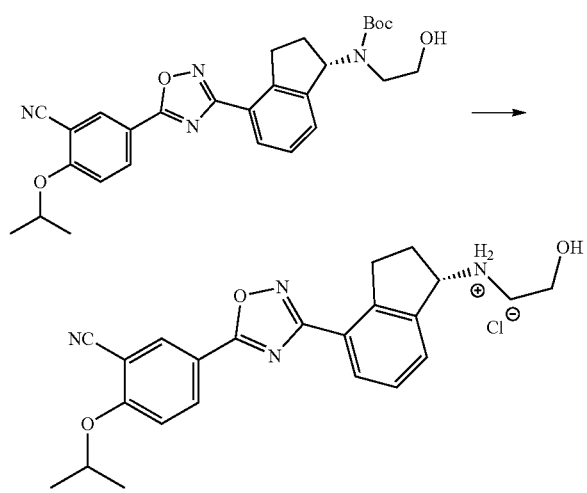

To a solution of tert-butyl (S)-(4-(5-(3-cyano-4-isopropoxyphenyl)-1,2,4-oxadiazol-3-yl)-2,3-dihydro-1H-inden-1-yl)(2-hydroxyethyl)carbamate (160 mg, 0.32 mmol) in dioxane (1.6 mL) maintained at 25° C., 4N solution of hydrogen chloride in dioxane (830 mg, 3.2 mmol) was added. The mixture was heated to 50° C. and maintained under stirring at the same temperature for about 2 hours. The mixture was cooled to 25° C. and diethyl ether (1 mL) was added. At the end of the addition, resulting suspension was maintained under stirring at the same temperature for about 30 minutes. The solid was filtered, washed with diethyl ether (1 mL) and dried at 40° C. under reduced pressure thus yielding 85 mg of the title compound (yield: 66%) with spectral data in accordance with those reported in paragraph [0372] of WO 2011/060392.

Example 34

Preparation of (S)-1-amino-2,3-dihydro-1H-indene-4-carbonitrile, compound of formula (12) wherein R$^1$ is —CN.

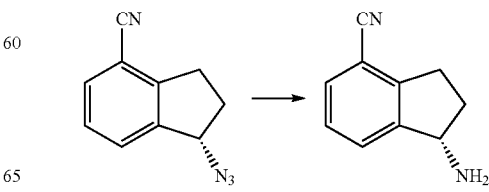

To a solution of (S)-1-azido-2,3-dihydro-1H-indene-4-carbonitrile (3.1 g, 16.8 mmol, enantiomeric ratio S:R=99.5:0.5) in a mixture of tetrahydrofuran (30 mL) and water (10 mL), triphenyl phosphine (13.3 g, 50.6 mmol) was added. The mixture was maintained under stirring until complete gas evolution (about 12 hours) then evaporated under reduced pressure so as to remove tetrahydrofuran. Ethyl acetate (50 mL) was added thereto and the resulting mixture maintained under stirring for 30 minutes. The solid was filtered and the filtrate extracted with 4N hydrochloride acid. 4N aqueous solution of sodium hydroxide was added to the separated aqeuous phase so as to achieve a pH above 12, then it was extracted with dichloromethane. The phases were separated and the organic layer was evaporated under reduced pressure so as to provide 1.9 g of the title compound (yield: 73%) with spectral data in accordance with those reported in example 27.

Example 35

Preparation of (S)-1-azido-N'-hydroxy-2,3-dihydro-1H-indene-4-carboximidamide, Compound of Formula (5A1)

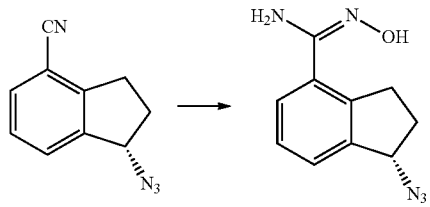

To a solution of (S)-1-amino-2,3-dihydro-1H-indene-4-carbonitrile (250 mg, 1.4 mmol, enantiomeric ratio S:R=99.5:0.5) in ethanol (10 mL), hydroxylamine hydrochloride (118 mg, 1.7 mmol) and sodium carbonate (180 mg, 1.7 mmol) were added. The mixture was maintained under stirring under reflux conditions for about 12 hours then cooled to 25° C. and filtered. The filtrate was evaporated under reduced pressure and the crude purified by silica gel flash chromatography (petroleum ether:ethyl acetate 4:6 (V/V)) to provide 201 mg of the title compound (yield: 79%).

$^1$H NMR (400 MHz, CDCl$_3$, δ ppm, J Hz): δ 7.46-7.41 (m, 2H), 7.27 (t, J=7.2, 1H), 4.85 (bs, 2H), 3.26-3.18 (m, 1H), 3.07-3.00 (m, 1H), 2.45-2.37 (m, 1H), 2.11-2.04 (m, 1H).

Example 36

Preparation of (S)-5-(3-(1-azido-2,3-dihydro-1H-inden-4-yl)-1,2,4-oxadiazol-5-yl)-2-isopropoxybenzonitrile, Compound of Formula (13B)

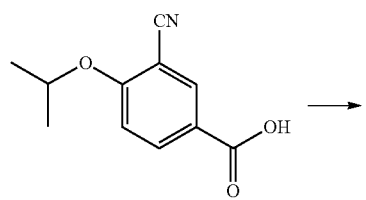

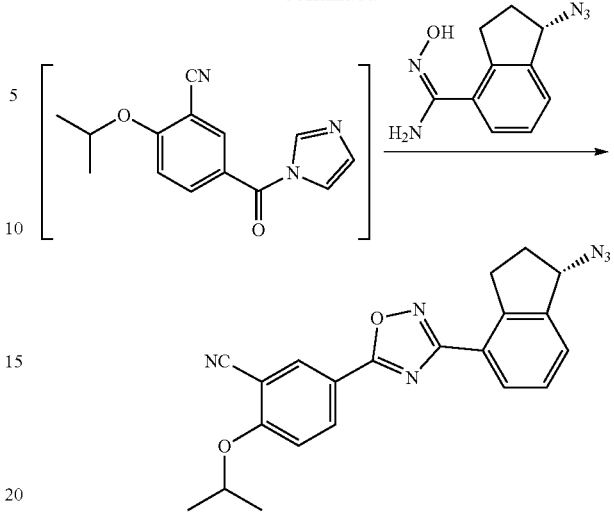

To a solution of 3-cyano-4-isopropoxybenzoic acid (132 mg, 0.64 mmol) in dimethylformamide (3 mL) maintained at 0° C., 1,1'-carbonyldiimidazole (115 mg, 0.71 mmol) was added portionwise. The mixture was maintained under stirring at the same temperature for about 30 minutes, then a solution of (S,E)-1-azido-N'-hydroxy-2,3-dihydro-1H-indene-4-carboximidamide (140 mg, 0.64 mmol) in dimethylformamide (2 mL) was added. The mixture was maintained under stirring at 25° C. for 3 hours, then 1,1'-carbonyldiimidazole (115 mg, 0.71 mmol) was added. The mass was heated to 115° C. and maintained under stirring at the same temperature until complete conversion (about 24 hours). After cooling to 25° C., ethyl acetate (20 mL) was added. The mixture was washed with an aqueous saturated solution of NaHCO$_3$, 1 N hydrochloric acid, water and brine. The organic layer was evaporated under reduced pressure and the crude purified by silica gel chromatography (petroleum ether:ethyl acetate 7:3 (V/V)) thus yielding 170 mg of the title compound as a colorless oil (yield: 69%).

$^1$H NMR (400 MHz, CDCl$_3$, δ ppm, J Hz): δ 8.30 (d, J=1.6, 1H), 8.24 (dd, J=8.8, 2.0, 1H), 8.07 (d, J=7.6, 1H), 7.48 (d, J=7.2, 1H), 7.36 (t, J=7.6, 1H), 7.06 (d, J=8.8, 1H), 4.89 (t, J=4.8, 1H), 4.77-4.71 (m, 1H), 3.31 (dddd, J=72.4, 14.4, 8.0, 5.6, 2H), 2.53-2.44 (m, 1H), 2.20-2.11 (m, 1H), 1.43 (d, J=6.0, 6H).

CITED REFERENCES

WO 2009/151529 A1;
EP 2291080 B1;
WO 2011/060392 A1;
WO 2018/028557 A1;
Theodora W. Green, *Protective Groups in Organic Synthesis*, John Wiley & Sons (1999) pp. 23-113, pp. 113-148, pp. 149-179 or pp. 179-187 or pp. 503-598;
S. D. Burke (Ed.), *Handbook of Reagents for Organic Synthesis, Oxidizing and Reducing Agents*, Wiley (1999, reprinted July 2005) pp. 1 and 6.
*Organic Process Research and Development* 2013, vol. 13, pages 1239-1246
WO 2011/060389 A1.
The following pages of the description refer to some of the embodiments of the invention listed as separate items:
1. Process for the preparation of a compound of general formula (7) or a salt thereof, said process comprising:

a) reacting an indanone of general formula (1) with a compound of general formula (2) so as to provide a compound of general formula (3);

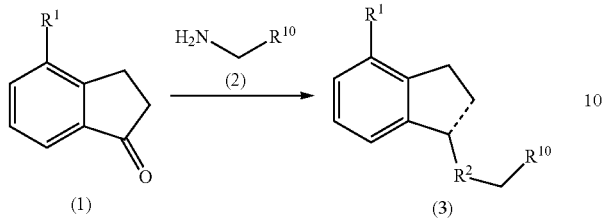

b) converting said compound of general formula (3) into a compound of general formula (7) or a salt thereof;

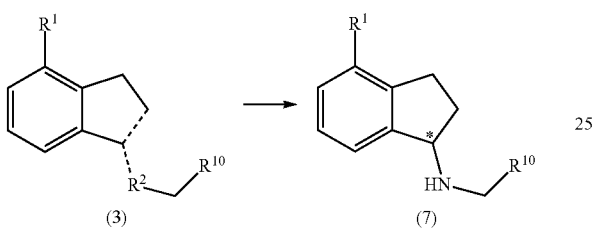

wherein:
R¹ is selected from the group consisting of —CN and 1,2,4-oxadiazole, said 1,2,4-oxadiazole being attached to the bicycle via carbon 3 and optionally substituted in position 5 with a 3'-cyano-4'-isopropoxyphenyl group;
one of the dashed lines indicates a single bond and the other one a double bond,
when the dashed line linked to R² is a double bond, R² is N, and when the dashed line linked to R² is a single bond, R² is NH;
R¹⁰ is selected from the group consisting of —CH₂OH, —CH₂OPg and —CO₂R¹²;
R¹² is selected from the group consisting of H, a linear or branched (C1-C8)alkyl- or a linear or branched (C1-C8)alkyl substituted with a (C6-C10)aryl;
Pg is an oxygen protecting group; and
the * indicates a stereogenic center;
said process being characterized in that step a) is carried out in the absence of titanium alkoxides.

2. The process of item 1, in which step a) is carried out in the absence of titanium-based Lewis acids.

3. The process of any one of items 1 or 2, in which a compound of general formula (2A) is used in step a):

wherein:
R¹³ is selected from the group consisting of H and Pg; and
Pg is as defined in item 1.

4. The process of item 3, in which the reaction between the indanone of general formula (1) and the compound of general formula (2A) leads to a compound of formula (3A):

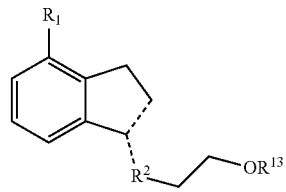

wherein R¹, R², and the dashed lines are as defined in claim 1, and R¹³ is as defined in item 2.

5. The process of item 4, in which the reaction between the indanone of general formula (1) and the compound of general formula (2A) is carried out in a solvent or a mixture of solvents in which the indanone of general formula (1) is soluble and the compound of general formula (3A) is insoluble 6. The process of any one of items 1 to 5, in which steps a) and b) are carried out without isolating the compound of general formula (3).

7. The process of any one of items 1 to 6, in which an indanone of formula (1') or (1") is used as a reactant in step a):

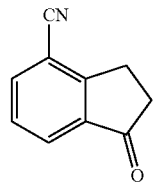

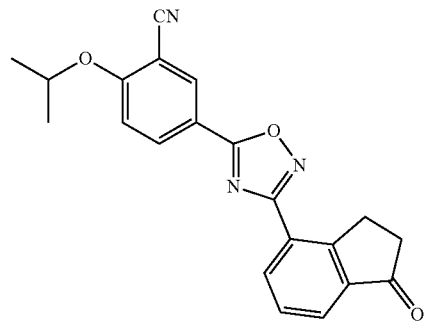

8. The process of item 7, in which the indanone of formula (1") is prepared according to the following steps:
c) providing a protected indanone of formula (4):

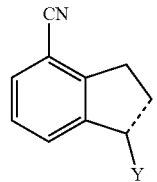

d) treating said protected indanone of formula (4) with hydroxylamine or a salt thereof so as to provide an amidoxime of formula (5), a tautomer or a salt thereof:

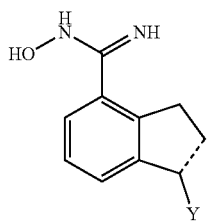

(5)

e) converting said amidoxime of formula (5), the tautomer or the salt thereof, into a protected indanone of formula (6):

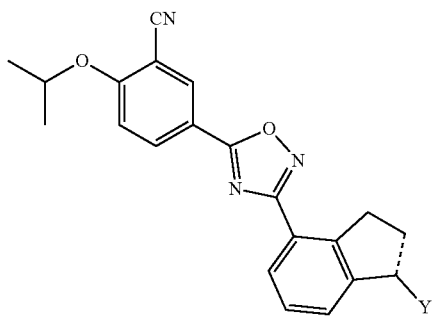

(6)

f) converting said protected indanone of formula (6) into an indanone of formula (1'''):

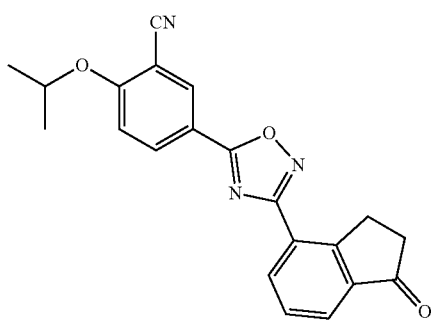

(1''')

in which:
Y, together with the carbon atom to which it is bonded, forms a cyclic ketal, a ketal or an enol ether; and
the dashed line indicates a single or a double bond; with the proviso that when the dashed line indicates a double bond, Y, together with the carbon atom to which it is linked, forms an enol ether.

9. The process of item 8, in which the protected indanone of formula (4) is a cyclic ketal of formula (4A), a ketal of formula (4B) or an enol ether of formula (4C):

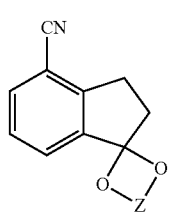

(4A)

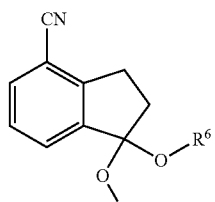

(4B)

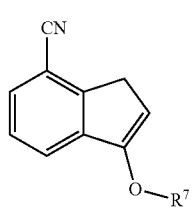

(4C)

in which:
Z is $(CR^3R^4)_n$;
n is 2 or 3;
$R^3$ and $R^4$ are, independently of each other, hydrogen or a linear or branched (C1-C6)alkyl;
$R^5$ and $R^6$ are, independently of each other, a linear or branched (C1-C8)alkyl;
$R^7$ is selected from the group consisting of a linear or branched (C1-C8)alkyl, a linear or branched (C1-C8)alkyl substituted with a (C6-C10)aryl, $R^8C(O)$— and $(R^9)_3Si$—; and
$R^8$ and $R^9$ are, independently of each other, a linear or branched (C1-C8)alkyl or a linear or branched (C1-C8)alkyl substituted with a (C6-C10)aryl.

10. The process of any one of items 8 or 9, in which step e) is carried out by treating the amidoxime of formula (5), the tautomer or the salt thereof, with a compound of formula (8):

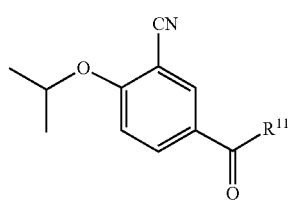

(8)

in which $R^{11}$ is selected from the group consisting of a linear or branched (C1-C6)alkoxy-, OH, imidazole, and a halogen.

11. The process of item 10, in which an additional step e') is carried after step e), said step e') comprising heating the mass resulting from the reaction between the compound of formula (8) and the amidoxime of formula (5), the tautomer or the salt thereof, to a temperature from 50° C. to 120° C.

12. The process of item 7, in which the indanone of formula (1") is prepared according through oxidation of the alcohol of formula (1'''):

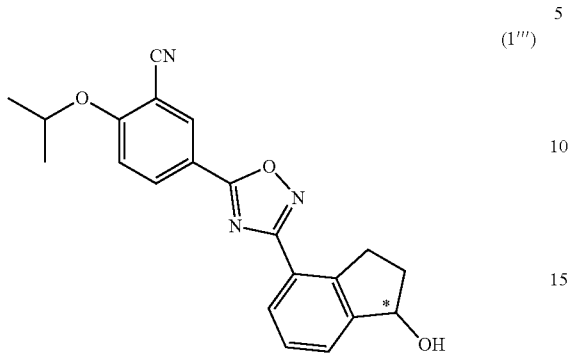

(1''')

13. The process of item 12, in which the oxidation of the alcohol of formula (1''') is carried out using:
    the Swern oxidation conditions;
    the Corey-Kim oxidation conditions;
    the Pfitzner-Moffat oxidation conditions;
    the Anelli oxidation conditions;
    the Ley oxidation conditions;
    the Parikh-Doering oxidation conditions;
    bis(acetoxy)iodobenzene and 2,6,6-tetramethylpiperidin-1-oxyl (TEMPO);
    hypervalent iodine based oxidizing agents; and
    trichloroisocyanuric acid optionally in the presence of TEMPO.
14. The process of any one of items 1 to 13, in which step b) is carried out under non-stereoselective reaction conditions.
15. The process of item 14, in which, in step b), the compound of general formula (3) is converted into a compound of general formula (7) or a salt thereof by treatment with a reducing agent.
16. The process of any one of items 1 to 13, in which step b) is carried out under stereoselective reaction conditions.
17. The process of any one of items 1 to 13 and 16, in which step b) is carried out in the presence of an asymmetric hydrogenation catalyst of formula (9) or of formula (10):

$$M_m L_n X'_p Y'_q \quad (9)$$

$$[M_m L_n X'_p Y'_q] Z'_s \quad (10)$$

wherein:
    M is a transition metal of group VIII of the periodic table of elements;
    L is a chiral ligand;
    X' is selected from the group consisting of a halogen atom, a carboxylato group, an allyl group, a 1,5-cyclooctadiene or a norbornadiene;
    Y' is a ligand;
    Z' is an anion; and
    m, n', p, q and s are, independently of each other, an integer from 0 to 5.

18. The process of item 17, in which the chiral ligand L is a diamine of formula (14):

(14)

wherein:
    $R^i$, $R^j$, $R^k$ or $R^l$ are independently hydrogen, a saturated or unsaturated alkyl, a cycloalkyl group, an aryl group, a urethane, or a sulphonyl group;
    $R^e$, $R^f$, $R^g$ or $R^h$ are independently hydrogen, a saturated or unsaturated alkyl group, a saturated or unsaturated cycloalkyl group, or an aryl group; alternatively, $R^e$ together with $-CR^f-A_t-CR^g$, $R^e$ together with $-CR^f-A_t-CR^h$, $R^f$ together with $-CR^e-A_t-CR^g$ or $R^f$ together with $-CR^e-A_t-CR^h$ may form a 4- to 8-membered cycloalkyl ring or a 4- to 8-membered cycloalkyl ring substituted by 1, 2 or 3 substituents independently selected from (C1-C6)alkyl,
    A is a linking group comprising one or two substituted or unsubstituted carbon atoms; and
    t is 0 or 1;
    with the proviso that $R^e$ to $R^h$ or $R^i$ to $R^l$ or linking group A are chosen such that the ligand is chiral.
19. The process of any one of items 17 or 18, in which the chiral ligand L is selected from the group consisting of cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted-phospholano)benzene (DuPHOS), 1,2-bis(substituted-phospholano)ethane (BPE), 1-((substituted-phospholano)-2-(diphenylphosphino)benzene (UCAP-Ph), 1-(bis(3,5-dimethylphenyl)phosphino)-2-(substituted-phospholano)benzene (UCAP-DM), 1-((substituted-phospholano)-2-(bis(3,5-di(t-butyl)-4-methoxyphenyl)phosphino)benzene (UCAP-DTBM), 1-((substituted-phospholano)-2-(di-naphthalen-1-ylphosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl) ($H_8$—BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis(diphenylphosphino)-6,6'-dimethyl-1,1'-biphenyl (BICHEP), ((5,6),(5',6')-bis(methylenedioxy)biphenyl-2,2'-diyl)(bisdiphenylphosphine) (SEGPHOS), ((5,6),(5',6')-bis(methylenedioxy)biphenyl-2,2'-diyl)(bis(3,5- dimethylphenyl)phosphine) (DM-SEGPHOS), ((5,6),(5',6')-bis(methylenedioxy)biphenyl-2,2'-diyl)(bis(3,5-di(tert-butyl)-4-methoxyphenyl)phosphine) (DTBM-SEGPHOS), H-[P-H8-BINOL]-BoPhoz, N-p-tosyl-1,2-diphenylethylenediamine (Ts-DPEN), N-methanesulfonyl-1,2-diphenylethylenediamine (Ms-DPEN), N-[1,2-diphenyl-2-[(3-phenylpropyl)amino]ethyl]-4-methyl-benzenesulfonamide (C3-teth-Ts-DPEN), N-[1,2-diphenyl-2-[(4-phenylbutyl)amino]ethyl]-4-methyl-benzenesulfonamide (C4-teth-Ts-DPEN), N-[1,2-diphenyl-2-[(3-phenylpropyl)amino]ethyl]-methanesulfonamide (C3-teth-Ms-DPEN), N-[1,2-diphenyl-2-[(4-phenylbutyl)amino]ethyl]-methanesulfonamide (C4-teth-Ms-DPEN), N-[1,2-diphenyl-2-[(3-phenylpropyl)amino]ethyl]-2,4,6-trimethyl-benzenesulfonamide (C3-teth-Mts-DPEN), N-[1,2-diphenyl-2-[(4-phenylbutyl)amino]ethyl]-2,4,6-trimethyl-benzenesulfonamide (C4-teth-Mts-DPEN), N-[1,2-diphenyl-2-[(3-phenylpropyl)amino]ethyl]-2,4,6-triisopropyl-benzenesulfonamide (C3-teth-Tris-DPEN), N-[1,2-diphenyl-2-[(4-phenylbutyl)amino]ethyl]-2,4,6-triisopropyl-benzenesulfonamide (C4-teth-Tris-DPEN), N-p-tosyl-1,2-cyclohexanediamine (Ts-DACH), 2,2',6,6'-tetramethoxy-4,4'-bis(diphenylphosphino)-3,3'-bipyridine (P-Phos), 4,12-bis(diphenylphosphino)-[2.2]-paracyclophane (Phanephos), and 1-(diphenylphosphino)-2-[1-[(diphenylphosphino)methylamino]ethyl]ferrocene (MeBoPhoz).

20. The process of any one of items 1 to 19, in which step b) is carried out in the presence of a compound of general formula (2), (2A) or (2B):

(2B)

wherein:
$R^{14}$ is $-CO_2R^{12}$; and
$R^{12}$ is as defined in item 1.

21. The process of any one of items 1 to 20, further comprising converting the compound of general formula (7) into Ozanimod or a salt thereof.

22. Process for the preparation of an enantiomerically pure amine of formula (12) or a salt thereof, said process comprising:
   h) providing an azide of formula (13):

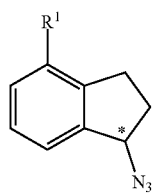
(13)

i) converting said azide of formula (13) into an amine of formula (12):

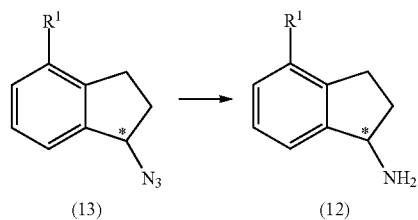
(13)    (12)

j) optionally converting said amine of formula (12) into an enantiomerically pure amine of formula (12) or an enantiomerically pure salt thereof by treatment with a chiral or an achiral Brønsted acid;

wherein:
$R^1$ is selected from the group consisting of —CN and 1,2,4-oxadiazole, said 1,2,4-oxadiazole being attached to the bicycle via carbon 3 and optionally substituted in position 5 with a 3'-cyano-4'-isopropoxyphenyl group; and
the * indicates a stereogenic center;
said process being characterized in that the reduction of step i) is performed according to Staudinger reaction conditions.

23. The process of item 22, in which an enantiomerically pure amine of formula (12A) or (12B) or a salt of any one of them is prepared in step i) or j).

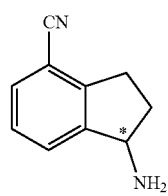
(12A)

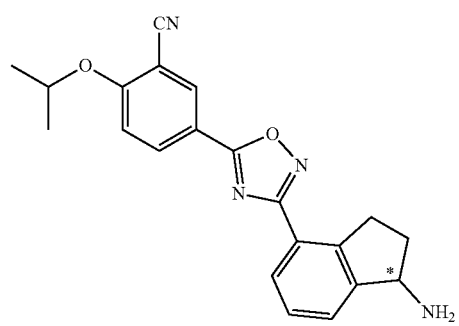
(12B)

24. The process of any one of items 22 or 23, in which an azide of formula (13A) or (13B) is provided in step h):

(13A)

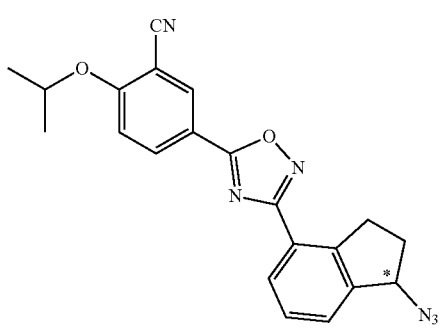

(13B)

25. The process of item 24, in which the azide of formula (13B) is prepared according to the following steps:
    h.1) treating an azide of formula (13A) with hydroxylamine or a salt thereof so as to provide an amidoxime of formula (5A1), a tautomer or a salt thereof:

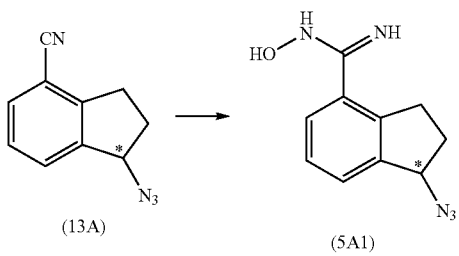 [SMILES: N#Cc1cccc2c1CCC2N=[N+]=[N-] ; [N-]=[N+]=NC1CCc2c(C(=N)NO)cccc21]

h.2) converting said amidoxime of formula (5A1), the tautomer or the salt thereof, into the azide of formula (13B):

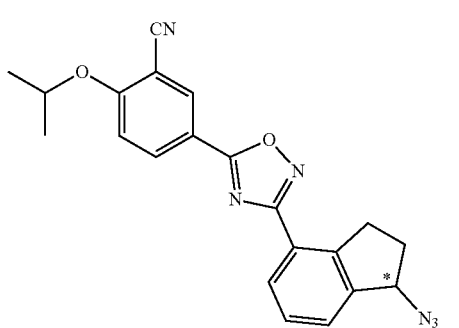

26. The process of item 25, in which step h.2) is carried out by treating the enantiomerically pure amidoxime of formula (5A1), the tautomer or the salt thereof with a compound of formula (8):

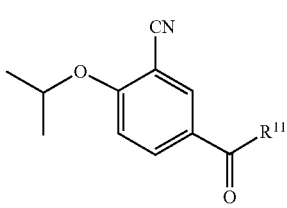

(8)

in which $R^{11}$ is selected from the group consisting of a linear or branched (C1-C6)alkoxy-, OH, imidazole, and a halogen.

27. The process of item 26, further comprising a step h.2'), carried out after step h.2), comprising heating the mass resulting from the reaction between the compound of formula (8) and the enantiomerically pure amidoxime of formula (5A1), the tautomer or the salt thereof, to a temperature from 50° C. to 120° C.

28. The process of any one of items 22 to 27, in which step j) is carried out according to synthetic scheme j.1), said synthetic scheme comprising the treatment of an enantiomerically pure amine of formula (12) with a chiral or achiral Brønsted acid so as to obtain an enantiomerically pure salt thereof.

29. The process of any one of items 22 to 27, in which step j) is carried out according to synthetic scheme j.2), said synthetic scheme comprising the treatment of an enantiomerically enriched amine of formula (12) with a chiral Brønsted acid so as to obtain an enantiomerically pure salt thereof.

30. The process of any one of items 22 to 27, in which step j) is carried out according to synthetic scheme j.3), said synthetic scheme comprising the treatment of a racemic amine of formula (12) with a chiral Brønsted acid so as to obtain an enantiomerically pure salt thereof.

31. The process of any one of items 22 to 30, in which the chiral Brønsted acid is selected from the group consisting of (1R)-(−)-10-camphorsulfonic acid, (1 S)-(+)-10-camphorsulfonic acid, N-formyl-L-leucine, L-(−)-malic acid, D-(+)-malic acid, (R)-(−)-mandelic acid, (S)-(+)-mandelic acid, (−)-2,3-dibenzoyl-L-tartaric acid, (+)-2,3-dibenzoyl-D-tartaric acid, D-(−)-tartaric acid and L-(+)-tartaric acid.

32. The process of any one of items 22 to 31, further comprising a step k), carried out after step i) or j), comprising converting the enantiomerically pure amine of general formula (12) or the salt thereof into an enantiomerically pure compound of general formula (7) or a salt thereof.

33. The process of item 32, in which step k) is carried out according to synthetic scheme k.1), said scheme comprising the treatment of the enantiomerically pure amine of general formula (12) or the salt thereof with a compound of formula (15) so as to provide an enantiomerically pure compound of general formula (7) or a salt thereof:

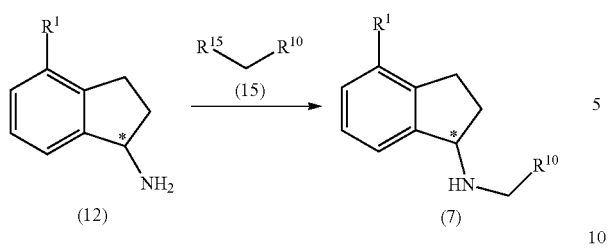

wherein:
R¹ is as defined in claim 21;
R¹⁰ is selected from the group consisting of —CH₂OH, —CH₂OPg and —CO₂R¹²;
R¹² is selected from the group consisting of H, a linear or branched (C1-C8)alkyl or a linear or branched (C1-C8)alkyl substituted with a (C6-C10)aryl;
Pg is an oxygen protecting group; and
R¹⁵ is a leaving group able to undergo a nucleophilic substitution.

34. The process of any one of items 32 or 33, in which the enantiomerically pure amine of general formula (12) used in step k) is an enantiomerically pure amine of general formula (12A) or (12B)

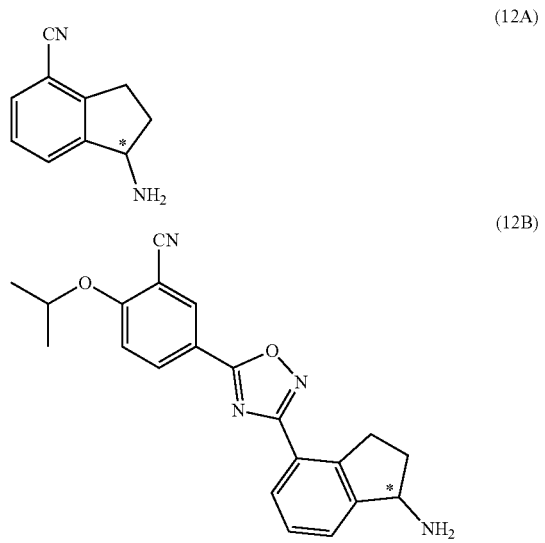

35. The process of item 34, in which step k) is carried out according to synthetic scheme k.2), said scheme k.2) comprising the following steps:
k.2.1) treating an enantiomerically pure amine of formula (12A) or a salt thereof with a compound of formula (15) so as to form an enantiomerically pure compound of formula (7') or a salt thereof:

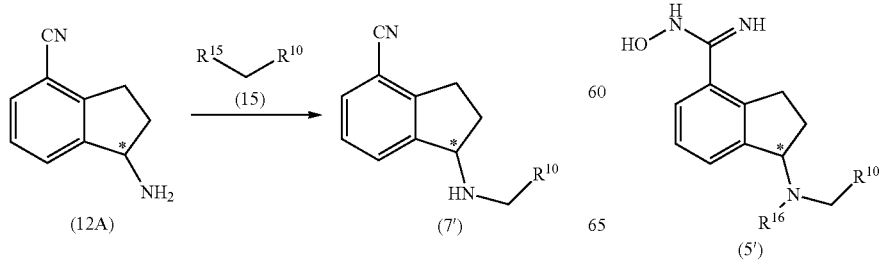

k.2.2) converting the enantiomerically pure compound of formula (7') or the salt thereof into an enantiomerically pure compound of formula (7"):

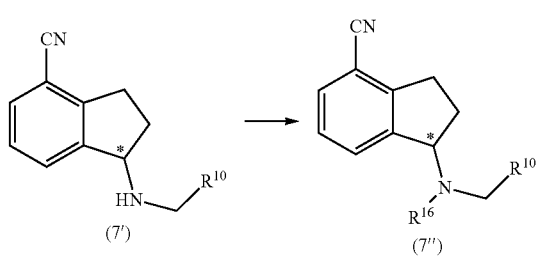

k.2.3) treating said enantiomerically pure compound of formula (7") with hydroxylamine or a salt thereof so as to provide an enantiomerically pure amidoxime of formula (5'), a tautomer or a salt thereof:

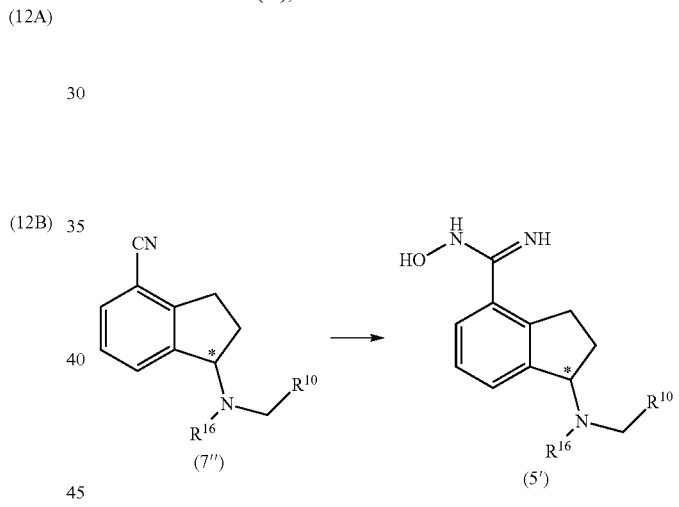

k.2.4) converting said enantiomerically pure amidoxime of formula (5'), the tautomer or the salt thereof, into an enantiomerically pure protected compound of formula (7'''):

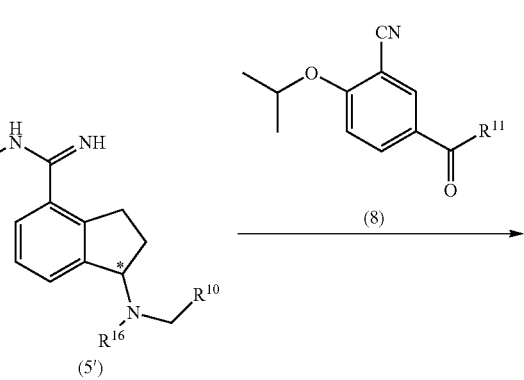

-continued

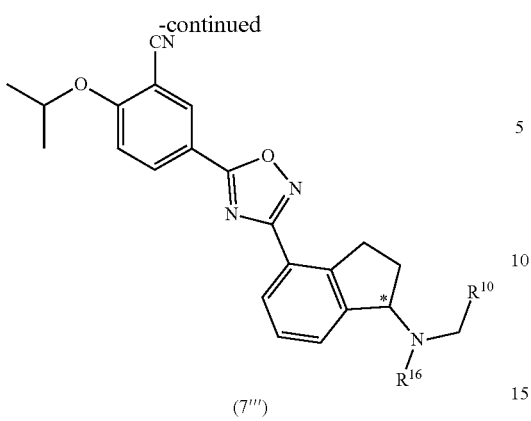
(7''')

k.2.5) converting said enantiomerically pure protected compound of formula (7''') into an enantiomerically pure amine of formula (7'''') or a salt thereof:

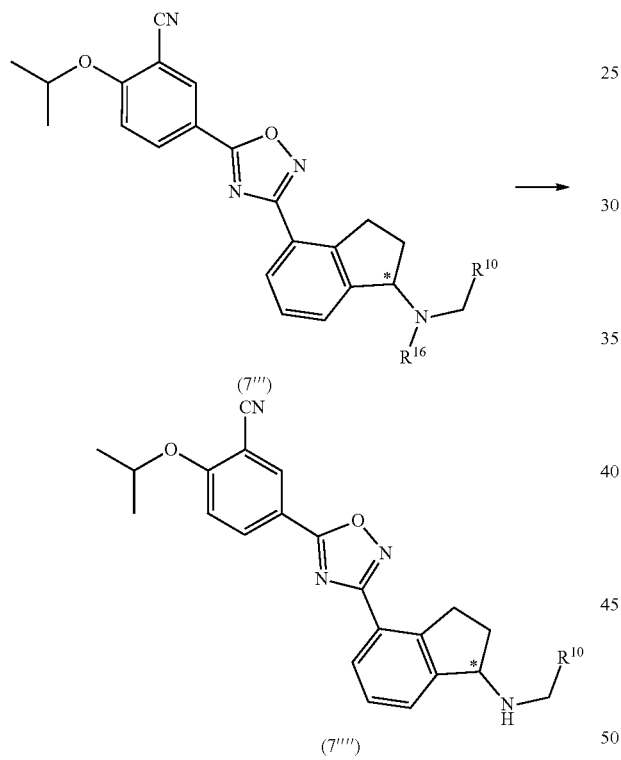

and
wherein:
R[10] is selected from the group consisting of —CH$_2$OH, —CH$_2$OPg and —CO$_2$R[12];
R[11] is selected from the group consisting of a linear or branched (C1-C6)alkoxy-, OH, imidazole and a halogen
R[12] is selected from the group consisting of H, a linear or branched (C1-C8)alkyl or a linear or branched (C1-C8)alkyl- substituted with a (C6-C10)aryl;
Pg is an oxygen protecting group; and
R[15] is a leaving group able to undergo a nucleophilic substitution; and
R[16] is a nitrogen protecting group.

36. The process of any one of items 33 to 35, in which the compound of formula (15) used in step k.1) or k.2.1) is a compound of formula (15A) or (15B):

(15A)

(15B)

wherein:
R[12] and R[15] are as defined in item 33;
R[13] is selected from the group consisting of H and Pg; and
Pg is an oxygen protecting group; and
R[14] is —CO$_2$R[12].

37. The process of any one of items 33 to 36, in which a cyclic or acyclic tertiary amine is used in step k.1), k.2.1) or k.2.2).

38. The process of any one of items 36 to 37, in which a compound of formula (5A') or (5B') is provided in in step k.2.3).

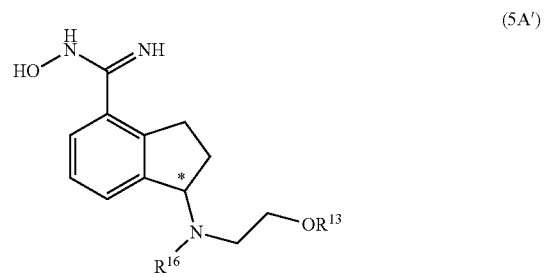
(5A')

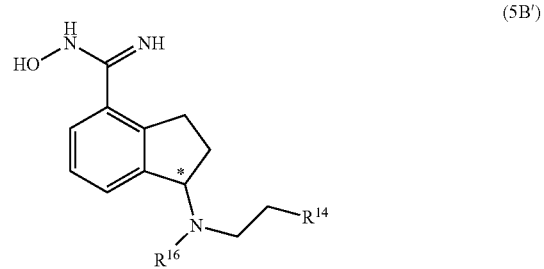
(5B')

wherein R[13] is as defined in item 36; and
R[16] is a nitrogen protecting group.

39. The process of any one of items 36 to 38, in which a compound of formula (7A''') or (7B''') is provided in in step k.2.4).

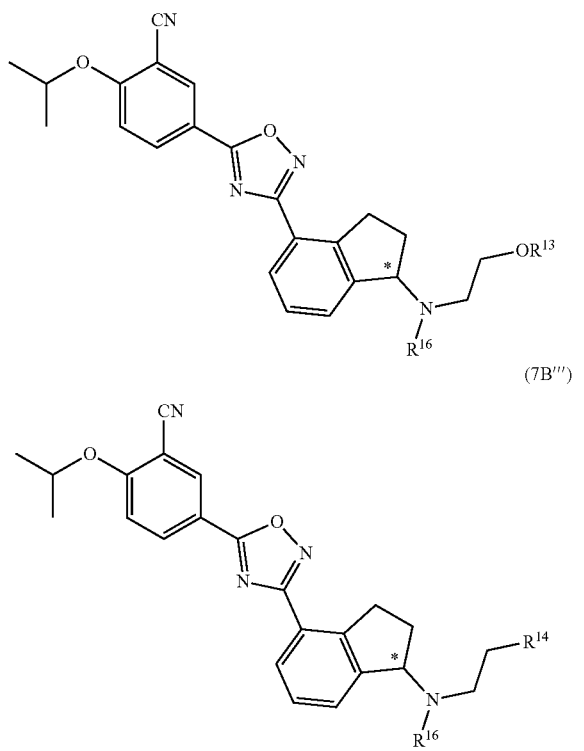

(7A''')

(7B''')

wherein R¹³ is as defined in item 36; and
R¹⁶ is a nitrogen protecting group.

40. The process of any one of items 35 to 39, further comprising a step k.2.4'), carried out after step k.2.4), said step k.2.4') comprising heating the mass resulting from the reaction between the compound of formula (8) and the enantiomerically pure amidoxime of formula (5'), the tautomer or the salt thereof, to a temperature from 50° C. to 120° C.

41. The process of any one of items 35 to 40, further comprising step k.2.4"), carried out after either step k.2.4) or k.2.4'), said step k.2.4") comprising converting the enantiomerically pure protected (7''') into an enantiomerically pure protected compound of formula (7C'''):

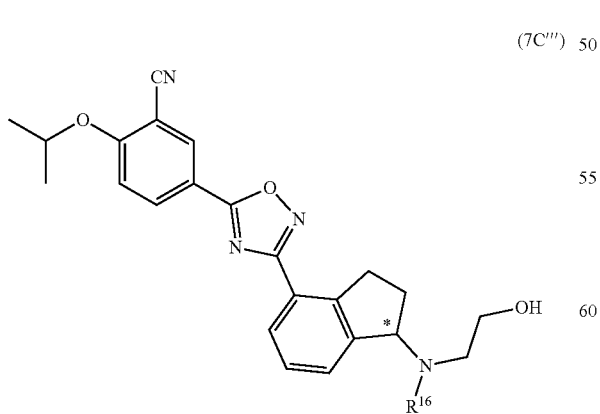

(7C''')

42. The process of any one of items 35 to 41, further comprising converting the enantiomerically pure protected (7''') or the enantiomerically pure protected compound of formula (7C''') into Ozanimod or a salt thereof.

43. The process of any one of items 22 to 42, in which step i) is carried out in the presence of an optionally supported trivalent phosphorous compound.

44. The process of any one of items 22 to 43, in which step i) is carried out in the presence of an optionally supported trialkyl- or triarylphosphine.

45. The process of any one of items 22 to 44, in which step i) is carried out in the presence of an optionally supported triphenylphosphine.

46. The process of any one of items 22 to 45, in which step i) is carried out in the presence of at least one aromatic hydrocarbon, at least one polar aprotic solvent or a mixture thereof.

47. The process of any one of items 22 to 46, in which step i) is carried out in the presence of a solvent mixture comprising at least one aromatic hydrocarbon and at least one ether.

48. Crystalline hemitartrate salt of an amine of formula (12A);

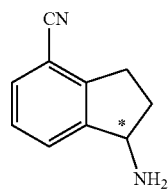

(12A)

said hemitartrate salt being characterized in that it shows an X-ray powder diffraction pattern that, when collected with the Kα radiation of copper (λ=1.5406 Å), comprises peaks at:
I. 6.84°, 19.20°, 22.68° and 25.68°±0.2° 2θ; or
II. 6.84°, 16.16°, 19.20°, 22.68° and 25.68°±0.2° 2θ; and
wherein the * indicates a stereogenic center.

49. Compound of formula:

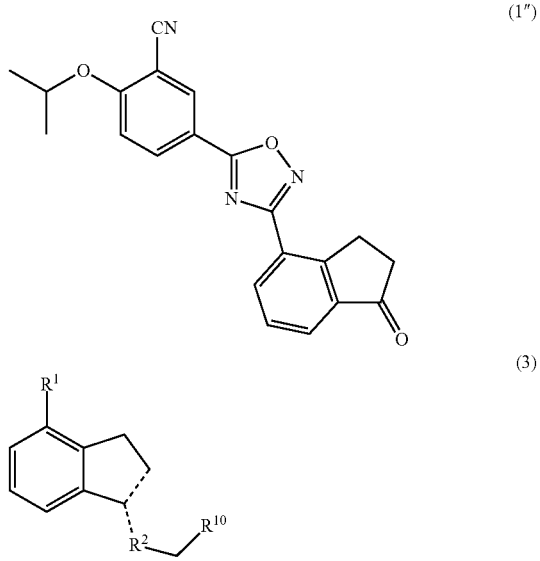

(1'')

(3)

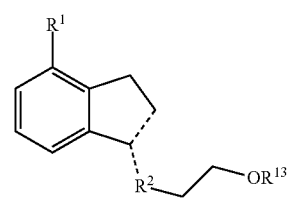
(3A)
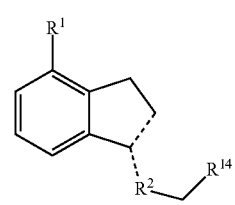
(3B)
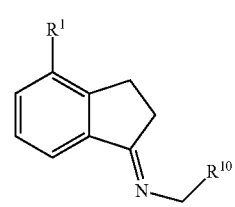
(3A1)
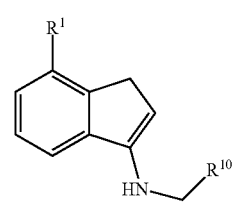
(3A2)
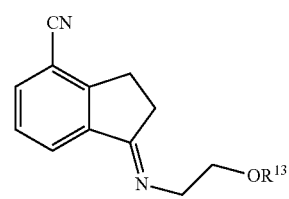
(3A′)
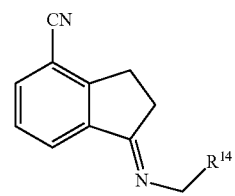
(3B′)
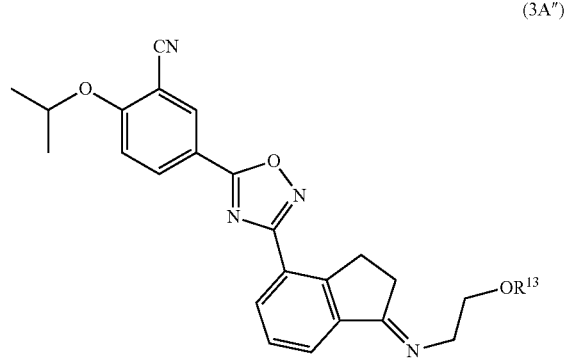
(3A″)
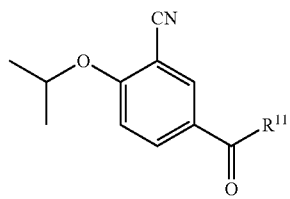
(8)
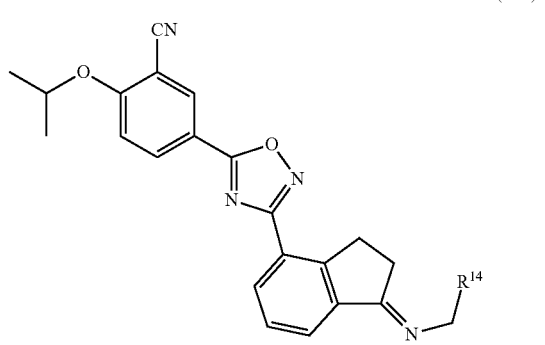
(3B″)
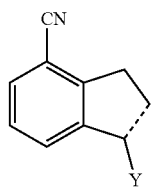
(4)
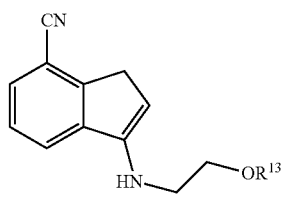
(3A‴)
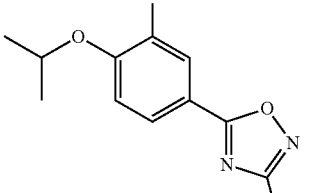
(3A″″)
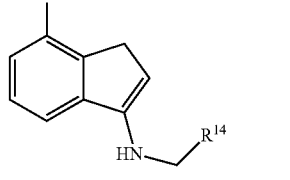
(3B‴)

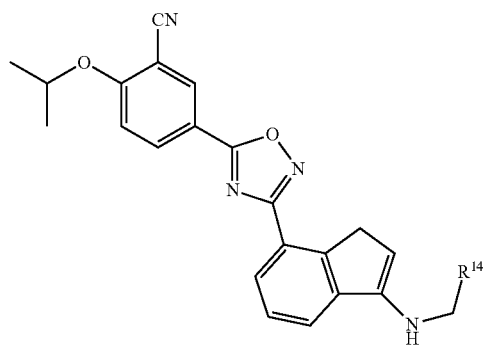 (3B'''')
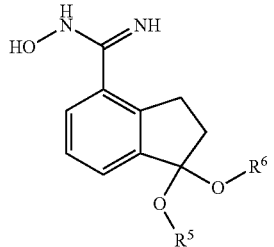 (5B)
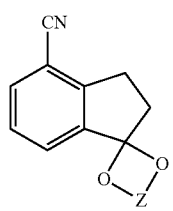 (4A)
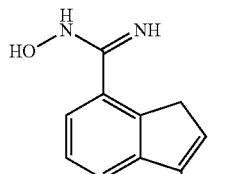 (5C)
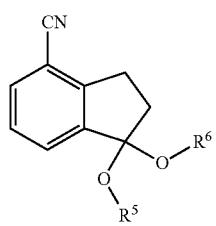 (4B)
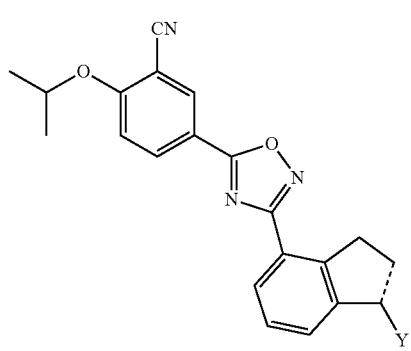 (6)
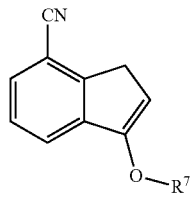 (4C)
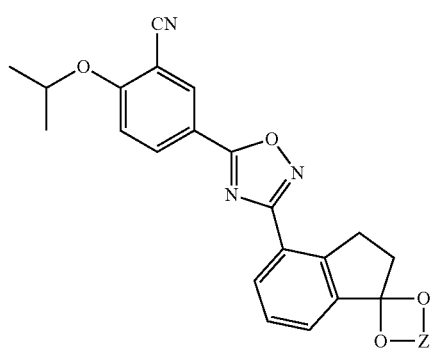 (6A)
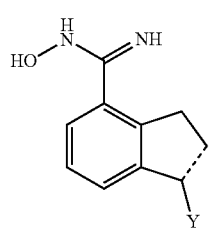 (5)
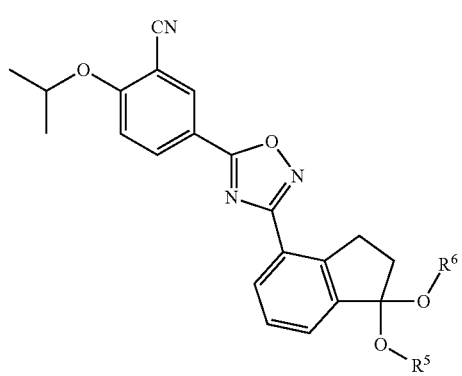 (6B)
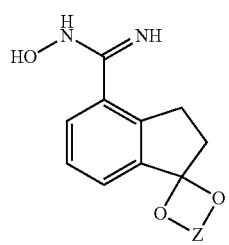 (5A)

-continued
(6C)
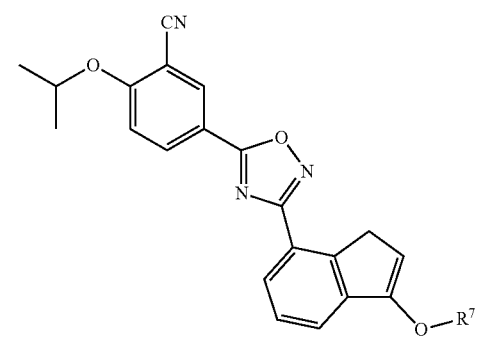
(7A′)
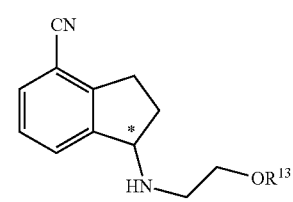
(7B′)
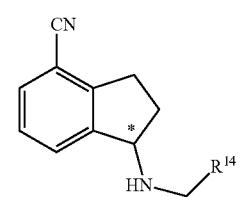
(7A″)
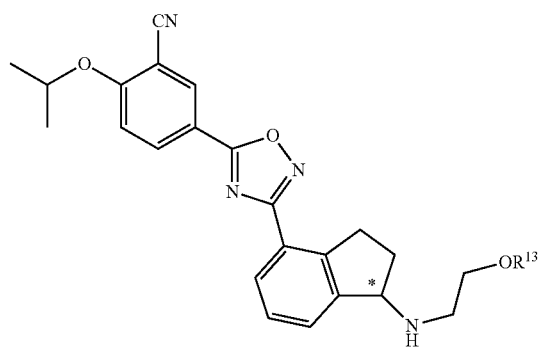
(7B″)
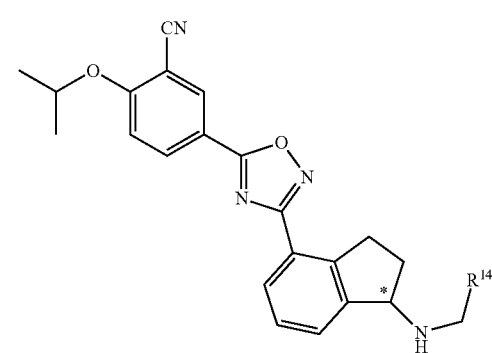
-continued
(6′)
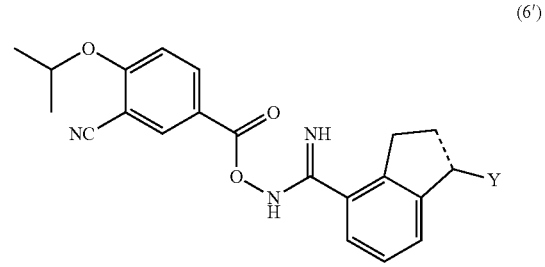
(3A‴)
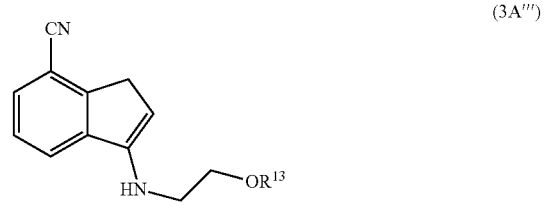
(3A″″)
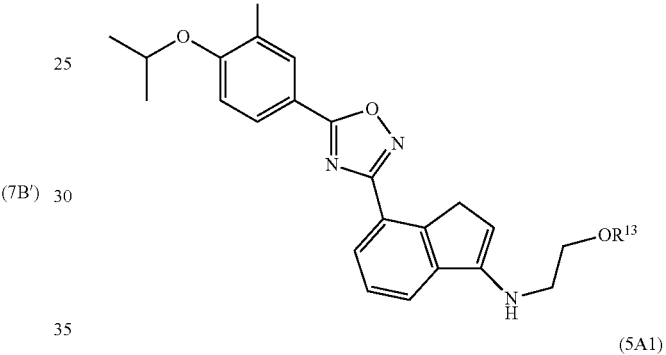
(5A1)
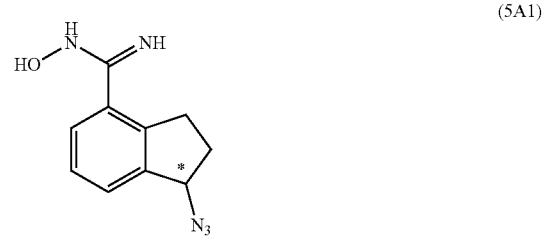
(5B′)
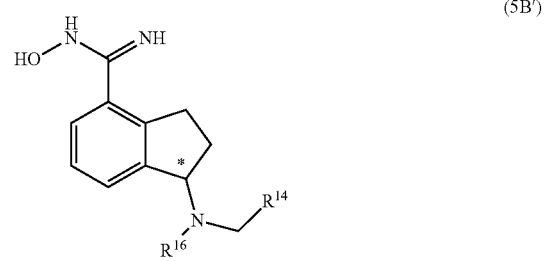
(6′A)
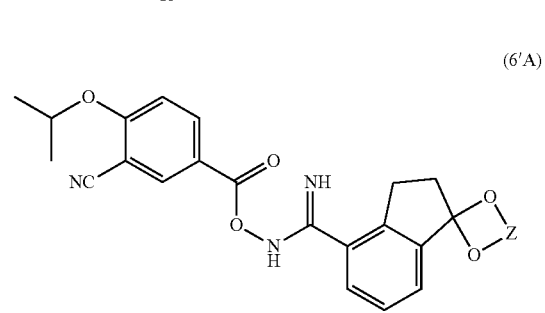

-continued

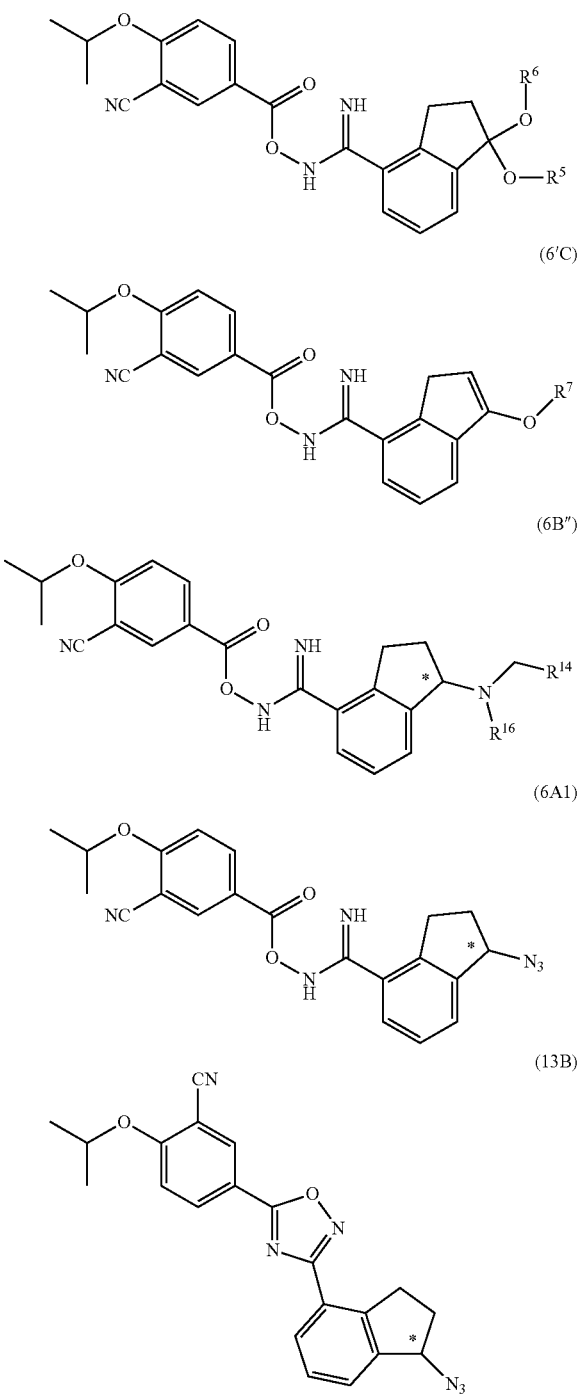

wherein:
R¹ is selected from the group consisting of —ON and 1,2,4-oxadiazole, said 1,2,4-oxadiazole being attached to the bicycle via carbon 3 and optionally substituted in position 5 with a 3'-cyano-4'-isopropoxyphenyl group;
R² is selected from the group consisting of N and NH;
the dashed line indicates a single or a double bond;
R³ and R⁴ are, independently of each other, hydrogen or a linear or branched (C1-C6)alkyl;

R⁵ and R⁶ are, independently of each other, a linear or branched (C1-C8)alkyl;
R⁷ is selected from the group consisting of a linear or branched (C1-C8)alkyl, a linear or branched (C1-C8)alkyl substituted with a (C6-C10)aryl, R⁸C(O)— and (R⁹)₃Si—;
R⁸, and R⁹ are, independently of each other, a linear or branched (C1-C8)alkyl or a linear or branched (C1-C8)alkyl substituted with a (C6-C10)aryl;
R¹⁰ is selected from the group consisting of —CH₂OH, —CH₂OPg and —CO₂R¹²;
R¹¹ is imidazole;
R¹² is selected from the group consisting of H, a linear or branched (C1-C8)alkyl and a linear or branched (C1-C8)alkyl substituted with a (C6-C10)aryl;
R¹³ is selected from the group consisting of H and Pg;
R¹⁴ is —CO₂R¹²;
R¹⁶ is a nitrogen protecting group;
the dashed lines indicate, independently of each other, a single or a double bond;
Pg is an oxygen protecting group;
Y together with the carbon atom to which it is bonded forms a cyclic ketal a ketal or an enol ether;
the * indicates a stereogenic center;
Z is (CR³R⁴)ₙ; and
n is 2 or 3;
with the proviso that:
when the dashed line linked to R² is a double bond R² is N, and when the dashed line linked to R² is a single bond R² is NH;
in the compounds of formula (3), (3A) and (3B), one of the dashed lines indicates a single bond and the other one a double bond,
in the compounds of formula (4), (5), (6) and (6'), when the dashed line indicates a double bond, Y, together with the carbon atom to which it is linked, forms an enol ether;
in the compound of formula (7A") R¹³ is Pg; and
in the compound of formula (7B") R¹⁴ is different from —CO₂H.

The invention claimed is:
1. A process for the preparation of a compound of formula (7) or a salt thereof, said process comprising:
a) reacting an indanone of formula (1) with a compound of formula (2) so as to provide a compound of formula (3);

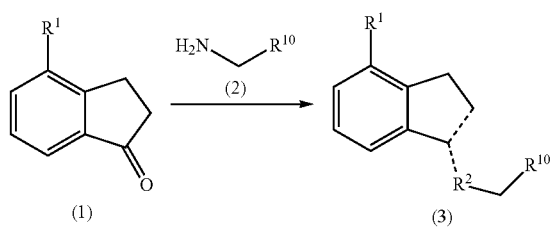

b) treating said compound of formula (3) with a reducing agent to obtain a compound of formula (7) or a salt thereof;

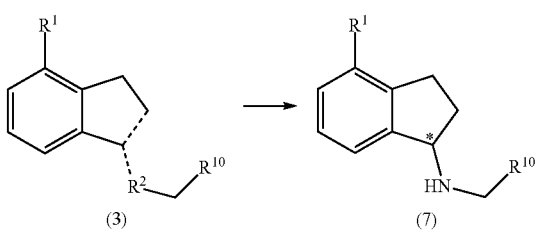

wherein:
$R^1$ is selected from the group consisting of —CN and 1,2,4-oxadiazole, said 1,2,4-oxadiazole being attached to the bicycle via carbon 3 and optionally substituted in position 5 with a 3'-cyano-4'-isopropoxyphenyl group;
one of the dashed lines indicates a single bond and the other one a double bond,
when the dashed line linked to $R^2$ is a double bond, $R^2$ is N, and when the dashed line linked to $R^2$ is a single bond, $R^2$ is NH;
$R^{10}$ is selected from the group consisting of —CH$_2$OH, —CH$_2$OPg and —CO$_2$R$^{12}$;
$R^{12}$ is selected from the group consisting of H, a linear or branched (C1-C8)alkyl or a linear or branched (C1-C8) alkyl substituted with a (C6-C10)aryl;
Pg is an oxygen protecting group; and
the * indicates a stereogenic center;
wherein step a) is carried out in the absence of titanium alkoxides.

2. The process according to claim 1, wherein step a) is carried out in the absence of titanium-based Lewis acids.

3. The process according to claim 1, in which a compound of formula (2A) is used in step a):

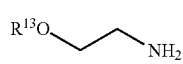

(2A)

wherein:
$R^{13}$ is selected from the group consisting of H and Pg; and
Pg is an oxygen protecting group.

4. The process according to claim 3, wherein the reaction between the indanone of formula (1) and the compound of formula (2A) leads to a compound of formula (3A):

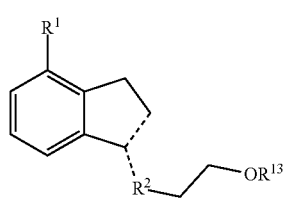

(3A)

wherein
$R^1$ is selected from the group consisting of —CN and 1,2,4-oxadiazole, said 1,2,4-oxadiazole being attached to the bicycle via carbon 3 and optionally substituted in position 5 with a 3'-cyano-4'-isopropoxyphenyl group;
one of the dashed lines indicates a single bond and the other one a double bond,
when the dashed line linked to $R^2$ is a double bond, $R^2$ is N, and when the dashed line linked to $R^2$ is a single bond, $R^2$ is NH;

$R^{13}$ is selected from the group consisting of H and Pg, and Pg is an oxygen protecting group.

5. The process according to claim 4, wherein the reaction between the indanone of formula (1) and the compound of formula (2A) is carried out in a solvent or a mixture of solvents in which the indanone of formula (1) is soluble and the compound of formula (3A) is insoluble.

6. The process according to claim 1, wherein steps a) and b) are carried out without isolating the compound of formula (3).

7. The process according to claim 1, wherein an indanone of formula (1') or (1") is used as a reactant in step a):

(1')

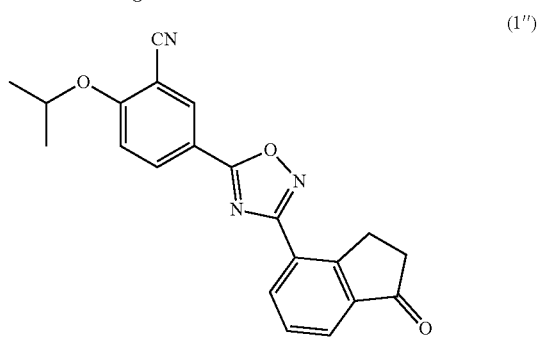

(1")

8. The process according claim 7, wherein the indanone of formula (1") is prepared according to the following steps:

c) providing a protected indanone of formula (4):

(4)

d) treating said protected indanone of formula (4) with hydroxylamine or a salt thereof so as to provide an amidoxime of formula (5), a tautomer or a salt thereof:

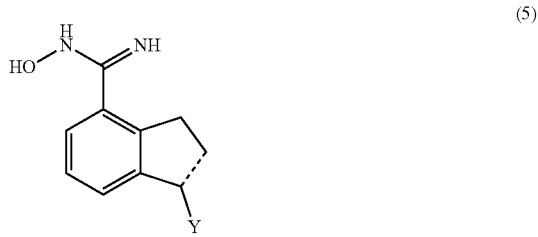

(5)

e) converting said amidoxime of formula (5), the tautomer or the salt thereof, into a protected indanone of formula (6):

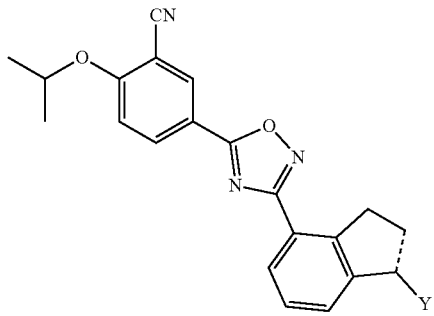

(6)

f) converting said protected indanone of formula (6) into an indanone of formula (1″):

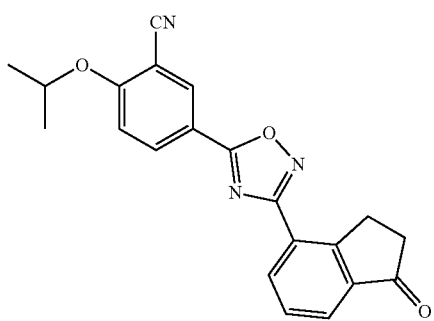

(1″)

wherein:
Y, together with the carbon atom to which it is bonded, forms a cyclic ketal, a ketal or an enol ether; and
the dashed line indicates a single or a double bond;
with the proviso that when the dashed line indicates a double bond, Y, together with the carbon atom to which it is linked, forms an enol ether.

9. The process according to claim 8, wherein the protected indanone of formula (4) is a cyclic ketal of formula (4A), a ketal of formula (4B) or an enol ether of formula (4C):

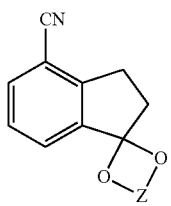

(4A)

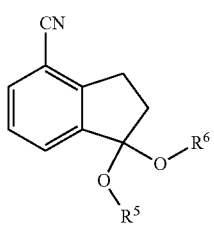

(4B)

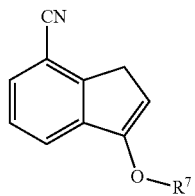

(4C)

wherein:
Z is $(CR^3R^4)_n$;
n is 2 or 3,
$R^3$ and $R^4$ are, independently of each other, hydrogen or a linear or branched (C1-C6)alkyl;
$R^5$ and $R^6$ are, independently of each other, a linear or branched (C1-C8)alkyl;
$R^7$ is selected from the group consisting of a linear or branched (C1-C8)alkyl, a linear or branched (C1-C8) alkyl substituted with a (C6-C10)aryl-, $R^8C(O)$— and $(R^9)_3Si$—; and
$R^8$, and $R^9$ are, independently of each other, a linear or branched (C1-C8)alkyl or a linear or branched (C1-C8) alkyl substituted with a (C6-C10)aryl.

10. The process according to claim 8, wherein step e) is carried out by treating the amidoxime of formula (5), the tautomer or the salt thereof, with a compound of formula (8):

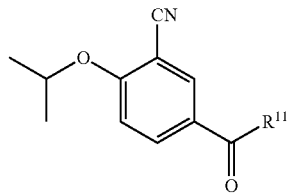

(8)

wherein $R^{11}$ is selected from the group consisting of a linear or branched (C1-C6)alkoxy-, OH, imidazole, and a halogen.

11. The process of claim 10, wherein an additional step e′) is carried after step e), said step e′) comprising heating the mass resulting from the reaction between the compound of formula (8) and the amidoxime of formula (5), the tautomer or the salt thereof, to a temperature from 50° C. to 120° C.

12. The process according to claim 1, wherein step b) is carried out under stereoselective reaction conditions.

13. The process according to claim 1, wherein step b) is carried out in the presence of an asymmetric hydrogenation catalyst of formula (9) or of formula (10):

$$M_m L_n X'_p Y'_q \quad (9)$$

$$[M_m L_n X'_p Y'_q]Z'_s \quad (10)$$

wherein:
M is a transition metal of group VIII of the periodic table of elements;
L is a chiral ligand;
X′ is selected from the group consisting of a halogen atom, a carboxylato group, an allyl group, a 1,5-cyclooctadiene or a norbornadiene;
Y′ is a ligand;
Z′ is an anion; and
m, n′, p, q and s are, independently of each other, an integer from 0 to 5.

14. The process according to claim 13, wherein the chiral ligand L is a diamine of formula (14):

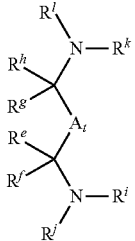

(14)

wherein:
$R^i$, $R^j$, $R^k$ or $R^l$ are independently hydrogen, a saturated or unsaturated alkyl, a cycloalkyl group, an aryl group, a urethane, or a sulphonyl group;
$R^e$, $R^f$, $R^g$ or $R^h$ are independently hydrogen, a saturated or unsaturated alkyl group, a saturated or unsaturated cycloalkyl group, or an aryl group; alternatively, $R^e$ together with —$CR^f$-$A_t$-$CR^g$, $R^e$ together with —$CR^f$-$A_t$-$CR^h$, $R^f$ together with —$CR^e$-$A_t$-$CR^g$ or $R^f$ together with —$CR^e$-$A_t$-$CR^h$ may form a 4- to 8-membered cycloalkyl optionally substituted by 1, 2 or 3 substituents independently selected from (C1-C6)alkyl,
A is a linking group comprising one or two substituted or unsubstituted carbon atoms;
and t is 0 or 1;
with the proviso that $R^e$ to $R^h$ or $R^i$ to $R^l$ or linking group A are chosen such that the ligand is chiral.

15. The process according to claim 13, wherein the chiral ligand L is cyclohexylanisylmethylphosphine (CAMP), 1,2-bis(anisylphenylphosphino)ethane (DIPAMP), 1,2-bis(alkylmethylphosphino)ethane (BisP*), 2,3-bis(diphenylphosphino)butane (CHIRAPHOS), 1,2-bis(diphenylphosphino)propane (PROPHOS), 2,3-bis(diphenylphosphino)-5-norbornene (NORPHOS), 2,3-O-isopropylidene-2,3-dihydroxy-1,4-bis(diphenylphosphino)butane (DIOP), 1-cyclohexyl-1,2-bis(diphenylphosphino)ethane (CYCPHOS), 1-substituted-3,4-bis(diphenylphosphino)pyrrolidine (DEGPHOS), 2,4-bis(diphenylphosphino)pentane (SKEWPHOS), 1,2-bis(substituted-phospholano)benzene (DuPHOS), 1,2-bis(substituted-phospholano)ethane (BPE), 1-((substituted-phospholano)-2-(diphenylphosphino)benzene (UCAP-Ph), 1-(bis(3,5-dimethylphenyl)phosphino)-2-(substituted-phospholano)benzene (UCAP-DM), 1-((substituted-phospholano)-2-(bis(3,5-di(t-butyl)-4-methoxyphenyl)phosphino)benzene (UCAP-DTBM), 1-((substituted-phospholano)-2-(di-naphthalen-1-ylphosphino)benzene (UCAP-(1-Nap)), 1-[1',2-bis(diphenylphosphino)ferrocenyl]ethylamine (BPPFA), 1-[1',2-bis(diphenylphosphino)ferrocenyl]ethyl alcohol (BPPFOH), 2,2'-bis(diphenylphosphino)-1,1'-dicyclopentane (BICP), 2,2'-bis(diphenylphosphino)-1,1'-binaphthyl (BINAP), 2,2'-bis(diphenylphosphino)-1,1'-(5,5',6,6',7,7',8,8'-octahydrobinaphthyl) ($H_8$-BINAP), 2,2'-bis(di-p-tolylphosphino)-1,1'-binaphthyl (TOL-BINAP), 2,2'-bis(di(3,5-dimethylphenyl)phosphino)-1,1'-binaphthyl (DM-BINAP), 2,2'-bis(diphenylphosphino)-6,6'-dimethyl-1,1'-biphenyl (BICHEP), ((5,6),(5',6')-bis(methylenedioxy) biphenyl-2,2'-diyl)(bisdiphenylphosphine) (SEGPHOS), ((5,6),(5',6')-bis(methylenedioxy)biphenyl-2,2'-diyl)(bis(3,5-dimethylphenyl)phosphine) (DM-SEGPHOS), ((5,6),(5',6')-bis(methylenedioxy)biphenyl-2,2'-diyl)(bis(3,5-di(tert-butyl)-4-methoxyphenyl)phosphine) (DTBM-SEGPHOS), H-[P-H8-BINOL]-BoPhoz, N-p-tosyl-1,2-diphenyl ethylenediamine (Ts-DPEN), N-methanesulfonyl-1,2-diphenyl-ethylenediamine (Ms-DPEN), N-[1,2-diphenyl-2-[(3-phenylpropyl)amino]ethyl]-4-methyl-benzenesulfonamide (C3-teth-Ts-DPEN), N-[1,2-diphenyl-2-[(4-phenylbutyl)amino] ethyl]-4-methyl-benzenesulfonamide (C4-teth-Ts-DPEN), N-[1,2-diphenyl-2-[(3-phenylpropyl)amino]ethyl]-methanesulfonamide (C3-teth-Ms-DPEN), N-[1,2-diphenyl-2-[(4-phenylbutyl)amino]ethyl]-methanesulfonamide (C4-teth-Ms-DPEN), N-[1,2-diphenyl-2-[(3-phenylpropyl)amino]ethyl]-2,4,6-trimethyl-benzenesulfonamide (C3-teth-Mts-DPEN), N-[1,2-diphenyl-2-[(4-phenylbutyl)amino]ethyl]-2,4,6-trimethyl-benzenesulfonamide (C4-teth-Mts-DPEN), N-[1,2-diphenyl-2-[(3-phenylpropyl)amino]ethyl]-2,4,6-triisopropyl-benzenesulfonamide (C3-teth-Tris-DPEN), N-[1,2-diphenyl-2-[(4-phenylbutyl)amino]ethyl]-2,4,6-triisopropyl-benzenesulfonamide (C4-teth-Tris-DPEN), N-p-tosyl-1,2-cyclohexanediamine (Ts-DACH), 2,2',6,6'-tetramethoxy-4,4'-bis(diphenylphosphino)-3,3'-bipyridine (P-Phos), 4,12-bis(diphenylphosphino)-[2.2]-paracyclophane (Phanephos), or 1-(diphenylphosphino)-2-[1-[(diphenylphosphino)methylamino]ethyl]ferrocene (MeBoPhoz).

16. The process according to claim 1, wherein step b) is carried out in the presence of a compound of formula (2), (2A) or (2B):

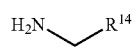

(2B)

wherein:
$R^{14}$ is —$CO_2R^{12}$; and
$R^{12}$ is as defined in claim 1.

17. The process according to claim 1, further comprising converting the compound of formula (7) or the salt thereof into Ozanimod or a salt thereof.

18. The process according to claim 4, wherein steps a) and b) are carried out without isolating the compound of formula (3A).

* * * * *